US011499157B2

(12) United States Patent
Luo et al.

(10) Patent No.: US 11,499,157 B2
(45) Date of Patent: Nov. 15, 2022

(54) IMMUNOMODULATORY SMALL HAIRPIN RNA MOLECULES

(71) Applicants: Nanyang Technological University, Singapore (SG); Agency for Science, Technology and Research, Singapore (SG)

(72) Inventors: Dahai Luo, Singapore (SG); Katja Fink, Singapore (SG); Hui Yee Yong, Singapore (SG); Chin Yong Victor Ho, Singapore (SG)

(73) Assignees: Nanyang Technological University, Singapore (SG); Agency for Science, Technology and Research, Singapore (SG)

( * ) Notice: Subject to any disclaimer, the term of this patent is extended or adjusted under 35 U.S.C. 154(b) by 0 days.

(21) Appl. No.: 16/960,634

(22) PCT Filed: Jan. 17, 2019

(86) PCT No.: PCT/SG2019/050029
§ 371 (c)(1),
(2) Date: Jul. 8, 2020

(87) PCT Pub. No.: WO2019/143297
PCT Pub. Date: Jul. 25, 2019

(65) Prior Publication Data
US 2021/0000856 A1 Jan. 7, 2021

(30) Foreign Application Priority Data
Jan. 17, 2018 (SG) .............................. 10201800434S

(51) Int. Cl.
*C07H 21/04* (2006.01)
*C12N 15/117* (2010.01)
*A61K 31/713* (2006.01)
*C12N 15/113* (2010.01)
*A61K 45/06* (2006.01)

(52) U.S. Cl.
CPC .......... *C12N 15/117* (2013.01); *A61K 31/713* (2013.01); *C12N 15/113* (2013.01); *A61K 45/06* (2013.01); *C12N 2310/14* (2013.01); *C12N 2310/17* (2013.01); *C12N 2310/20* (2017.05); *C12N 2310/531* (2013.01); *C12N 2320/31* (2013.01)

(58) Field of Classification Search
CPC ........................ C12N 15/113; C12N 2310/531
See application file for complete search history.

(56) References Cited

FOREIGN PATENT DOCUMENTS

| WO | WO 2008/048976 A2 * | 4/2008 | ........... C12N 15/113 |
|---|---|---|---|
| WO | 2014159990 A1 | 10/2014 | |
| WO | 2017065563 A1 | 4/2017 | |

OTHER PUBLICATIONS

Lee et al. (Nucleic Acids Research, 2016, 44, 17, 8407-8416).*
Frankish et al., "GENCODE Reference Annotation for the Human and Mouse Genomes," Nucleic Acids Research, vol. 47, 2019, pp. D766-D773.
Patro et al., "Salmon: Fast and Bias-Aware Quantification of Transcript Expression Using Dual-Phase Inference," Nature Methods, vol. 14, No. 4, 2017, pp. 417-419.
Soneson et al., "Differential Analyses for RNA-seq: Transcript-Level Estimates Improve Gene-Level Inferences," F1000 Research, vol. 4, No. 1521, 2015, pp. 1-19.
Love et al., "Moderated Estimation of Fold Change and Dispersion for RNA-seq Data with DESeq2,"Genome Biology, vol. 15, No. 550, 2014, pp. 1-21.
Lee et al., "Systematic Editing of Synthetic RIG-I Ligands to Produce Effective Antiviral and Anti-Tumor RNA Immunotherapies," Nucleic Acids Research, vol. 46, No. 4, 2018, pp. 1635-1647.
McGovern et al., "Human Dermal CD14$^+$ Cells are a Transient Population of Monocyte-Derived Macrophages," Immunity, vol. 41, 2014, pp. 465-477.
Lässig et al., "ATP Hydrolysis by the Viral RNA Sensor RIG-I Prevents Unintentional Recognition of Self-RNA," eLife, vol. 4, 2015, pp. 1-20.
Schmid et al., "Dendritic Cells in Dengue Virus Infection: Targets of Virus Replication and Mediators of Immunity," Frontiers in Immunology, vol. 5, Article 647, 2014, pp. 1-10.
Kulkarni et al., "Activation of the RIG-I Pathway During Influenza Vaccination Enhances the Germinal Center Reaction, Promotes T Follicular Helper Cell Induction, and Provides a Dose-Sparing Effect and Protective Immunity," Journal of Virology, vol. 88, No. 24, Dec. 2014, pp. 13990-14001.
Sprokholt et al.,"RIG-I-Like Receptor Activation by Dengue Virus Drives Follicular T Helper Cell Formation and Antibody Production," PLoS Pathogens, vol. 13, No. 11, 2017, pp. 1-19.
Martin Schlee, "Master Sensors of Pathogenic RNA—RIG-I Like Receptors," Immunobiology, vol. 218, 2013, pp. 1322-1335.
Peisley et al., Structural Basis for Ubiquitin-Mediated Antiviral Signal Activation by RIG-I, Nature, vol. 509, May 2014, pp. 110-114.
Wu et al., "Molecular Imprinting as a Signal-Activation Mechanism of the Viral RNA Sensor RIG-I," Molecular Cell, vol. 55, Aug. 21, 2014, pp. 511-523.
Loo et al., Immune Signaling by RIG-I-Like Receptors, Immunity, vol. 34, May 27, 2011, pp. 680-692.
Wu et al., "wInnate Immune Sensing and Signaling of Cytosolic Nucleic Acids," Annual Review of Immunology, vol. 32, 2014, pp. 461-488.
Zheng et al., High-Resolution HDX-MS Reveals Distinct Mechanisms of RNA Recognition and Activation by RIG-I and MDA5, Nucleic Acids Research, vol. 43, 2014, pp. 1216-1230.

(Continued)

*Primary Examiner* — Amy H Bowman
(74) *Attorney, Agent, or Firm* — Shackelford, Bowen, McKinley & Norton, LLP

(57) ABSTRACT

The present invention generally relates to specific immune-modulatory RNA species that have a small hairpin structure (shRNA), and that can bind to retinoic acid inducible gene I receptor (RIG-I). In particular, said RNA species comprise a nucleotide insertion to create a kink in the stem region. Also encompassed are compositions comprising such shRNA, for use as antiviral or anticancer medication, or as adjuvants in vaccine.

18 Claims, 21 Drawing Sheets
Specification includes a Sequence Listing.

(56) References Cited

OTHER PUBLICATIONS

Kowalinski et al., "Structural Basis for the Activation of Innate Immune Pattern-Recognition Receptor RIG-I by Viral RNA," Cell, vol. 147, Oct. 14, 2011, pp. 423-435.
Hiscott et al., "MasterCARD: a Priceless Link to Innate Immunity," TRENDS in Molecular Medicine, vol. 12, No. 2, Feb. 2006, pp. 53-56.
Iwanaszko et al., "NF-κB and IRF Pathways: Cross-Regulation on Target Genes Promoter Level," BMC Genomics, vol. 16, No. 307, 2015, pp. 1-8.
Ramos et al., "RIG-I Like Receptors and their Signaling Crosstalk in the Regulation of Antiviral Immunity," Current Opinion in Virology, vol. 1, 2011, pp. 167-176.
Runge et al., "In Vivo Ligands of MDA5 and RIG-I in Measles Virus-Infected Cells," PLoS Pathogens, vol. 10, 2014, pp. 1-12.
Schnell et al., "Uridine Composition of the Poly-U/UC Tract of HCV RNA Defines Non-Self Recognition by RIG-I," PLoS Pathogens, vol. 8, 2012, pp. 1-11.
Elion et al., "Harnessing RIG-I and Intrinsic Immunity in the Tumor Microenvironment for Therapeutic Cancer Treatment," Oncotarget, vol. 9, No. 48, 2018, pp. 29007-29017.
Elion et al., "Therapeutically Active RIG-I Agonist Induces Immunogenic Tumor Cell Killing in Breast Cancers," Cancer Research, vol. 78, No. 21, Nov. 1, 2018, pp. 6183-6195.
Duewell et al., "RIG-I-Like Helicases Induce Immunogenic Cell Death of Pancreatic Cancer Cells and Sensitize Tumors Toward Killing by CD8 + T Cells," Cell Death and Differentiation, vol. 21, 2014, pp. 1825-1837.
Yong et al., "RiG-i-Like Receptors as Novel Targets for Pan-Antivirals and Vaccine Adjuvants Against Emerging and Re-Emerging Viral Infections," Frontiers in Immunology, vol. 9, Article 1379, Jul. 2018, pp. 1-9.
Kato et al., "Differential Roles of MDA5 and RIG-I Helicases in the Recognition of RNA Viruses," Nature, vol. 441, May 4, 2006, pp. 101-105.
Schmidt et al., "5'-triphosphate RNA Requires Base-Paired Structures to Activate Antiviral Signaling via RIG-I," Proceedings of the National Academy of Sciences of the United States of America, vol. 106, No. 29, Jul. 21, 2009, pp. 12067-12072.
Zust et al., "Type I Interferon Signals in Macrophages and Dendritic Cells Control Dengue Virus Infection: Implications for a New Mouse Model To Test Dengue Vaccines," Journal of Virology, vol. 88, No. 13, Jul. 2014, pp. 7276-7285.
Louber et al., "Kinetic Discrimination of Self/Non-Self RNA by the ATPase Activity of RIG-I and MDA5," BMC Biology, vol. 13, No. 54, 2015, pp. 1-16.
Zheng et al., "HDX Reveals the Conformational Dynamics of DNA Sequence Specific VDR Co-Activator Interactions," Nature Communications, vol. 8, No. 923, 2017, pp. 1-13.
Keppel et al., "Mapping Residual Structure in Intrinsically Disordered Proteins at Residue Resolution Using Millisecond Hydrogen/Deuterium Exchange and Residue Averaging," Journal of the American Society for Mass Spectrometry, vol. 26, 2015, pp. 547-554.
Pascal et al., "HDXWorkbench: Software for the Analysis of H/D Exchange MS Data," Journal of the American Society for Mass Spectrometry, vol. 23, 2012, pp. 1512-1521.
Lee et al., "Structural Features of Influenza A Virus Panhandle RNA Enabling the Activation of RIG-I Independently of 5'-triphosphate," Nucleic Acids Research, vol. 44, No. 17, 2016, pp. 8407-8416.
Liu et al., "Influenza A Virus Panhandle Structure Is Directly Involved in RIG-I Activation and Interferon Induction," Journal of Virology, vol. 89, No. 11, Jun. 2015, pp. 6067-6079.
White et al., "Single Base Bulges in Small RNA Hairpins Enhance Ethidium Binding and Promote an Allosteric Transition," Nucleic Acids Research, vol. 15, No. 10, 1987, pp. 4049-4064.
Hochheiser et al., "Cutting Edge: The RIG-I Ligand 3pRNA Potently Improves CTL Cross-Priming and Facilitates Antiviral Vaccination," The Journal of Immunology, vol. 196, Jan. 27, 2016, pp. 2439-2443.

International Search Report for International Application No. PCT/SG2019/050029 dated Apr. 8, 2019, pp. 1-7.
Written Opinion of the International Searching Authority for International Application No. PCT/SG2019/050029 dated Apr. 8, 2019, pp. 1-7.
Thompson et al. "Pattern Recognition Receptors and the Innate Immune Response to Viral Infection," Viruses, vol. 3, No. 6, 2011, pp. 920-940.
Horunung et al.,"5'-Triphosphate RNA is the Ligand for RIG-I," Science, vol. 314, Nov. 10, 2006, pp. 994-997.
Schlee et al., "Recognition of 5' Triphosphate by RIG-I Helicase Requires Short Blunt Double-Stranded RNA as Contained in Panhandle of Negative-Strand Virus," Immunity, vol. 31, No. 1, Jul. 17, 2009, pp. 25-34.
Strahle et al., "Sendai Virus Defective-Interfering Genomes and the Activation of Interferon-Beta," Virology, vol. 351, No. 1, 2005, pp. 101-111.
Devarkar et al., "Structural Basis for m7G Recognition and 2'-O-methyl Discrimination in Capped RNAs by the Innate Immune Receptor RIG-I," Proceedings of the National Academy of Sciences of the United States of America, vol. 113, No. 3, 2016, pp. 596-601.
Goubau et al., "Antiviral Immunity via RIG-I-Mediated Recognition of RNA Bearing 5'-diphosphates," Nature, vol. 514, No. 7522, 2014, pp. 372-375.
Kohlway et al., "Defining the Functional Determinants for RNA Surveillance by RIG-I," EMBO Reports, vol. 14, No. 9, 2013, pp. 772-779.
Luo et al., "Duplex RNA Activated ATPases (DRAs): Platforms for RNA Sensing, Signaling and Processing," RNA Biology, vol. 10, No. 1, 2013, pp. 111-120.
Luo et al., "Structural Insights into RNA Recognition by RIG-I," Cell, vol. 147, No. 2, 2011, pp. 409-422.
Wang et al., "Structural and Functional Insights into 5'-ppp RNA Pattern Recognition by the Innate Immune Receptor RIG-I," Nature Structural & Molecular Biology, vol. 17, No. 7, Jul. 2010, pp. 781-787.
Lu et al., "The Structural Basis of 5' Triphosphate Double-Stranded RNA Recognition by RIG-I C-Terminal Domain," Structure, vol. 18, No. 8, 2010, pp. 1032-1043.
Wu et al., "Structural Basis for dsRNA Recognition, Filament Formation, and Antiviral Signal Activation by MDA5," Cell, vol. 152, 2013, pp. 276-289.
Li et al., "The RIG-I-Like Receptor LGP2 Recognizes the Termini of Double-Stranded RNA," Journal of Biological Chemistry, vol. 284, No. 20, 2009, pp. 13881-13891.
Van Den Boorn et al., "Turning Tumors into Vaccines: Co-opting the Innate Immune System," Immunity, vol. 39, No. 1, 2013, pp. 27-37.
Beljanski et al., "Enhanced Influenza Virus-Like Particle Vaccination with a Structurally Optimized RIG-I Agonist as Adjuvant," Journal of Virology, vol. 89, No. 20, 2015, pp. 10612-10624.
Goulet et al., "Systems Analysis of a RIG-I Agonist Inducing Broad Spectrum Inhibition of Virus Infectivity," PLoS Pathogens, vol. 9, No. 4, 2013, pp. 1-19.
Chiang et al., "Sequence-Specific Modifications Enhance the Broad-Spectrum Antiviral Response Activated by RIG-I Agonists," Journal of Virology, vol. 89, No. 15, 2015, pp. 8011-8025.
Olagnier et al., "Inhibition of Dengue and Chikungunya Virus Infections by RIG-I-Mediated Type I Interferon-Independent Stimulation of the Innate Antiviral Response," Journal of Virology, vol. 88, No. 8, 2014, pp. 4180-4194.
Cerny et al., "Selective Susceptibility of Human Skin Antigen Presenting Cells to Productive Dengue Virus Infection," PLoS Pathogens, vol. 10, No. 12, 2014, pp. 1-15.
Ho et al., "RIG-I Activation by a Designer Short RNA Ligand Protects Human Immune Cells against Dengue Virus Infection without Causing Cytotoxicity," Journal of Virology, vol. 93, No. 14, 2019, pp. 1-18.
Painter et al., "Antiviral Protection via RdRP-Mediated Stable Activation of Innate Immunity," PLoS Pathogens, vol. 11, No. 12, 2015, pp. 1-22.

(56) References Cited

OTHER PUBLICATIONS

Moore et al., "Established T Cell-Inflamed Tumors Rejected after Adaptive Resistance Was Reversed by Combination STING Activation and PD-1 Pathway Blockade," Cancer Immunology Research, vol. 4, 2016, pp. 1061-1071.
Junt et al., "Translating Nucleic Acid-Sensing Pathways into Therapies," Nature Reviews, vol. 15, 2015, pp. 529-544.
Ishibashi et al., "Short RNA Duplexes Elicit RIG-I-Mediated Apoptosis in a Cell Type—and Length-Dependent Manner." Science Signaling, vol. 4, No. 198, 2011, pp. 1-11.
Loo et al., "Distinct RIG-I and MDA5 Signaling by RNA Viruses in Innate Immunity," Journal of Virology, vol. 82, No. 1, pp. 335-345.
Dahai Luo, "Toward a Crystal-Clear View of the Viral RNA Sensing and Response by RIG-I-like Receptors," RNA Biology, vol. 11, No. 1, Jan. 2014, pp. 25-32.
Luo et al., "Visualizing the Determinants of Viral RNA Recognition by Innate Immune Sensor RIG-I," Structure, vol. 20, Nov. 7, 2012, pp. 1983-1988.
Chazal et al., "RIG-I Recognizes the 5' Region of Dengue and Zika Virus Genomes," Cell Reports, vol. 24, 2018, pp. 320-328.
Kawai et al., "IPS-1, an Adaptor Triggering RIG-I- and Mda5-Mediated Type I Interferon Induction," Nature Immunology, vol. 6, No. 10, Oct. 2005, pp. 981-988.
Seth et al., "Identification and Characterization of MAVS, a Mitochondrial Antiviral Signaling Protein that Activates NF-kappaB and IRF3," Cell, vol. 122, 2005, pp. 669-682.
Meylan et al., "Cardif is an Adaptor Protein in the RIG-I Antiviral Pathway and is Targeted by Hepatitis C Virus," Nature, vol. 437, 2005, pp. 1167-1172.
Xu et al., "VISA is an Adapter Protein Required for Virus-Triggered IFN-beta Signaling," Molecular Cell, vol. 19, 2005, pp. 727-740.
Horvath et al., "Interactions Between STAT and non-STAT Proteins in the Interferon-Stimulated Gene Factors Transcription Complex," Molecular and Cellular Biology, vol. 16, No. 12, Dec. 1996, pp. 6957-6964.
Levy et al., "Interferon-induced Nuclear Factors that Bind a Shared Promoter Element Correlate with Positive and Negative Transcriptional Control," Genes and Development, vol. 2, 1988, pp. 383-393.
Fu et al., "ISGF3, the Transcriptional Activator Induced by Interferon Alpha, Consists of Multiple Interacting Polypeptide Chains," PNAS, vol. 87, Nov. 1990, pp. 8555-8559.
Linehan et al., "A minimal RNA Ligand for Potent RIG-I Activation in Living Mice," Science Advances, vol. 4, 2018, pp. 1-10.
Kubo et al., "External Antigen Uptake by Langerhans Cells with Reorganization of Epidermal Tight Junction Barriers," The Journal of Experimental Medicine, vol. 206, No. 13, 2009, pp. 2937-2946.
Wang et al., "A Three-Dimensional Atlas of Human Dermal Leukocytes, Lymphatics, and Blood Vessels," Journal of Investigative Dermatology, vol. 134, 2014, pp. 965-974.
Kou et al., "Monocytes, But not T or B Cells, are the Principal Target Cells for Dengue Virus (DV) Infection Among Human Peripheral Blood Mononuclear Cells," Journal of Medical Virology, vol. 80, 2008, pp. 134-146.
Wu et al., "Human Skin Langerhans Cells are Targets of Dengue Virus Infection," Nature Medicine, vol. 6, No. 7, Jul. 2000, pp. 816-820.
Fink et al., "Depletion of Macrophages in Mice Results in Higher Dengue Virus Titers and Highlights the Role of Macrophages for Virus Control," European Journal of Immunology, vol. 39, 2009, pp. 2809-2821.
Schmid et al., "Monocyte Recruitment to the Dermis and Differentiation to Dendritic Cells Increases the Targets for Dengue Virus Replication," PLoS Pathogens, vol. 10, No. 12, 2014, pp. 1-18.
Zust et al., "Rational Design of a Live Attenuated Dengue Vaccine: 2'-O-Methyltransferase Mutants Are Highly Attenuated and Immunogenic in Mice and Macaques," PLoS Pathogens, vol. 9, No. 8, Aug. 2013, pp. 1-13.
Kochs et al., "Strong Interferon-Inducing Capacity of a Highly Virulent Variant of Influenza A Virus Strain PR8 with Deletions in the NS1 Gene," Journal of General Virology, vol. 90, 2009, pp. 2990-2994.
Truett et al., "Preparation of PCR-Quality Mouse Genomic DNA with Hot Sodium Hydroxide and Tris (HotSHOT)," BioTechniques, vol. 29, No. 1, 2000, pp. 52-54.
Grant et al., "A single Amino Acid in Nonstructural Protein NS4B Confers Virulence to Dengue Virus in AG129 Mice Through Enhancement of Viral RNA Synthesis," Journal of Virology, vol. 85, No. 15, Aug. 2011, pp. 7775-7787.
Picelli et al., "Full-Length RNA-seq from Single Cells Using Smart-seq2," Nature Protocols, vol. 9, No. 1, 2014, pp. 171-181.
Li et al., "RSEM: Accurate Transcript Quantification from RNA-Seq Data with or without a Reference Genome," BMC Bioinformatics, vol. 12, No. 323, 2011, pp. 1-16.
Butler et al., "Integrating Single-Cell Transcriptomic Data Across Different Conditions, Technologies, and Species," Nature Biotechnology, vol. 36, No. 5, 2018, pp. 411-420.

* cited by examiner

B

C

C

A

ATPase activity for ImmRNA stem modification

B

ATPase activity for ImmRNA with different base composition

C

ATPase rate vs Substrate concentration for mmRIG-I with RNA of different length

A

B

A

B

C

A

B

A

B

SEQUENCE LISTING

<160> NUMBER OF SEQ ID NOS: 55

<210> SEQ ID NO 1
<211> LENGTH: 11
<212> TYPE: RNA
<213> ORGANISM: artificial
<220> FEATURE:
<223> OTHER INFORMATION: shRNA sequence
<220> FEATURE:
<221> NAME/KEY: misc_feature
<222> LOCATION: (4)..(5)
<223> OTHER INFORMATION: n is a, c, g, or u

<400> SEQUENCE: 1
rrrnnyyyry y                                                          11

<210> SEQ ID NO 2
<211> LENGTH: 11
<212> TYPE: RNA
<213> ORGANISM: Artificial
<220> FEATURE:
<223> OTHER INFORMATION: shRNA sequence

<400> SEQUENCE: 2
sswwwwssrs s					11

<210> SEQ ID NO 3
<211> LENGTH: 11
<212> TYPE: RNA
<213> ORGANISM: Artificial
<220> FEATURE:
<223> OTHER INFORMATION: shRNA sequence
<220> FEATURE:
<221> NAME/KEY: misc_feature
<222> LOCATION: (4)..(11)
<223> OTHER INFORMATION: n is a, c, g, or u

<400> SEQUENCE: 3
ggannnnnnn n					11

<210> SEQ ID NO 4
<211> LENGTH: 11
<212> TYPE: RNA
<213> ORGANISM: Artificial
<220> FEATURE:
<223> OTHER INFORMATION: shRNA sequence
<220> FEATURE:
<221> NAME/KEY: misc_feature
<222> LOCATION: (4)..(9)
<223> OTHER INFORMATION: n is a, c, g, or u

<400> SEQUENCE: 4
ggannnnnnc c					11

<210> SEQ ID NO 5
<211> LENGTH: 11
<212> TYPE: RNA
<213> ORGANISM: Artificial
<220> FEATURE:
<223> OTHER INFORMATION: shRNA sequence
<220> FEATURE:
<221> NAME/KEY: misc_feature
<222> LOCATION: (4)..(5)
<223> OTHER INFORMATION: n is a, c, g, or u
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(9)
<223> OTHER INFORMATION: n is a, c, g, or u

<400> SEQUENCE: 5
ggannuncnc c					11

<210> SEQ ID NO 6
<211> LENGTH: 11
<212> TYPE: RNA
<213> ORGANISM: Artificial
<220> FEATURE:
<223> OTHER INFORMATION: shRNA sequence
<220> FEATURE:
<221> NAME/KEY: misc_feature
<222> LOCATION: (9)..(9)
<223> OTHER INFORMATION: n is a, c, g, or u

<400> SEQUENCE: 6
ggawwuscnc c					11

<210> SEQ ID NO 7
<211> LENGTH: 11
<212> TYPE: RNA

```
<213> ORGANISM: Artificial
<220> FEATURE:
<223> OTHER INFORMATION: shRNA sequence

<400> SEQUENCE: 7
ggauuuccrc c                                                          11

<210> SEQ ID NO 8
<211> LENGTH: 11
<212> TYPE: RNA
<213> ORGANISM: Artificial
<220> FEATURE:
<223> OTHER INFORMATION: shRNA sequence

<400> SEQUENCE: 8
ggauuuccac c                                                          11

<210> SEQ ID NO 9
<211> LENGTH: 11
<212> TYPE: RNA
<213> ORGANISM: Artificial
<220> FEATURE:
<223> OTHER INFORMATION: shRNA sequence

<400> SEQUENCE: 9
ggauuuccgc c                                                          11

<210> SEQ ID NO 10
<211> LENGTH: 10
<212> TYPE: RNA
<213> ORGANISM: Artificial
<220> FEATURE:
<223> OTHER INFORMATION: shRNA sequence
<220> FEATURE:
<221> NAME/KEY: misc_feature
<222> LOCATION: (6)..(7)
<223> OTHER INFORMATION: n is a, c, g, or u

<400> SEQUENCE: 10 rrrrrnnyyy                                                            10

<210> SEQ ID NO 11
<211> LENGTH: 10
<212> TYPE: RNA
<213> ORGANISM: Artificial
<220> FEATURE:
<223> OTHER INFORMATION: shRNA sequence

<400> SEQUENCE: 11 sssswwwwss                                                            10

<210> SEQ ID NO 12
<211> LENGTH: 10
<212> TYPE: RNA
<213> ORGANISM: Artificial
<220> FEATURE:
<223> OTHER INFORMATION: shRNA sequence
<220> FEATURE:
<221> NAME/KEY: misc_feature
<222> LOCATION: (1)..(7)
<223> OTHER INFORMATION: n is a, c, g, or u

<400> SEQUENCE: 12 nnnnnnnucc                                                            10

<210> SEQ ID NO 13
<211> LENGTH: 10
```

```
<212> TYPE: RNA
<213> ORGANISM: Artificial
<220> FEATURE:
<223> OTHER INFORMATION: shRNA sequence
<220> FEATURE:
<221> NAME/KEY: misc_feature
<222> LOCATION: (3)..(7)
<223> OTHER INFORMATION: n is a, c, g, or u

<400> SEQUENCE: 13 ggnnnnnucc                                                          10

<210> SEQ ID NO 14
<211> LENGTH: 10
<212> TYPE: RNA
<213> ORGANISM: Artificial
<220> FEATURE:
<223> OTHER INFORMATION: shRNA sequence
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (6)..(7)
<223> OTHER INFORMATION: n is a, c, g, or u

<400> SEQUENCE: 14 gggnannucc                                                          10

<210> SEQ ID NO 15
<211> LENGTH: 10
<212> TYPE: RNA
<213> ORGANISM: Artificial
<220> FEATURE:
<223> OTHER INFORMATION: shRNA sequence

<400> SEQUENCE: 15 gggwawwucc                                                          10

<210> SEQ ID NO 16
<211> LENGTH: 10
<212> TYPE: RNA
<213> ORGANISM: Artificial
<220> FEATURE:
<223> OTHER INFORMATION: shRNA sequence

<400> SEQUENCE: 16
ggggaaaucc                                                          10

<210> SEQ ID NO 17
<211> LENGTH: 25
<212> TYPE: RNA
<213> ORGANISM: Artificial
<220> FEATURE:
<223> OTHER INFORMATION: shRNA
<220> FEATURE:
<221> NAME/KEY: misc_feature
<222> LOCATION: (4)..(5)
<223> OTHER INFORMATION: n is a, c, g, or u
<220> FEATURE:
<221> NAME/KEY: misc_feature
<222> LOCATION: (21)..(22)
<223> OTHER INFORMATION: n is a, c, g, or u

<400> SEQUENCE: 17
rrrnnyyyry yuucgrrrrr nnyyy                                         25

<210> SEQ ID NO 18
```

```
<211> LENGTH: 25
<212> TYPE: RNA
<213> ORGANISM: Artificial
<220> FEATURE:
<223> OTHER INFORMATION: shRNA

<400> SEQUENCE: 18
sswwwwssrs suucgssssw wwwss                                              25

<210> SEQ ID NO 19
<211> LENGTH: 25
<212> TYPE: RNA
<213> ORGANISM: Artificial
<220> FEATURE:
<223> OTHER INFORMATION: shRNA
<220> FEATURE:
<221> NAME/KEY: misc_feature
<222> LOCATION: (4)..(11)
<223> OTHER INFORMATION: n is a, c, g, or u
<220> FEATURE:
<221> NAME/KEY: misc_feature
<222> LOCATION: (16)..(22)
<223> OTHER INFORMATION: n is a, c, g, or u

<400> SEQUENCE: 19
ggannnnnnn nuucgnnnnn nnucc                                              25

<210> SEQ ID NO 20
<211> LENGTH: 25
<212> TYPE: RNA
<213> ORGANISM: Artificial
<220> FEATURE:
<223> OTHER INFORMATION: shRNA
<220> FEATURE:
<221> NAME/KEY: misc_feature
<222> LOCATION: (4)..(9)
<223> OTHER INFORMATION: n is a, c, g, or u
<220> FEATURE:
<221> NAME/KEY: misc_feature
<222> LOCATION: (18)..(22)
<223> OTHER INFORMATION: n is a, c, g, or u

<400> SEQUENCE: 20
ggannnnnnc cuucgggnnn nnucc                                              25

<210> SEQ ID NO 21
<211> LENGTH: 25
<212> TYPE: RNA
<213> ORGANISM: Artificial
<220> FEATURE:
<223> OTHER INFORMATION: shRNA
<220> FEATURE:
<221> NAME/KEY: misc_feature
<222> LOCATION: (4)..(5)
<223> OTHER INFORMATION: n is a, c, g, or u
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(9)
<223> OTHER INFORMATION: n is a, c, g, or u
<220> FEATURE:
<221> NAME/KEY: misc_feature
<222> LOCATION: (19)..(19)
<223> OTHER INFORMATION: n is a, c, g, or u
<220> FEATURE:
<221> NAME/KEY: misc_feature
<222> LOCATION: (21)..(22)
<223> OTHER INFORMATION: n is a, c, g, or u

<400> SEQUENCE: 21
```
ggannuncnc cuucggggna nnucc                          25

<210> SEQ ID NO 22
<211> LENGTH: 25
<212> TYPE: RNA
<213> ORGANISM: Artificial
<220> FEATURE:
<223> OTHER INFORMATION: shRNA
<220> FEATURE:
<221> NAME/KEY: misc_feature
<222> LOCATION: (9)..(9)
<223> OTHER INFORMATION: n is a, c, g, or u

<400> SEQUENCE: 22
ggawwuscnc cuucggggwa wwucc                          25

<210> SEQ ID NO 23
<211> LENGTH: 25
<212> TYPE: RNA
<213> ORGANISM: Artificial
<220> FEATURE:
<223> OTHER INFORMATION: shRNA
<220> FEATURE:
<221> NAME/KEY: misc_feature
<222> LOCATION: (9)..(9)
<223> OTHER INFORMATION: n is a, c, g, or u

<400> SEQUENCE: 23
ggauuuccnc cuucggggga aaucc                          25

<210> SEQ ID NO 24
<211> LENGTH: 25
<212> TYPE: RNA
<213> ORGANISM: Artificial
<220> FEATURE:
<223> OTHER INFORMATION: shRNA

<400> SEQUENCE: 24
ggauuuccrc cuucggggga aaucc                          25

<210> SEQ ID NO 25
<211> LENGTH: 25
<212> TYPE: RNA
<213> ORGANISM: Artificial
<220> FEATURE:
<223> OTHER INFORMATION: shRNA

<400> SEQUENCE: 25
ggauuuccac cuucggggga aaucc                          25

<210> SEQ ID NO 26
<211> LENGTH: 25
<212> TYPE: RNA
<213> ORGANISM: Artificial
<220> FEATURE:
<223> OTHER INFORMATION: shRNA

<400> SEQUENCE: 26
ggauuuccgc cuucggggga aaucc                          25

<210> SEQ ID NO 27
<211> LENGTH: 25
<212> TYPE: RNA
<213> ORGANISM: Artificial
<220> FEATURE:
<223> OTHER INFORMATION: shRNA

```
<400> SEQUENCE: 27
ggagguuucc uucgggaaac gcucc                                         25

<210> SEQ ID NO 28
<211> LENGTH: 25
<212> TYPE: RNA
<213> ORGANISM: Artificial
<220> FEATURE:
<223> OTHER INFORMATION: shRNA

<400> SEQUENCE: 28
ggauuucggc uucggcgcga aaucc                                         25

<210> SEQ ID NO 29
<211> LENGTH: 25
<212> TYPE: RNA
<213> ORGANISM: Artificial
<220> FEATURE:
<223> OTHER INFORMATION: shRNA

<400> SEQUENCE: 29
ggauucgcuc cuucgggagg aaucc                                         25

<210> SEQ ID NO 30
<211> LENGTH: 25
<212> TYPE: RNA
<213> ORGANISM: Artificial
<220> FEATURE:
<223> OTHER INFORMATION: shRNA

<400> SEQUENCE: 30
ggacgcuuuc cuucgggaaa ggucc                                         25

<210> SEQ ID NO 31
<211> LENGTH: 25
<212> TYPE: RNA
<213> ORGANISM: Artificial
<220> FEATURE:
<223> OTHER INFORMATION: shRNA

<400> SEQUENCE: 31
ggauuggucc uucgggacgc aaucc                                         25

<210> SEQ ID NO 32
<211> LENGTH: 25
<212> TYPE: RNA
<213> ORGANISM: Artificial
<220> FEATURE:
<223> OTHER INFORMATION: shRNA

<400> SEQUENCE: 32
ggauuucgcc cuucggggga aaucc                                         25

<210> SEQ ID NO 33
<211> LENGTH: 16
<212> TYPE: RNA
<213> ORGANISM: Artificial
<220> FEATURE:
<223> OTHER INFORMATION: shRNA

<400> SEQUENCE: 33
ggacgcuucg gcgucc                                                   16

<210> SEQ ID NO 34
<211> LENGTH: 20
```

```
<212> TYPE: RNA
<213> ORGANISM: Artificial
<220> FEATURE:
<223> OTHER INFORMATION: shRNA

<400> SEQUENCE: 34
ggacgugcuu cggcacgucc                                            20

<210> SEQ ID NO 35
<211> LENGTH: 22
<212> TYPE: RNA
<213> ORGANISM: Artificial
<220> FEATURE:
<223> OTHER INFORMATION: shRNA

<400> SEQUENCE: 35
ggauuucccu ucggggaaau cc                                         22

<210> SEQ ID NO 36
<211> LENGTH: 26
<212> TYPE: RNA
<213> ORGANISM: Artificial
<220> FEATURE:
<223> OTHER INFORMATION: shRNA

<400> SEQUENCE: 36
ggauuucgcg cuucggcgcg aaaucc                                     26

<210> SEQ ID NO 37
<211> LENGTH: 24
<212> TYPE: RNA
<213> ORGANISM: Artificial
<220> FEATURE:
<223> OTHER INFORMATION: shRNA

<400> SEQUENCE: 37
ggacguacgu uucgacguac gucc                                       24

<210> SEQ ID NO 38
<211> LENGTH: 28
<212> TYPE: RNA
<213> ORGANISM: Artificial
<220> FEATURE:
<223> OTHER INFORMATION: shRNA

<400> SEQUENCE: 38
ggacguacgu gcuucggcac guacgucc                                   28

<210> SEQ ID NO 39
<211> LENGTH: 32
<212> TYPE: RNA
<213> ORGANISM: Artificial
<220> FEATURE:
<223> OTHER INFORMATION: shRNA

<400> SEQUENCE: 39
ggacguacgu acgcuucggc guacguacgu cc                              32

<210> SEQ ID NO 40
<211> LENGTH: 44
<212> TYPE: RNA
<213> ORGANISM: Artificial
<220> FEATURE:
<223> OTHER INFORMATION: shRNA

<400> SEQUENCE: 40
```

```
ggacguacgu acguacgugc uucggcacgu acguacguac gucc      44

<210> SEQ ID NO 41
<211> LENGTH: 64
<212> TYPE: RNA
<213> ORGANISM: Artificial
<220> FEATURE:
<223> OTHER INFORMATION: shRNA

<400> SEQUENCE: 41
ggacguacgu acgugcacgu acguacgugc uucggcacgu acguacgugc acguacguac    60
gucc                                                                64

<210> SEQ ID NO 42
<211> LENGTH: 25
<212> TYPE: RNA
<213> ORGANISM: Artificial
<220> FEATURE:
<223> OTHER INFORMATION: shRNA

<400> SEQUENCE: 42
ggauuucaua cuucgguuga aaucc                                         25

<210> SEQ ID NO 43
<211> LENGTH: 25
<212> TYPE: RNA
<213> ORGANISM: Artificial
<220> FEATURE:
<223> OTHER INFORMATION: shRNA

<400> SEQUENCE: 43
ggauuucgcg cuucggccga aaucc                                         25

<210> SEQ ID NO 44
<211> LENGTH: 24
<212> TYPE: RNA
<213> ORGANISM: Artificial
<220> FEATURE:
<223> OTHER INFORMATION: shRNA

<400> SEQUENCE: 44
ggauuucccc uucgggggaa aucc                                          24

<210> SEQ ID NO 45
<211> LENGTH: 24
<212> TYPE: RNA
<213> ORGANISM: Artificial
<220> FEATURE:
<223> OTHER INFORMATION: shRNA

<400> SEQUENCE: 45
ggagggaaac uucgguuucc cucc                                          24

<210> SEQ ID NO 46
<211> LENGTH: 20
<212> TYPE: DNA
<213> ORGANISM: Artificial
<220> FEATURE:
<223> OTHER INFORMATION: Primer

<400> SEQUENCE: 46
ggagggaaac gaaactagcc                                               20

<210> SEQ ID NO 47
<211> LENGTH: 20
```

```
<212> TYPE: DNA
<213> ORGANISM: Artificial
<220> FEATURE:
<223> OTHER INFORMATION: Primer

<400> SEQUENCE: 47
gctcctcaaa ctctggcaac                                              20

<210> SEQ ID NO 48
<211> LENGTH: 20
<212> TYPE: DNA
<213> ORGANISM: Artificial
<220> FEATURE:
<223> OTHER INFORMATION: IFNB Primer Sense

<400> SEQUENCE: 48
ctctcctgtt gtgcttctcc                                              20

<210> SEQ ID NO 49
<211> LENGTH: 22
<212> TYPE: DNA
<213> ORGANISM: Artificial
<220> FEATURE:
<223> OTHER INFORMATION: IFNB Primer Antisense

<400> SEQUENCE: 49
gtcaaagttc atcctgtcct tg                                           22

<210> SEQ ID NO 50
<211> LENGTH: 20
<212> TYPE: DNA
<213> ORGANISM: Artificial
<220> FEATURE:
<223> OTHER INFORMATION: ACTB Primer Sense

<400> SEQUENCE: 50
tcgtgcgtga cattaaggag                                              20

<210> SEQ ID NO 51
<211> LENGTH: 20
<212> TYPE: DNA
<213> ORGANISM: Artificial
<220> FEATURE:
<223> OTHER INFORMATION: ACTB Primer Antisense

<400> SEQUENCE: 51
gtcaggcagc tcgtagctct                                              20

<210> SEQ ID NO 52
<211> LENGTH: 22
<212> TYPE: DNA
<213> ORGANISM: Artificial
<220> FEATURE:
<223> OTHER INFORMATION: DDX58 Primer Sense

<400> SEQUENCE: 52
gccattacac tgtgcttgga ga                                           22

<210> SEQ ID NO 53
<211> LENGTH: 22
<212> TYPE: DNA
<213> ORGANISM: Artificial
<220> FEATURE:
<223> OTHER INFORMATION: DDX58 Primer Antisense

<400> SEQUENCE: 53
```

```
ccagttgcaa tatcctccac ca                                          22

<210> SEQ ID NO 54
<211> LENGTH: 23
<212> TYPE: DNA
<213> ORGANISM: Artificial
<220> FEATURE:
<223> OTHER INFORMATION: RSAD2 Primer Sense

<400> SEQUENCE: 54
cacaaagaag tgtcctgctt ggt                                         23

<210> SEQ ID NO 55
<211> LENGTH: 26
<212> TYPE: DNA
<213> ORGANISM: Artificial
<220> FEATURE:
<223> OTHER INFORMATION: RSAD2 Primer Antisense

<400> SEQUENCE: 55
aagcgcatat attcatccag aataag                                      26
```

IMMUNOMODULATORY SMALL HAIRPIN RNA MOLECULES

CROSS-REFERENCE TO RELATED APPLICATION

This application makes reference to and claims the benefit of priority of the Singapore Patent Application No. 10201800434S filed on 17 Jan. 2018, the content of which is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention generally relates generally to structure guided RNA design to develop potent immune-modulatory RNA species that activate retinoic acid inducible gene I receptor (RIG-I), the thus obtained RNA molecules, compositions containing them and the uses and methods of use thereof.

BACKGROUND OF THE INVENTION

There is an increasing public health demand for immune-modulatory molecules with novel mechanisms of action that can be employed as antiviral products or as vaccine adjuvants. Such molecules, by targeting the host instead of the virus, can effectively block a broad spectrum of viral infections. Earlier and ongoing pharmaceutical drug development programs mostly target pathogens and their essential enzymes. Molecular targets that modulate host immune responses to infection have been largely ignored. A key advantage of targeting host molecules is the reduced sensitivity to virus adaptive mutations.

The retinoic acid inducible gene I (RIG-I) like receptors (RLRs) are an important class of pattern recognition receptors sensing viral RNA during infections. RLRs consist of three members Retinoic Acid-Inducible Gene 1 (RIG-I), Melanoma Differentiation Associated Gene 5 (MDA5) and Laboratory of Genetics and Physiology 2 (LGP2). They play an essential role in sensing viral infection and initiating interferon mediated antiviral immune response. RLRs are a general class of pattern recognition receptors (PRRs) which detects viral RNA in cytoplasm of infected cells and triggers the innate immune response by the production of pro-inflammatory cytokine and type I interferon. RLRs have the capability to differentiate self and non-self RNAs by certain motifs representing the hallmark of viral replication.

RIG-I is able to detect RNA generated by viruses due to the presence of the triphosphorylated moiety on RNA strands of replicating viruses whereas the endogenous RNA is further processed to contain a 5' cap (Hornung et al. (2006), Science 314(5801):994-7). Partial complementary terminal sequence present in ssRNA viruses replication origin folded to form panhandle structure are also recognized by RIG-I (Schlee et al. (2009), Immunity 31(1):25-34). Besides that, defective interfering RNA genome formed snap back based paired structures are also recognized by RIG-I (Strahle et al. (2006), Virology 351(1):101-11). In addition to 5' triphosphate ended RNA, RIG-I also recognizes and binds to 5' diphosphorylated RNA and also Cap 0 RNA (Devarkar et al. (2016) Proc. Natl. Acad. Sci. USA 113(3):596-601; Goubau et al. (2014), Nature 514(7522): 372-5).

The core of RLRs is a specialized DExD/H-box RNA helicase which consists of Hel1, Hel2 and an insertion domain Hel2i, to recognize double stranded RNA backbone. The C-terminal domain (CTD) is a $Zn^{2+}$ containing RNA binding domain. Together, HEL-CTD forms the RNA sensing module, responsible to detect the chemical and structural features of the captured RNA species, in order to determine if RLR activation is granted (Kohlway et al. (2013), EMBO Rep 14(9):772-9; Luo et al. (2011), Cell 147(2):409-22; Schlee (2013), Immunobiology 218: 1322-1335). The N-terminal tandem caspase activation and recruitment domains (CARDs) of RIG-I and MDA5 are the signaling domains which are responsible for activating downstream signaling by interacting and oligomerizing the adaptor protein MAVS (mitochondria antiviral signaling protein) on the mitochondria outer membrane (Kawai et al. (2005), Nat Immunol 6: 981-988; Meylan et al. (2005) Nature 437: 1167-1172; Peisley et al. (2014) Nature 509: 110-114; Seth et al. (2005) Cell 122: 669-682; Wu et al. (2014), Mol Cell 55: 511-523; Xu et al. (2005) Mol Cell 19: 727-740). RIG-I and MDA5 recognize different but overlapping subsets of RNA viruses. This is related to their RNA recognition preference. Whereas RIG-I prefers short, duplex RNA with a 5'end triphosphate, MDA5 cooperatively binds to long duplex RNAs with no requirements on the RNA preference in 5'end character ends (Kato et al. (2006), Nature 441: 101-105; Loo & Gale (2011), Immunity 34: 680-692; Wu & Chen (2014), Annu Rev Immunol 32: 461-488; Zheng et al. (2015), Nucleic Acids Res 43: 1216-1230; Kowalinski et al. (2011), Cell 147: 423-435; Luo et al. (2011), Cell 147: 409-422, Wu et al. (2013), Cell 152: 276-289).

In the cytoplasm, RIG-I exists in the autorepressed conformation with CARDs interacting with the HEL2i domain during the normal state of the cell (Kowalinski et al., supra; Zheng et al, supra). When it encounters the pathogenic RNA upon viral infection, protein conformational rearrangement coupled with ATP hydrolysis occurs. As the consequence, the N terminal CARDs will be exposed to allow interaction with MAVS (Wu & Chen, supra; Wu et al., supra). Subsequently, MAVS will activate the downstream signaling via IRF3, IRF7 and NFκB transcription factor to trigger the production of type I interferon (IFN-I) and pro-inflammatory cytokines (Seth et al., supra; Peisley et al., supra; Hiscott et al. (2006), Trends Mol Med 12: 53-56; Iwanaszko & Kimmel (2015), BMC genomics 16: 307; Ramos & Gale (2011), Curr Opin Virol 1: 167-176). The CTD of RIG-I recognizes and is activated by 5' triphosphorylated RNA commonly generated during viral replication processes (Hornung et al. (2006), Science 314: 994-997). Besides 5' triphosphorylated RNA, RIG-I also recognizes terminal 5'diphosphate and cap0 moiety as non-self RNA (Devarkar et al. (2016) Proc. Natl. Acad. Sci. USA 113(3):596-601; Goubau et al. (2014), Nature 514(7522):372-5). Recent studies revealed that RIG-I have a higher preference for poly U/UC tract and AU-rich RNA (Runge et al. (2014), PLoS pathogens 10: e1004081; Schnell et al. (2012), PLoS Pathog 8: e1002839). Furthermore, short RNA hairpins with the minimal length of 10-12 base pairs are able to bind to and activate RIG-I (Kohlway et al., supra; Zheng et al., supra). It was also reported that short RNA duplexes elicit RIG-I mediated apoptosis in a cell type- and length-dependent manner (Ishibahi et al. (2011), Sci. Signal. 4 (198), ra74).

Given the advanced knowledge of the innate immune activation via RIG-I, it is attractive to develop broad spectrum immune modulators for antiviral and anticancer therapeutic agents targeting RIG-I (Elion & Cook (2018), Oncotarget, 2018, Vol. 9, (No. 48), pp: 29007-29017; Elion et al.

(2019), Cancer Research, Author Manuscript Published Online First on Sep. 17, 2018; DOI: 10.1158/0008-5472; Duewell et al. (2014), Cell Death and Differentiation 21, 1825-1837). Many immune modulators have been reported to be synthetic PAMPs (pathogen associated molecular patterns) which target RIG-I mediated IFN-I production signaling pathway (Yong & Luo (2018), *Front Immunol* 9: 1379). Among the reported active agents, 5' triphosphorylated short double-stranded RNA are the most potent RIG-I-specific ligands (Goubau et al., supra; Hornung et al., supra; Kato et al. (2011), *Nature* 441: 101-105; Schmidt et al. (2009), *Proc Natl Acad Sci U S A* 106: 12067-12072). In cell-based assays and animal studies, 5'pppRNAs treatment activates RIG-I mediated antiviral defense signaling pathways and protects cells from infections of multiple viruses such as influenza, vesicular stomatitis, dengue and chikungunya viruses (Chiang et al. (2015), J Virol 89(15):8011-25; Lee et al. (2018), Nucleic Acids Res. 46(4):1635-1647). There has been recently pioneered research demonstrating the in vivo activity of these short RNA species (Linehan et al. (2018), *Science advances* 4: e1701854), with the best short stem-loop RNAs (SLR) being 10 and 14 bps long with a stable tetraloop at one end and 5'ppp blunt base pairs at the other. Comparing to polyIC, which are synthetic long duplex RNAs of heterogeneous length known to broadly activate TLR3, MDA5 and RIG-I, RIG-I-specific ligands such as SLRs are more IFN-I specific and may activate novel signaling pathways.

Accordingly, beside their potential as a vaccine adjuvants and antiviral agents, immune-modulatory (immune-stimulatory) RNA can be a powerful innate immune activator to be used in conjunction with cancer immunotherapies (Moore et al. (2016), Cancer Immunol Res 4, 1061-1071, doi:10.1158/2326-6066), or they could have anti-tumor activity on their own, similar to other therapies targeting cellular nucleic-acid sensors (Junt & Barchet (2015), Nat Rev Immunol 15, 529-544).

Dengue virus (DENV) is an arbovirus that is transmitted to humans through the bite of an infected *Aedes* mosquito. DENV is part of the Flaviridae family and is a member of the *Flavivirus* genus. This family of viruses comprises other viruses that are known to pose health threats to the human population globally, including yellow fever virus (YFV), West Nile virus (WNV) and Japanese encephalitis virus (JEV). DENV is an enveloped virus that contains a single-stranded, positive-sense RNA genome. This viral genome encodes a large polyprotein, which is processes by viral and host proteases into three structural proteins (Capsid, prM and Envelope protein) and seven non-structural proteins (NS1, NS2A, NS2B, NS3, NS4A, NS4B and NS5). The transmission of DENV involves the transfer of virus from the saliva of the biting mosquito to the dermal layer of human skin. The outermost, epidermal layer contains keratinocytes and Langerhans cells (LCs), a skin resident antigen-presenting cell (APC) that is involved in detecting pathogens that penetrate the skin barrier. The dermal layer, which is located below the epidermal layer, consists of fibroblasts and immune cells including macrophages, T cells and dendritic cells, and is innervated with blood and lymphatic vessels that enable immune cell migration to draining lymph nodes. Antigen-presenting cells (APCs) are primary host cells for DENV infection. Professional APCs in the skin are particularly important in the establishment of infection due to their location at the point of virus entry into the host. Upon DENV infection, APCs are activated by the viral RNA binding to RIG-I and MDA5 in the cytoplasm of these cells.

Therefore, specific and potent RNA species which can modulate RIG-I mediated immune response would be valuable towards developing new therapeutic agent and useful research tools.

SUMMARY OF THE INVENTION

The present invention meets this need by providing small hairpin RNA (shRNA) molecules that can modulate RIG-I mediated immune responses and thus have potential use as therapeutic agents, specifically as adjuvants and antivirals, as well as research tools.

In a first aspect, the present invention is thus directed to a small hairpin RNA (shRNA) molecule having the structure, in 5' to 3' orientation, $X_1$-L-$X_2$, wherein $X_1$ and $X_2$ are each nucleotide sequences of 8 to 30 nucleotides in length having sufficient complementarity to one another to form a double-stranded stem structure;

L is a nucleotide sequence forming a loop region;

the first nucleotide positioned at the 5' terminal end of $X_1$ is designated as n1 and is di- or triphosphorylated, and the last nucleotide at the 3' terminal end of $X_2$ is designated nx, wherein x is an integer of 25 to 65;

the shRNA molecule comprises a nucleotide insertion in $X_1$ in position n7 or higher or in $X_2$ at position nx−6 or lower that remains unpaired in the double-stranded stem structure and creates a kink.

In these shRNA molecules, L may be a nucleotide sequence of 1 to 10 nucleotides in length, preferably 2 to 4 nucleotides in length.

In various embodiments of the shRNA molecules, the nucleotide at the 5' terminal end, i.e. the first nucleotide of the $X_1$ arm, is triphosphorylated.

In various embodiments, the shRNA molecule is blunt-ended, i.e. does not comprise a 5' or 3' overhang. It is further preferred that the 5'- and 3'-terminal nucleotides base pair with one another so that there are no unpaired nucleotides at the termini of the molecule.

In various embodiments, $X_1$ and $X_2$ are each nucleotide sequences of 10 to 25 nucleotides in length, preferably of 10, 11, 20, 21, 30 or 31 or 10-20 nucleotides in length, more preferably of 10 or 11 nucleotides in length. It may be preferred that $X_1$ and $X_2$ are, not counting the nucleotide insertion creating the kink, of the same length and are 10, 20 or 30 nucleotides in length, preferably 10.

In various embodiments, $X_1$ and $X_2$ are, with the exception of the nucleotide insertion creating the kink, fully complementary to one another.

The nucleotide insertion may be a nucleotide insertion of 1-2 nucleotides, preferably of a single nucleotide. In some embodiments, the nucleotide insertion is a nucleotide insertion in $X_1$. The nucleotide insertion may be in a position selected from the positions ranging from n7 to the position directly upstream of the 3' terminal position of $X_1$ (penultimate position of $X_1$) or from the positions ranging from the second position (directly downstream of the 5' terminal position) of $X_2$ to nx−6. In various embodiments thereof, the nucleotide insertion is in a position selected from the positions ranging from n9 to the position 2 or 3 nucleotides upstream of the first nucleotide of the loop region or from the position 2 or 3 nucleotides downstream of the last nucleotide of the loop region to nx−8. The nucleotide insertion may preferably be in the $X_1$ sequence, preferably at position n9.

In various embodiments, the nucleotide insertion is a purine or pyrimidine nucleotide, preferably a purine nucleotide selected from G and A.

The loop region L may comprise or consist of the sequence UUCG.

In various embodiments, $X_1$ comprises or consists of a nucleotide sequence selected from the group consisting of:

rrrnnyyyryy; (SEQ ID NO: 1)

ssvvwwwssrss; (SEQ ID NO: 2)

ggannnnnnnn; (SEQ ID NO: 3)

ggannnnnncc; (SEQ ID NO: 4)

ggannuncncc; (SEQ ID NO: 5)

ggawwuscncc; (SEQ ID NO: 6)

ggauuuccrcc; (SEQ ID NO: 7)

ggauuuccacc; (SEQ ID NO: 8)
or ggauuuccgcc, (SEQ ID NO: 9)

wherein r is g or a, y is u or c, w is a or u, s is g or c and n is a, g, u or c.

In various embodiments, $X_2$ comprises or consists of a nucleotide sequence selected from the group consisting of:

rrrrrnnyyy; (SEQ ID NO: 10)

sssswwwwss; (SEQ ID NO: 11)

nnnnnnnucc; (SEQ ID NO: 12)

ggnnnnnucc; (SEQ ID NO: 13)

gggnannucc; (SEQ ID NO: 14)

gggwawwucc; (SEQ ID NO: 15)

ggggaaaucc, (SEQ ID NO: 16)

wherein r is g or a, y is u or c, w is a or u, s is g or c and n is a, g, u or c.

In various embodiments, the shRNA molecule comprises or consists of a nucleotide sequence selected from the group consisting of:

rrrnnyyyryyuucgrrrrrnnyyy; (SEQ ID NO: 17)

sswwwwssrssuucgsssswwwwss; (SEQ ID NO: 18)

ggannnnnnnnuucgnnnnnnnucc; (SEQ ID NO: 19)

ggannnnnnccuucgggnnnnnucc; (SEQ ID NO: 20)

ggannuncnccuucggggnannucc; (SEQ ID NO: 21)

ggawwuscnccuucggggwawwucc; (SEQ ID NO: 22)

ggauuuccnccuucggggaaaucc; (SEQ ID NO: 23)

ggauuuccrccuucggggaaaucc; (SEQ ID NO: 24)

ggauuuccaccuucggggaaaucc; (SEQ ID NO: 25)
or ggauuuccgccuucggggaaaucc, (SEQ ID NO: 26)

wherein r is g or a, y is u or c, w is a or u, s is g or c and n is a, g, u or c.

The shRNA molecules preferably bind specifically to human retinoic acid-inducible gene 1 receptor (RIG-I).

In another aspect, the invention relates to compositions comprising at least one shRNA molecule according to the invention. Such compositions may comprise one species of such shRNA or may comprise a plurality of different shRNA molecules according to the invention.

The composition can be a pharmaceutical composition, for example an immunostimulatory or antiviral or anti-cancer composition. The immunostimulatory composition may be a vaccine composition further comprising a vaccine, wherein the shRNA molecule(s) are the adjuvant. If the composition is an antiviral composition, it can further comprise an additional active antiviral agent. If the composition is an anti-cancer composition, it can further comprise an additional active anti-cancer agent. The compositions of the invention can, independently of their use, comprise one or more excipients that preferably are pharmaceutically acceptable.

The invention further encompasses the use of the shRNA molecules of the invention as an adjuvant or as an antiviral agent or as an anti-cancer agent. Also contemplated is the shRNA molecule of the invention or composition of the invention for use in a method for stimulating the immune system or treating/preventing a viral infection or treating or preventing cancer in a subject in need thereof. The shRNA molecules can act as adjuvants for the active agent or can be used for their own antiviral or anti-cancer activity.

Another aspect of the invention features a method for stimulating the immune system in a subject in need thereof, the method comprising administering an effective amount of the shRNA molecule according to the invention or of the composition of the invention to said subject. Another method of the invention is for treating or preventing a viral infection in a subject in need thereof, the method comprising administering an effective amount of the shRNA molecule according to the invention or of the composition of the invention to said subject. A still further method of the invention is for treating or preventing cancer in a subject in need thereof, the method comprising administering an effective amount of the shRNA molecule according to the invention or of the composition of the invention to said subject.

In a still further aspect, the invention is directed to a method for modifying a small hairpin RNA (shRNA) molecule having the structure, in 5' to 3' orientation, $X_1$-L-$X_2$, wherein $X_1$ and $X_2$ are each nucleotide sequences of 8 to 30 nucleotides in length having sufficient complementarity to one another to form a double-stranded stem structure;

L is a nucleotide sequence forming a loop region;

the first nucleotide positioned at the 5' terminal end of $X_1$ is designated as n1 and the last nucleotide at the 3' terminal end of $X_2$ is designated nx, wherein x is an integer of 25 to 65;

the method comprising introducing a nucleotide insertion into $X_1$ in position n7 or higher or in $X_2$ at position nx−6 or lower that remains unpaired in the double-stranded stem structure to create a kink.

In the following the invention will be described in greater detail by reference to the accompanying drawings and examples.

BRIEF DESCRIPTION OF THE DRAWINGS

The invention will be better understood with reference to the detailed description when considered in conjunction with the non-limiting examples and the accompanying drawings.

DETAILED DESCRIPTION OF THE INVENTION

Figure 1:
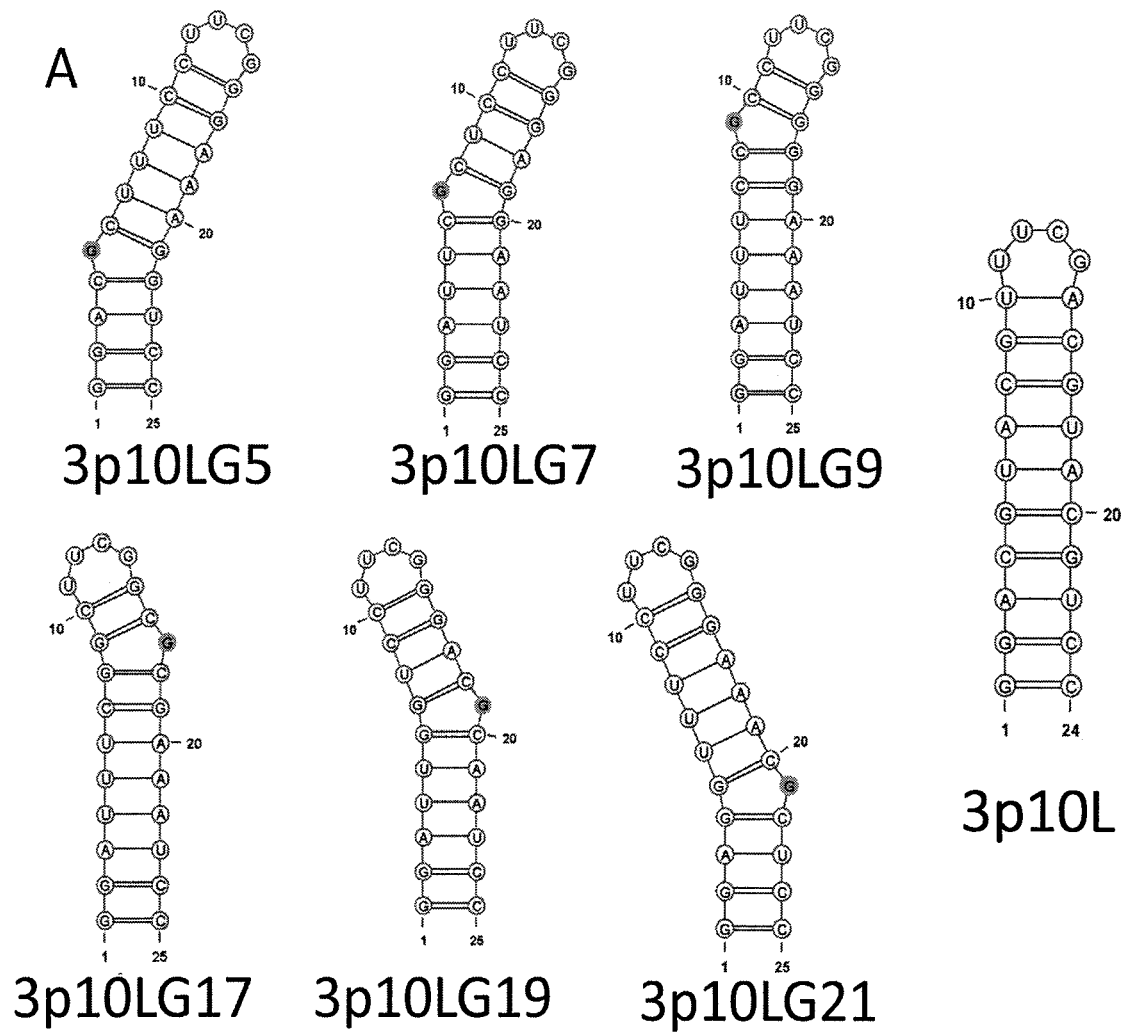
FIG. 1. Insertion of guanosine along the 3p10L RNA hairpin backbone (SEQ ID NO:37) changed the RIG-I enzymatic and cellular activities differently. (A) The design of hairpin RNA introducing bulges/kinks along the stem region of RNA. (B) Cell based assay of different RNA in HEK-Lucia™ RIG-I and HEK-Lucia™ null. RNA was transfected at a fix concentration of 100 nM and luminescence was measured 24 hours post-transfection. Results are measured in triplicate and presented as RLU. (C) The ATPase activity of RNA with the highest cell based assay activity (3p10LG9; SEQ ID NO:26) and lowest activity (3p10LG5; SEQ ID NO:30) in comparison to the parental strand of RNA (3p10L; SEQ ID NO:37). The data were fitted to the Michaelis-Menten equation and the $K_{m,ATP}$ and $K_{cat,ATP}$ was determine with saturating amount of RNA to hsRIG-I.
Figure 1:
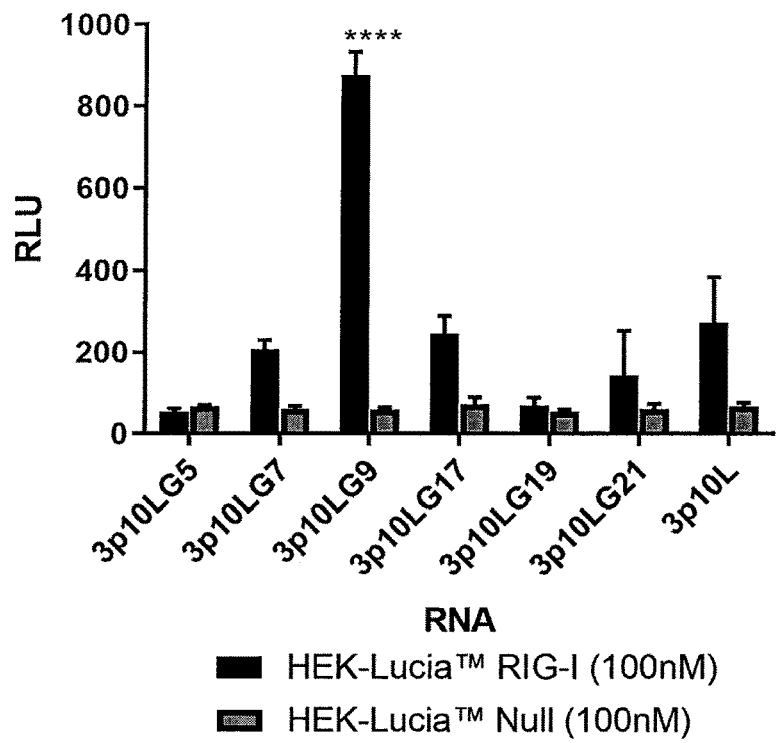
Figure 1:
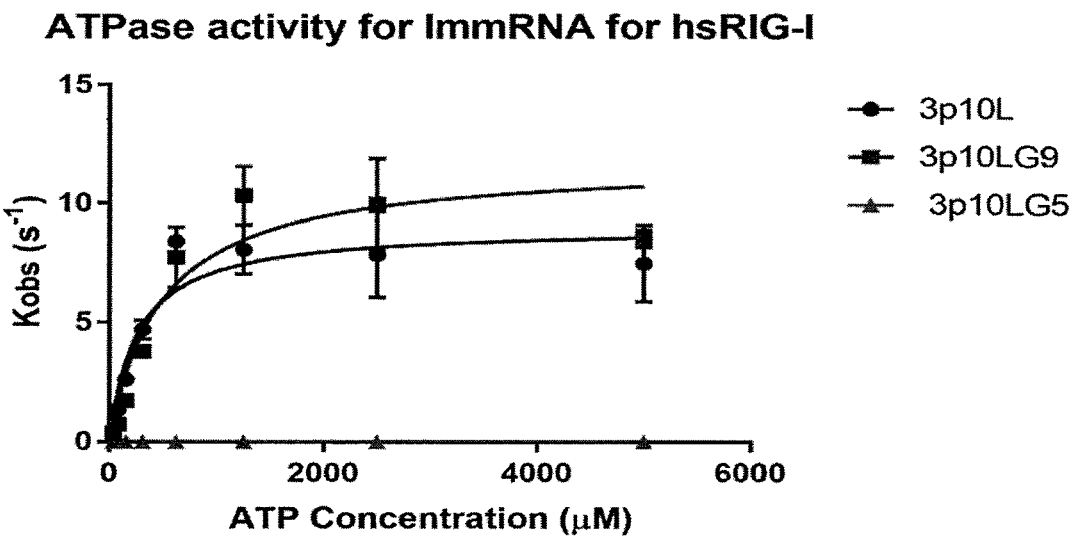

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. The singular terms "a", "an" and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

The present invention is based on the efforts of the inventors to dissect the effect of structural modification of short 5' triphophorylated RNA on the activation of RIG-I signaling. During these studies, it was found that introduction of a mismatch in a known short hairpin RNA, 3p10L (SEQ ID NO:37), to create an insertion along the RNA stem significantly influences biological activity. The RNAs studied were generally designed as hairpin RNA terminated at one end with a thermodynamically stable UUCG tetraloop to ensure RIG-I binds in a single orientation and therefore, the kink in the upper and lower strand could be studied effectively.

Based on the crystallographic data obtained previously, the CTD and HEL1 of RIG-I were shown to form a rigid hold on the first 4 nucleotides from the 5' and 3' end of the RNA molecule, whereas the HEL2i domain interacts with the stem region up to the base 9 from the $5^{th}$ nucleotide of the upper strand onwards (PDB id: 4AY2, 5F9H, 3ZD6, 3ZD7 and 5E3H). The HEL2i domain was observed to scan along the stem region of the RNA. The relative position of HEL2i was shown to have an effect on the RIG-I activation because the CARDs domain interacts with the HEL2i domain in the inactive conformation. It was observed that the insertion created on the stem of the RNAs has an allosteric effect on the relative movement of the domain which also effect the robustness of type I interferon activation via RIG-I. In particular, the insertion of purines at the position 9 of the RNA stem triggers higher type I interferon responses. Conformational dynamics studies via HDX-MS proved that the binding of 3p10LG9 (SEQ ID NO:26) to RIG-I increased the CARDs exposure as compared to the known 3p10L RNA (SEQ ID NO:37). These findings highlight that the structural modification of short hairpin RNA can enhance the type I interferon activation via RIG-I.

The cell based assay showed that the insertion introduced at position 9 of the upper strand (3p10LG9) enhances the type I interferon activation. Based on the model of 3p10LG9, the addition of the insertion present in 3p10LG9 interacts with the back surface of the helicase 2i domain of the RIG-I. In the crystal structure captured with many different RNA ligands and ATP analogues, HEL2i domain is the most mobile domain and samples the RNA strand. Without wishing to be bound to any particular theory, it is hypothesized that the kink in position 9 could possibly lock the α-helical bundles in HEL2i in the extended conformation and in a position that expels CARDs domain resting on the HEL2i domain. Based on the proposed mechanism of ATPase activity and signaling, RIG-I locked in an active conformation for a longer duration would improve the ability to sustain type I Interferon production.

To further validate this hypothesis, HDX-MS was carried out to compare region within RIG-I that undergoes faster hydrogen deuterium exchange. In HDX-MS the more dynamic region will undergo a higher deuterium incorporation whereas the rigid region will have a lower deuterium incorporation. Several regions of RIG-I protein with higher deuterium incorporation were observed when bound to 3p10LG9 as compared to 3p10L. One of the regions that display a higher deuterium exchanges is the latch peptide (Y103-114) of the CARD domain, which, in the inactive conformation is bound to RIG-I HEL2i domain. Hence, the when RIG-I is bound to 3p10LG9, the CARDs are more exposed and less protected from the deuterium incorporation as compared to RIG-I bound to 3p10L. Another region that displayed a high protection from deuterium incorporation when bound to 3p10LG9 is the motif Ia and motif Ic of the helicase 1 domain. This indicates that the 3p10LG9 is more tightly bound to the HEL1 domain as compared to 3p10L. Besides, HEL1 domain, the capping loop of CTD and the CTD binding site to 3p10LG9 also displayed a lower hydrogen-deuterium exchange indicating a tighter binding of 3p10LG9 as compared to 3p10L. Although HEL1 and CTD domain were not directly interacting with CARDs domain, the overall tighter binding HEL1 and CTD to the RNA indicates the overall compaction of helicase domain. From the previous biochemical and structural studies, the compaction of helicase in the event of ATP binding causes the CTD and the CARDs domain to come into close proximity and the clash of the domain releases the CARDs for downstream signaling events.

Without wishing to be bound to any particular theory, it is assumed from the obtained data that the more compact RIG-I helicase domain's interaction with the RNA due to tighter binding with 3p10LG9 would lead to a more sustained release of CARDs domain.

The kink created by the insertion of G at the position 5 (3p10LG5) of the hairpin RNA abolishes the activation of type I interferon. Based on the model of 3p10LG5, the kinked introduced to 3p10LG5 interacts with the HEL1 domain. The HEL1 is mainly involved in RNA binding. The region in which the kink interacts with the HEL1 domain is with the motif IIa. Based on the structures of SF2 helicases, the motif IIa is shown to interact with RNA and display a structural conservation within the DEAD-box family member. This motif IIa could be an important motif to form a stable interaction with RNA. As observed before, the mutation of a residue Q380 to Proline, a key residue in the motif IIa in hsRIG-I, abolished the type I interferon activation (Louber et al. (2015), *BMC biology* 13: 54). The kink introduced at position 5 of the upper strand of hairpin RNA could potentially perturb the RNA binding and the grip of HEL1 domain on the RNA that is required for RIG-I activation. The ability of RIG-I to discriminate nucleotides and the preference towards some RNA with stretches of uracil had been reported previously (Runge et al. (2014), *PLoS pathogens* 10: e1004081; Schnell et al. (2012), *PLoS Pathog* 8: e1002839). For the different nucleotides at the kink position 9, it is more likely that the presence of bulkier purine is required for the HEL2i domain perturbation as compared the smaller side chain of pyrimidine.

The inventors thus demonstrated that the structural modification of the stem RNA could alter the robustness of type I interferon activation. It was found that unlike the introduction of guanosine insertion at position 5 of the stem which abolishes the type I interferon activation, the purine based insertion at the position 9 of the stem of the RNA enhances the RIG-I activation and type I interferon signaling.

Based on previous work to determine the minimal RNA ligand required for interferon activation, the inventors made various modifications to the original sequence and tested the ability of these newly designed immune-modulating RNAs (immRNAs) to activate RIG-I-mediated innate immune response in host cells. It was found that newly designed candidate immRNAs have greater potency in activating type I interferon response compared to the parental construct and were used to study their protective effects against DENV infection in both human cell lines as well as in a human skin cell assay model to assess their potential as prophylactic and therapeutic molecules.

The invention thus relates to newly discovered small hairpin RNA (shRNA) molecules having the structure, in 5' to 3' orientation, $X_1$-L-$X_2$.

"Small hairpin RNA" or "shRNA", as interchangeably used herein, relates to small hairpin ribonucleic acid molecules that are polynucleotides having a sugar phosphate backbone comprising ribose units and comprising the nucleobases adenine, guanine, uracil and cytosine. The respective nucleotide units are, according to IUPAC nomenclature, designated as A, G, U and C herein. Furthermore, in accordance with IUPAC nomenclature, the symbols W and S are used for weak interaction (2H bonds), i.e. A/U, and strong interactions (3H bonds), i.e. G/C, and the symbols Y and R for nucleotides with pyrimidine (C and U) and purine (G and A) nucleobases, respectively.

The RNA molecules described herein typically comprise up to 80 nucleotides, preferably 21 to 65 nucleotides, more preferably about 25 nucleotides. Although RNA is typically single-stranded, the self-complementarity of the 5' and 3'-ends of the molecule leads to the formation of secondary structures, conventionally termed as "hairpin structures" that consist of a stem region of two complementary arms, the 5' and 3' arm, that are typically connected by a loop structure.

All nucleotide sequences disclosed herein are, if not indicated otherwise, always shown in the 5' to 3' orientation. Similarly, if reference is made to a position of a nucleotide within the molecule, said position is always determined by counting the nucleotides starting from the 5' end, the first nucleotide on the 5' end being in position 1.

While in the following reference is generally made to RNA molecules and all specific molecules disclosed are unmodified with the exception that all are di- or triphosphorylated on the 5' end, it is understood that modified derivatives of these molecules may be provided in which, for example, the sugar phosphate backbone is modified, for example to improve metabolic stability. Exemplary modifications include, without limitation, phosphorothioate usage instead of the native backbone or 2'-Fluoro modifications. Accordingly, all embodiments disclosed herein in relation to unmodified RNA molecules may be similarly practiced with modified RNA molecules as long as the essential structural determinants described herein are retained.

The shRNA molecules of the invention are diphosphorylated or triphosphorylated on the 5' end. This means that the monophosphate group on the 5' carbon of the ribose unit of the 5' terminal nucleotide is replaced by a di- or triphosphate group. Accordingly, all molecules disclosed herein with respect to their nucleotide sequence are di- or triphosphorylated on their 5' end without this being specifically indicated. Triphosphorylated molecules are particularly preferred.

In the RNA molecules of the invention, $X_1$ and $X_2$ are each nucleotide sequences of 8 to 30 nucleotides in length having sufficient complementarity to one another to form a double-stranded stem structure. When reference is made to "complementarity", typical Watson-Crick base pairing complementarity is meant, i.e. A is complementary to U and G is complementary to C. Complementarity may be given as a numerical value in %, calculated by dividing the paired nucleotides of a given single-stranded sequence stretch by the total number of nucleotides in this stretch×100. For example, if 9 nucleotides of a 10 nucleotide long sequence stretch can be paired by Watson-Crick base pairing, complementarity would be 90%. In accordance therewith, "full complementarity" means that all nucleotides of a given sequence stretch can pair by Watson-Crick base pairing with the respective complementary sequence. In relation to the molecules of the present invention, this may mean that all nucleotides of $X_1$ can base-pair with all nucleotides of $X_2$ and vice versa.

The $X_1$ region is the 5' terminal sequence of the shRNA molecule and thus also designated 5' arm herein. Similarly, as the $X_2$ region is the 3' terminal part, it is also termed 3' arm. Both sequences are covalently linked to each other by a loop region L. The loop region is a nucleotide sequence that forms a loop region that comprises 1 or more unpaired nucleotides that link the paired sequence stretches of $X_1$ and $X_2$. The loop may be 1 to 10 nucleotides in length, for example 2 to 8, 2 to 6, 3 to 5, 2 to 4 or 3 or 4 nucleotides in length. In various embodiments, the loop region L of the molecules of the invention comprises or consists of 4 nucleotides of the sequence YYYR, WWSS, UYYG, YUCR, UUSS, WWCG, UUCS, UUCR, YYCG, YUCG, WUCG or UUCG.

According to conventional nomenclature, as defined above, the first nucleotide positioned at the 5' terminal end of $X_1$ is designated as n1 and the last nucleotide at the 3' terminal end of $X_2$ is designated nx, with x being an integer indicating the total number of nucleotides in the RNA molecule. Typically, x is an integer of 25 to 65. Accordingly, n1 is the 5' terminal nucleotide and nx is the 3' terminal nucleotide. Following this nomenclature, n9 indicates the nucleotide at position 9 counted from the 5' end and nx-1 (x minus 1) indicates the penultimate nucleotide, i.e. the nucleotide upstream of the 3' terminal nucleotide nx. "Upstream", as used herein, refers to located in the 5' direction relative to a reference nucleotide, "downstream", as used herein, means located in the 3' direction relative to the reference point.

The shRNA molecules of the invention are characterized in that they comprise a nucleotide insertion in $X_1$ in position n7 or higher or in $X_2$ at position nx-6 or lower that remains unpaired in the double-stranded stem structure and creates a kink. "n7 or higher" means in position 7 counting from the 5' end or any position downstream thereof (i.e. in the 3' direction), including position 8, 9, 10, 11, etc. "nx-6 or lower" thus means in position x-6 (x minus 6), i.e. 6 positions upstream of the 3' terminal nucleotide. In an RNA molecule of 25 nucleotides in length, position nx-6 would thus be position n(25-6)=n19. The term "kink", as used herein, describes the distortion ("bulge") in the stem structure created by unpaired nucleotides on only one strand of the otherwise double-stranded stem structure.

In various embodiments, the shRNA molecules of the invention are blunt ended, i.e. $X_1$ and $X_2$ are, not counting the insertion creating the kink, of the same length, with the 5' and 3' terminal nucleotides of the molecule preferably hybridizing to each other by Watson-Crick base-pairing, such that the double-stranded stem structure includes both terminal nucleotides.

In various embodiments, $X_1$ and $X_2$ are each nucleotide sequences of 10 to 25 nucleotides in length, preferably of 10, 11, 20, 21, 30 or 31 or 10-20 nucleotides in length, more preferably of 10 or 11 nucleotides in length. It is generally preferred that X1 and X2 differ in length only in one nucleotide, which is the nucleotide inserted to create the kink in the structure. It has been found that biological activity appears to be highest for stem regions with lengths that 10 nucleotides in length or are multiples of 10 nucleotides, i.e. 10, 20, 30, etc, basepairs in length. Preferred are small RNA molecules that have a double-stranded stem region of 10 basepairs in length.

Particularly preferred are shRNA molecules, wherein $X_1$ and $X_2$ are, with the exception of the nucleotide insertion creating the kink, fully complementary to one another.

While the nucleotide insertion creating the kink may in principle have any length, it is preferred that it is a short nucleotide insertion of only up to 5, preferably up to 3, more preferably 1 or 2, most preferably only one nucleotide in length. While the insertion can be made up of any nucleotide, it is preferred that the insertion consists of purine nucleotides, i.e. A or G. In various embodiments, it can be preferred that the insertion is a single nucleotide selected from A and G, with in some of those embodiments A being even more preferably due to higher activity.

It has been found that insertions into the 5' arm, i.e. the $X_1$ sequence, appear to be generally more effective when it comes to modulating the biological activity of the shRNA. It is thus preferred that the insertion is in the $X_1$ sequence.

Furthermore, as also discussed above, it has been found that the position of the insertion significantly influences activity. Preferred is an insertion into the $X_1$ sequence in position n7 or higher up to one nucleotide before the 3' end of the $X_1$ sequence, i.e. the nucleotide upstream of the last paired nucleotide before the loop region starts (penultimate nucleotide of the $X_1$ sequence). While insertions in position 7 and 8 can be functional, it was found that biological activity is significantly increased if the insertion is in position 9 or higher. Preferred positions are position 9 and the positions between position 9 and the position 2 or 3, preferably 3, nucleotides upstream of the first loop nucleotide. In a molecule in which the 5' arm is 11 nucleotides long, this would mean that position 9 is particularly preferred, as it is at least positions downstream from the 5' terminus and at the same time 3 positions upstream of the first loop nucleotide.

In alternative embodiments, it may also be possible to position the insertion in the 3' arm. In such embodiments, the insertion may be in the second nucleotide of the $X_2$ sequence, i.e. the nucleotide directly downstream of the first paired nucleotide of the $X_2$ sequence, or any following position up to position nx−6, i.e. 7 positions upstream from the 3' end of the $X_2$ sequence. Such positions include, nx−7, nx−8, and nx−9.

In various embodiments, $X_1$ may comprise, consist essentially of or consist of a nucleotide sequence selected from the group consisting of:

rrrnnyyyryy;  (SEQ ID NO: 1)

sswwwwssrss;  (SEQ ID NO: 2)

ggannnnnnnn;  (SEQ ID NO: 3)

ggannnnnncc;  (SEQ ID NO: 4)

ggannuncncc;  (SEQ ID NO: 5)

ggavvwuscncc;  (SEQ ID NO: 6)

ggauuuccrcc;  (SEQ ID NO: 7)

ggauuuccacc;  (SEQ ID NO: 8)
or ggauuuccgcc,  (SEQ ID NO: 9)

wherein r is g or a, y is u or c, w is a or u, s is g or c and n is a, g, u or c. In these sequences, the bold nucleotide preferably is the insertion, i.e. is unpaired. In all exemplary $X_1$ sequences disclosed herein, the inserted, i.e. unpaired nucleotide is preferably at position 9. It is preferred that in such embodiments the $X_2$ sequence is, with the exception of the inserted nucleotide, the full complement of this sequence.

Accordingly, in various embodiments, the $X_2$ sequence comprises, consists essentially of or consists of a nucleotide sequence selected from the group consisting of:

rrrrrnnyyy;  (SEQ ID NO: 10)

sssswwwwss;  (SEQ ID NO: 11)

nnnnnnnucc;  (SEQ ID NO: 12)

ggnnnnnucc;  (SEQ ID NO: 13)

gggnannucc;  (SEQ ID NO: 14)

gggwawwucc;  (SEQ ID NO: 15)

ggggaaaucc,  (SEQ ID NO: 16)

wherein r is g or a, y is u or c, w is a or u, s is g or c and n is a, g, u or c. In these embodiments, $X_2$ does preferably not include the nucleotide insertion, the insertion thus being position in the 5' arm. Also in these embodiments, it is preferred that the $X_1$ sequence is, with the exception of the inserted nucleotide, the full complement of this sequence.

Together with the preferred loop sequences, the shRNA molecules of the invention preferably comprise, consist essentially of or consist of a nucleotide sequence selected from the group consisting of:

rrrnnyyyryyuucgrrrrrnnyyy;  (SEQ ID NO: 17)

sswwwwssrssuucgsssswwwwss;  (SEQ ID NO: 18)

ggannnnnnnnuucgnnnnnnnnucc;  (SEQ ID NO: 19)

ggannnnnccuucgggnnnnnucc;  (SEQ ID NO: 20)

ggannuncnccuucggggnannucc;  (SEQ ID NO: 21)

ggavvwuscnccuucggggwawwucc;  (SEQ ID NO: 22)

ggauuuccnccuucggggaaaucc;  (SEQ ID NO: 23)

ggauuuccrccuucggggaaaucc;  (SEQ ID NO: 24)

ggauuuccaccuucggggaaaucc;  (SEQ ID NO: 25)
or ggauuuccgccuucggggaaaucc,  (SEQ ID NO: 26)

wherein r is g or a, y is u or c, w is a or u, s is g or c and n is a, g, u or c. In these sequences, the bold nucleotide is the insertion, i.e. is unpaired. The inserted nucleotide is thus preferably at position 9.

The invention further relates to the shRNA molecules comprising, consisting essentially of or consisting of SEQ ID Nos. 25-32 and 42-43, in particular 25, 26, 42, and 43.

In various embodiments of the invention, the shRNA molecules are further characterized in that they bind to innate immune receptor retinoic acid-inducible gene 1 (RIG-I), in particular *Homo sapiens* RIG-I. The binding is preferably specific in that the binding preferably occurs to RIG-I over other potential binding partners, such as other immune receptors or the other members of the RLR family. This preference may mean that the binding affinity is at least 10×, preferably at least 100× higher than that for other receptors.

In various alternative embodiments, also encompassed by the present invention, the shRNAs can have a nucleotide insertion not in the above-defined position, but rather further upstream in the 5' arm or further downstream in the 3' arm. In some embodiments, an insertion in position n5 may be preferable, although the invention is not limited thereto. It has been found that such molecules, in particular the shRNA with the nucleotide sequence set forth in SEQ ID NO:30 can act as RIG-I antagonists and thus suppress RIG-I mediated signaling. Aside from the different position of the nucleotide insertion, all embodiments disclosed herein for the shRNAs having a nucleotide insertion in $X_1$ in position n7 or higher or in $X_2$ at position nx–6 or lower, as described above, are similarly applicable for these shRNA molecules that have an insertion of an unpaired nucleotide closer to the end of the stem.

The shRNA molecules of the invention have utility in that they are immune-modulatory RNAs (immRNAs), i.e. modulate the immune system. Typically, this means that they are immune-stimulatory although in some embodiments also immune-suppressing activity may be desired.

The invention is thus also directed to compositions that comprise at least one shRNA molecule according to the invention. In various embodiments, such compositions may also comprise a multitude of such shRNA molecules that differ in sequence or structure. Such a plurality of shRNA molecules according to the invention may include at least 2, 3, 4, 5, 6, 7, 8, 9 or 10 or more different species of shRNA molecules. In addition to the RNA molecules of the invention, these compositions may additionally comprise various other components, including, but not limited to other RNA molecules not according to the invention.

The composition may be a pharmaceutical composition, in particular an immunostimulatory composition. In such compositions, the shRNA molecules may act as adjuvants and thus increase the immune response to an antigen of choice that may also be included in such a composition or may be formulated separately. In such compositions, the shRNAs can alternatively or additionally not (only) act as adjuvants, but may have immunostimulatory activity on their own and may thus, for example, act as antiviral or anticancer agents.

Exemplary immunostimulatory compositions include vaccine compositions that may further comprise the actual vaccine, such as an pathogen, toxin or the like, for example an attenuated virus or bacterium, or viral or bacterial proteins. In such embodiments, the shRNA molecule(s) may be used as adjuvants.

Alternatively, the composition may be an antiviral composition, optionally further comprising an active antiviral agent.

In still another alternative, the composition may be an anti-cancer composition, optionally further comprising an active anticancer agent. Exemplary anticancer agents include, without limitation, chemotherapeutics and cell checkpoint inhibitors. Suitable checkpoint inhibitors include, without limitation, CTLA4, PD-1 and PD-L1 inhibitors. Suitable chemotherapeutics include, without limitation, antibodies, alkylating agents, topoisomerase inhibitors, antimetabolites, and anti-microtubule agents.

In both the antiviral and anticancer agents, the shRNA molecules of the invention may be the active agent or may be co-formulated or co-administered with an active agent, antiviral or anticancer. In the latter embodiments, the shRNAs may act as adjuvants or active agents or both.

Independent from the concrete type of composition, the composition may further comprise one or more excipients, typically known and used for the intended purpose, such as pharmaceutically acceptable excipients. Such components include auxiliaries and carriers, such as solvents, conservatives and the like.

The use of the shRNA molecules of the invention as adjuvants or antiviral agents or anticancer agents is therefore explicitly contemplated. In various embodiments, the invention thus features the shRNA molecule of the invention or any composition containing those for use in a method for stimulating the immune system or treating or preventing a viral infection or cancer in a subject in need thereof. The subject may be a mammal, preferably a human. Similarly, the invention covers methods for stimulating the immune system or treating or preventing a viral infection or treating or preventing cancer in a subject in need thereof, the method comprising administering an effective amount of the shRNA molecule according to the invention or of the composition described herein to said subject. "Effective amount", as used in this connection, refers to the amount necessary to exert the desired biological response, i.e. typically activation of the immune system relative to a non-stimulated state or treatment of a viral infection. Accordingly, the effective amount may be a therapeutically or prophylactically effective amount. In such methods the shRNA molecules may be co-administered with the active agent, such as a vaccination agent or a therapeutically active agent, such as an antiviral or anticancer agent.

In the above-described uses and methods, the administration may be topical or systemic.

In various embodiments of the invention, the viral infection that is to be treated or prevented includes, but is not limited to dengue virus infection.

In further embodiments of the invention, the immRNAs disclosed herein are used for cancer treatment or prevention (prophylaxis). Accordingly, the above described methods for the treatment or prevention of viral infection may similarly practiced for the different indication of cancer treatment or prevention.

The inventors have found that shRNA activity may be modulated by structural modification in that a nucleotide insertion is created in the stem structure. As a consequence of this finding, the invention also relates to methods exploiting said finding in that a given small hairpin RNA (shRNA) molecule is modified by a nucleotide insertion in the 5' arm to increase its biological activity. In these methods the template shRNA preferably has the structure, in 5' to 3' orientation, $X_1$-L-$X_2$, wherein $X_1$ and $X_2$ are each nucleotide sequences of 8 to 30 nucleotides in length having sufficient complementarity to one another to form a double-stranded stem structure;

L is a nucleotide sequence forming a loop region;

the first nucleotide positioned at the 5' terminal end of $X_1$ is designated as n1 and the last nucleotide at the 3' terminal end of $X_2$ is designated nx, wherein x is an integer of 25 to 65. In various embodiments, the shRNA is with respect to the elements $X_1$, $X_2$ and L defined as described above in connection with the modified shRNA molecules of the invention. These templates are modified by introducing a nucleotide insertion into $X_1$ in position n7 or higher or in $X_2$ at position nx–6 or lower that remains unpaired in the double-stranded stem structure to create a kink. In further embodiments, such an insertion may also be at a different position, as described above for shRNAs that act as RIG-I antagonists. Suitable methods to generate such an insertion are known to those skilled in the art and are routinely practiced in the field. Furthermore, exemplary techniques to generate such molecules are described by reference to specific sequences in the examples section herein. Additionally, if not already present, the template molecules may be modified by phosphorylating the 5' end such that it is di- or triphosphorylated. Suitable methods for this are known to those skilled imn the art.

It is understood that all embodiments disclosed herein in relation to the RNA molecules of the invention are similarly applicable to all compositions, uses and methods described herein and vice versa.

The present invention is further illustrated by the following examples. However, it should be understood, that the invention is not limited to the exemplified embodiments.

EXAMPLES

Materials and Methods

Protein Expression and Purification

Constructs of human RIG-I (hsRIG-I) and human RIG-I without CARDs (hsRC2) in pETSUMO were transformed into Rosetta II *Escherichia coli* cells (Novagen, Madison, USA) and grown in LB broth supplemented with 2.5% (w/v) glycerol 50 mM phosphate buffer pH 7.4 with antibiotics Kanamycin (50 mg/L) and Chloramphenicol (37 mg/L). The culture was grown at 37° C. with shaking at 200 rpm until the $OD_{600}$ reaches 0.8. The culture was cooled to 18° C. and was induced with 0.5 mM isopropyl-β-D-thiogalactopyranoside (IPTG) for 20 hours. Cells were harvested by centrifuging at 4000 rpm at 4° C. for 10 min and stored at −80° C. Harvested cells were thawed and resuspended in lysis buffer containing 25 mM HEPES pH 8.0, 500 mM NaCl, 10% (v/v) glycerol and 5 mM β-ME. Cells were lysed by passing it through the homogenizer (GEA) at 800 bar. Lysate was clarified by centrifugation a 40 000 rpm for 40 mins at 4° C. The supernatant, which contained the protein of interest with hexa histidine tag was incubated and purified by Ni-NTA beads (Thermofisher). After elution, proteins of interest were cleaved with SUMO protease at ratio of 1:40 (w/w) overnight at 4° C. Proteins were further purified via Ni-Heparin HP tandem column to trap protease and cleaved His-tag and further polishing the protein. They were further purified by size exclusion chromatography using HiLoad 16/600 Superdex 200 (GE Healthcare) column concentrated with vivaspin 30 000 MWCO cut off (GE, Healthcare Life Sciences) and analyzed by sodium dodecyl sulfate-polyacrylamide gel electrophoresis (SDS-PAGE), and then quantified using NanoDrop® spectrophotometer (Thermo Fisher Scientific, USA) by measuring the absorbance at 280 nm. Protein was stored in buffer containing 25 mM HEPES pH 7.4, 150 mM NaCl, 5% (v/v) glycerol and 2 mM DTT and flash frozen in liquid nitrogen.

In Vitro Transcription of RNA

RNAs were transcribed using complementary DNA oligo pairs containing the T7 promoter chemically synthesized from IDT (Integrated DNA Technologies, Inc). Briefly, complementary DNA oligo pairs were annealed by heating to 95° C. and cooling slowly to room temperature. In vitro transcription reactions were carried out in 40 mM Tris-HCl pH 7.9, 30 mM $MgCl_2$, 2 mM spermidine, 10 mM DTT, 0.01% Triton-X100, 5 mM GTP and 4 mM NTP (CTP, ATP and UTP), 1 μM annealed DNA template, 400 nM T7 RNA polymerase, 0.2 U/mL thermostable inorganic pyrophosphatase for 16 hours at 37° C. RNAs transcribed were purified by one volume of phenol:chloroform:isoamyl alcohol (25:24:1) followed by ethanol precipitation. RNA pellet were resuspended in 10 mM HEPES buffer pH 7.4 and subjected to further purification by Hi-Trap Q HP column. The eluted RNAs were subjected to ethanol precipitation and further purified from 20% denaturing urea-PAGE. The RNAs with the expected size were excised from the gel and extracted followed by ethanol precipitation. Purified RNAs were resuspended in buffer containing 10 mM MOPS pH 7, 1 mM EDTA and 50 mM NaCl.

The RNA molecules thus produced are shown in Table 1, where bold letters indicate unpaired nucleotides in the stem region creating a kink in the structure. All immRNAs used were 5'-triphosporylated unless explicitly indicated to the contrary.

TABLE 1

RNA molecules synthesized

| | | SEQ ID NO: |
|---|---|---|
| *RNA-stem modification* | | |
| OHYr01 (3p10LG21) | GGAGGUUUCCUUCGGGAAACGCUCC | 27 |
| OHYr02 (3p10LG17) | GGAUUUCGGCUUCGGCGCGAAAUCC | 28 |
| OHYr04 (3p10LG7) | GGAUUCGCUCCUUCGGGAGGAAUCC | 29 |
| OHYr05 (3p10LG9) | GGAUUUCCGCCUUCGGGGGAAAUCC | 26 |
| OHYr10 (3p10LG5) | GGACGCUUUCCUUCGGGAAAGGUCC | 30 |
| OHYr11 (3p10LG19) | GGAUUGGUCCUUCGGGACGCAAUCC | 31 |
| OHYr14 (3p10LG8) | GGAUUUCGCCCUUCGGGGGAAAUCC | 32 |
| *RNA-stem length* | | |
| OHYr12 | GGACGCUUCGGCGUCC | 33 |
| OHYr09 | GGACGUGCUUCGGCACGUCC | 34 |
| OHYr20 | GGAUUUCCCUUCGGGGAAAUCC | 35 |
| OHYr23 (3p10L) | GGACGUACGUUUCGACGUACGUCC | 37 |
| OHYr03 | GGAUUUCGCGCUUCGGCGCGAAAUCC | 36 |
| OHYr07 | GGACGUACGUGCUUCGGCACGUACGUCC | 38 |
| OHYr13 | GGACGUACGUACGCUUCGGCGUACGUACGUCC | 39 |
| OHYr06 | GGACGUACGUACGUACGUGCUUCGGCACGUACGUACGUCC | 40 |
| OHYr08 | GGACGUACGUACGUGCACGUACGUACGUGCUUCGGCACGUACGUACGUGCACGUACGUACGUCC | 41 |
| *RNA-base composition* | | |
| OHYr16 | GGAUUUCCACCUUCGGGGGAAAUCC | 25 |
| OHYr17 | GGAUUUCAUACUUCGGUUGAAAUCC | 42 |
| OHYr18 | GGAUUUCGCGCUUCGGCCGAAAUCC | 43 |
| OHYr21 | GGAUUUCCCCUUCGGGGGAAAUCC | 44 |
| OHYr22 | GGAGGGAAACUUCGGUUUCCCUCC | 45 |

NADH Coupled ATPase Assay

ATPase assay was carried out for hsRIG-I in buffer containing 25 mM MOPs pH7.4, 150 mM KCl, 2 mM DTT and 0.01% Triton X-100 in the presence of 5× assay mix containing 1 mM NADH, 100 U/ml lactic dehydrogenase, 500 U/ml pyruvate kinase, 2.5 mM phosphoenol pyruvic acid. To determine the Km of ATP, 20 nM protein of interest was used. Saturating amount of RNA was added at the concentration of 1 μM and the protein RNA mixture was incubated 2 hours prior to the initiation of reaction. Reaction was initiated by the addition of 1 to 1 molar ratio of ATP and $MgCl_2$ diluted to 8 different concentrations ranging from 39 nM to 5000 nM and were monitored over 10 mins at Abs of 340 nm in a 96 well plate format using Cytation 3 Cell Imaging Multimode Reader (BioTek) at room temperature. All data were obtained in triplicate and plotted as rate of NADH hydrolysis as function of ATP concentration using GraphPad Prism® version 6 programme using the Michaelis-Menten equation (GraphPad Software, Inc.). Rates were obtained over the duration of 10 mins and are corrected for background NADH decomposition.

Cell Culture and IFN-β Induction Assays

HEK-Lucia™ RIG-I cells derived from HEK293 cell, and THP1-Dual™ derived from THP-1 cells are cell lines generated to express the secreted Lucia luciferase reporter gene. This reporter gene is under the control of an IFN-inducible ISG54 promoter enhanced by a multimeric IFN-stimulated response element (ISRE). Cells were maintained in T-75 flask in Dulbecco's Modified Eagle Medium (DMEM, GIBCO) supplemented with 10% fetal bovine serum. IFN-β induction assay was carried out in 96 well plates with seeding density of 50,000 cells/well. Cells were transfected with RNA of varying concentration from 300 nM to 6 nM using LyoVec (InvivoGen). After 24 hours, the 10 µL cell culture medium was collected and mixed with 50 µl of QUANTI-Luc™ (an assay reagent containing all the components required to quantitatively measure the activity of Lucia luciferase). Luminescence was measured using a Biotek Synergy H1 plate reader (Biotek, Winooski, Vt., United States). Time point experiment was also carried out for using 100 nM RNA in 96 well plate format for up to 72 hours.

Cell Based Inhibition Assay

Cell based inhibition assay was carried out using HEK-Lucia™ RIG-I cells. HEK-Lucia™ RIG-I cells were plated at a seeding density of 50,000 cells/well and transfected with 10 nM of 3p10L with different concentration of antagonist 3p10LG5 ranging from 300 nM to 6 nM using LyoVec as per the manufacturer's recommendation. After 24 hours, 10 µL cell culture medium was collected and mixed with 50 µl of QUANTI-Luc™ and luminescence was measured using Biotek Synergy H1 plate All the assays were carried out in Corning 96-well plates as triplicates. The half maximal inhibitory concentration ($IC_{50}$) of an inhibitor was determined using GraphPad Prism version 6 (GraphPad Software, La Jolla Calif., USA).

Hydrogen/Deuterium Exchange (HDX) Coupled With Mass Spectrometry (HDX-MS)

5 µl of 10 µM of RIG-I protein in 25 mM HEPES, pH 7.4, 150 mM NaCl, 5% glycerol and 2 mM DTT were incubated with 10 fold excess of RNA ligands 3p10LG5, 3p10LG9 and 3p10LA9 at 4° C. for 1 hour. The protein complex mixture was diluted into 20 µl $D_2O$ on exchange buffer (50 mM HEPES, pH 7.4, 150 mM NaCl, 5 mM $MgCl_2$, 2 mM DTT) and incubated at 4° C. and quenched by mixing with 25 µl of ice-cold 4 M gHCL, 1% trifluoroacetic acid. Samples were incubated in $D_2O$ on exchange buffer containing 3 M gHCL (50 mM HEPES, pH 7.4, 150 mM NaCl, 5 mM $MgCl_2$, 2 mM DTT and 3 M gHCL) overnight at room temperature. The sample tubes were immediately placed on dry ice after the quenching reactions until the samples were injected into the HDX platform. Upon injection, samples were passed through an immobilized pepsin column (2 mm×2 cm) at 200 µl min−1 and the digested peptides were captured on a 2 mm×1 cm C8 trap column (Agilent) and desalted. Peptides were separated across a 2.1 mm×5 cm C18 column (1.9 □m Hypersil Gold, ThermoFisher) with a linear gradient of 4%-40% CH3CN and 0.3% formic acid, over 5 min. Sample handling, protein digestion and peptide separation were conducted at 4° C. Mass spectrometric data were acquired using an Orbitrap mass spectrometer (Q Exactive, ThermoFisher) with a measured resolving power of 65,000 at m/z 400. HDX analyses were performed in triplicate, with single preparations of each protein ligand complex. The intensity weighted mean m/z centroid value of each peptide envelope was calculated and subsequently converted into a percentage of deuterium incorporation. Corrections for back-exchange were made on the basis of an estimated 70% deuterium recovery, and accounting for the known 80% deuterium content of the deuterium exchange buffer. When comparing the two samples, the perturbation % D is determined by calculating the difference between the two samples. HDX Workbench colors each peptide according to the smooth color gradient HDX perturbation key (% D) shown in each indicated figure. Differences in % D between −5% to 5% are considered non-significant and are colored gray according to the HDX perturbation key (Pascal et al, 2012). In addition, unpaired t-tests were calculated to detect statistically significant ($p<0.05$) differences between samples at each time point. At least one time point with a p-value less than 0.05 was present for each peptide in the data set further confirming that the difference was significant.

Data Rendering: the HDX data from all overlapping peptides were consolidated to individual amino acid values using a residue averaging approach. Briefly, for each residue, the deuterium incorporation values and peptide lengths from all overlapping peptides were assembled. A weighting function was applied in which shorter peptides were weighted more heavily, and longer peptides were weighted less. Each of the weighted deuterium incorporation values was then averaged to produce a single value for each amino acid. The initial two residues of each peptide, as well as prolines, were omitted from the calculations. This approach is similar to that previously described (Keppel & Weis, 2015).

Human Skin DC Isolation

Protocols for isolating single cells from human skin were described in detail previously (Cerny et al. (2014), PLoS Pathog. 2014; 10(12):e1004548). For the isolation of human skin cells, 300 mm dermatome sections were incubated in RPMI+10% heat-inactivated FBS (Gibco) containing 0.8 mg/ml collagenase (Type IV, Worthington-Biochemical) and 0.05 mg/ml DNase I (Roche) for 12 h. After incubation, cells were filtered through a 70 µm strainer to obtain a single cell suspension.

Cell Lines

HEK-293T, U937 and A549 cells (ATCC) were grown in RPMI supplemented with 10% fetal bovine serum (FBS) (Gibco). U937 cells expressing DC-SIGN were generated by lentiviral transfection (Züst et al. (2013), PLoS Pathog 9:e1003521). HEK-293T cells expressing MX1P-luc were generated by Georg Kochs (Kochs et al. (2009), J Gen Virol 90:2990-2994) (University of Freiburg, Germany). HEK-293T cells containing the ISRE-luc reporter plasmid was generated by transfecting 0.5 µg of ISRE-luc plasmid using 293fectin Transfection Reagent (Thermo Fisher Scientific).

RIG-I knockout cell lines were generated by lentivirus transduction of U937-DC cells with pRRL-gRNA-Cas9-T2A plasmid containing a gRNA sequence targeting exon 1 of RIG-I. The RIG-I gRNA-containing plasmid was obtained from Dr Alvin Tan (Genome Institute of Singapore, A*STAR, Singapore). Lentiviral particles were produced on 293T cells by using 293fectin Transfection Reagent (Thermo Fisher Scientific) with the following three plasmids: (i) pMDLg/pRRE, which includes gag, coding for the virion main structural proteins; pol, responsible for the retrovirus-specific enzymes; and RRE, a binding site for the Rev protein which facilitates export of the RNA from the nucleus. (ii) pRSV-Rev, encoding the HIV-1 rev under the transcriptional control of a RSV U3 promoter; (iii) pMD2.G, a VSV-G envelope expressing plasmid. pMDLg/pRRE (addgene #12251), pRSV-Rev (addgene #12253) and pMD2.G were generated by Prof. Didier Trono (Lausanne, Switzerland). Successfully transduced cells were selected by supplementing the culture medium with 2 µg/ml puromycin. Genomic DNA was extracted from cells by using a "Hot-SHOT" genomic DNA preparation method described in (Truett et al. (2000), BioTechniques 29:52-54). Purified DNA was sent for sequencing (First Base) using primers which flank exon 1 (Forward: 5' GGAGG-GAAACGAAACTAGCC 3' (SEQ ID NO:46) and Reverse: 5' GCTCCTCAAACTCTGGCAAC 3' (SEQ ID NO:47). Sequences were compared with publicly available sequence for human DDX58 on Ensembl (ENSG00000107201.9).

Virus

DENV-2 strain TSV01 (NCBI accession number AY037116.1) used for infection experiments in human cell lines is a patient isolate that have been passaged in C6/36 mosquito cells for 5-20 passages. D2Y98P used in the infection of primary human skin DCs was derived from an infectious clone. The enhanced viral RNA synthesis of D2Y98P was mapped to a natural mutation in NS4b protein and this mutation had no effect on the IFN-inhibiting capacity of the virus (Grant et al. (2011), Journal of Virology 85:7775-7787).

RNA Screening With Type I Interferon Bioassay.

HEK-293T MX1P-luc cells were seeded into white 96-well plates at a density of $2.5 \times 10^4$ cells per well and incubated overnight. immRNA was diluted to the appropriate concentrations and transfected with 293fectin transfection reagent (Thermo Fisher Scientific) according to the manufacturer's instructions. Cells were incubated for 24 h and then lysed and analyzed using Bright-Glo Luciferase Assay System (Promega) on a GloMax-Multi Microplate Reader (Promega) according to the manufacturer's instructions.

Quantitative PCR (qPCR)

U937-DC SIGN cells were seeded in a 24-well plate at a density of $3.0 \times 10^5$ cells per well in 500 µl of RPMI with 10% FBS and incubated overnight. immRNA was diluted to the appropriate concentrations and transfected (in triplicate) with Hilymax (Dojindo Molecular Technologies) according to the manufacturer's instructions. After 24 h incubation, cells were centrifuged at 500×g for 4 mins and harvested in Trizol reagent (Thermo Fisher Scientific) and total RNA was harvested according to the manufacturer's instructions. RNA was reverse transcribed using the SuperScript VILO cDNA synthesis kit (Invitrogen). PCR primers were purchased from Integrated DNA Technology and quantitative RT-PCR was performed on an ABI 7900 HT Real-Time PCR system (Applied Biosystems) using iTaq Universal SYBR Green Supermix (Bio-rad Laboratories). Primer sequences can be found in the table below. Analysis of qPCR data was done by relative quantitation by the ΔΔCt method using beta-actin as the reference gene control.

| Gene | Species | Sense/Antisense | Sequence (5' to 3') |
|---|---|---|---|
| IFNB | Human | Sense | CTCTCCTGTTGTGCTTCTCC (SEQ ID NO: 48) |
| IFNB | Human | Antisense | GTCAAAGTTCATCCTGTCCTTG (SEQ ID NO: 49) |
| ACTB | Human | Sense | TCGTGCGTGACATTAAGGAG (SEQ ID NO: 50) |
| ACTB | Human | Antisense | GTCAGGCAGCTCGTAGCTCT (SEQ ID NO: 51) |
| DDX58 | Human | Sense | GCCATTACACTGTGCTTGGAGA (SEQ ID NO: 52) |
| DDX58 | Human | Antisense | CCAGTTGCAATATCCTCCACCA (SEQ ID NO: 53) |
| RSAD2 | Human | Sense | CACAAAGAAGTGTCCTGCTTGGT (SEQ ID NO: 54) |
| RSAD2 | Human | Antisense | AAGCGCATATATTCATCCAGAATAAG (SEQ ID NO: 55) |

Bioassay for Type I Interferon Production

Supernatant from immRNA-transfected cells was incubated on HEK-293T cells transfected the day before with 0.5 µg of ISRE-luc plasmid and plated in a 96-well white opaque plate the next day. Supernatant was incubated for 6 h before being lysed and analyzed by using Bright-Glo Luciferase Assay System (Promega) on a GloMax-Multi Microplate Reader (Promega) according to the manufacturer's instructions.

Type I Interferon Bioassay for RLR-Expressing HEK-293T Cells Transfected With immRNA.

HEK-293T cells were seeded in a 24-well plate at a density of $1.25 \times 10^5$ cells per well in RPMI with 10% FBS. 50 ng of pUNO-hRIG-I or pUNO-hMDA5 (Luo et al. (2011), Cell 147:409-422) was transfected using Lyovec (Invivogen) and cells were incubated overnight. HEK-293T cells expressing RLRs were transfected with immRNA. Supernatant from cells was harvested 24 h after transfection with dsRNA and type I interferon bioassay using HEK-293T cells expressing ISRE-luc was done.

U937-DC SIGN Cell IFNAR Blocking Assay

U937-DC SIGN cells were seeded in a 96-well plate at a density of $0.6 \times 10^5$ cells per well and transfected with immRNA (in triplicate) with Hilymax (Dojindo Molecular Technologies) according to the manufacturer's instructions. After 6 hours, anti-human IFNAR blocking antibody (clone MMHAR-2, PBL Interferon Source) or IgG isotype control (R&D systems) was added at a concentration of 10 ug/mL. After overnight incubation, supernatant was harvested and a bioassay for type I interferon was done. U937-DC SIGN cells were infected with DENV-2 (TSV01) at MOI-1, and infection was quantified.

DENV-2 Infection and Flow Cytometry Analysis.

U937-DC SIGN cells were seeded in a 96-well plate at a density of $0.6 \times 10^5$ cells per well and transfected with immRNA (in triplicate) using Hilymax (Dojindo Molecular Technologies) according to the manufacturer's instructions. A549 cells were seeded in a 96-well plate at a density of $1.0 \times 10^4$ cells per well and transfected with immRNA using 293fectin transfection reagent (Thermo Fisher Scientific) according to the manufacturer's instructions. After 24 h incubation, transfected U937-DC-SIGN and A549 cells were infected with DENV-2 (TSV01 strain) at a MOI-1 and MOI-5 respectively. Cells were incubated with RPMI containing DENV-2 for 2 h. After two washes, infected cells were resuspended in RPMI with 10% FBS and placed in the incubator for 24 h. For FACS analysis, washed cells were fixed and permeabilized by resuspending cells in Cytofix/Cytoperm buffer (BD Biosciences). Dengue E protein was stained with anti-E protein antibody (4G2) (ATCC) conjugated to Alexa 647, and anti-NS1 antibody conjugated to Alexa 488. Fluorescence on these cells was measured on a BD FACS Canto II analyser (BD Biosciences) and analysis was done on Flowjo (Treestar). Cells that stained positive for both NS1 and E protein were considered infected.

Human skin DCs were isolated and transfected with immRNA as described previously. For prophylactic studies, isolated human skin DCs were infected with DENV-2 (D2Y98P strain) at a MOI-5 24 h post-transfection. For therapeutic studies, isolated human skin DCs were infected with DENV-2 (D2Y98P strain) at a MOI-5 and transfection of immRNA was done 4 h, 6 h and 24 h post-infection. Infected cells were analysed 72 h post-infection to determine the percentage of infected cells using flow cytometry. 1000 U of human recombinant IFN-b (Immunotools) was added to cells at 4 h post-infection. Flow cytometry was performed on an LSRII (Becton Dickinson [BD]) and data were analysed using FlowJo (TreeStar). The following reagents for staining of human skin DCs were used: fixable live/dead dye (Thermo Fisher Scientific), anti-CD1a (HI149) (Biolegend), anti-CD11c (B-1y6), anti-CD45 (H130), anti-HLA-DR (L243) (all from BD Biosciences), anti-CD141 (AD5-14H12) (Miltenyi), anti-CD14 (RMO52) (Beckman Coulter), and anti-E protein (4G2) (ATCC) conjugated to Alexa 647.

RNAseq Experiments

Single cell RNAseq: skin cell subsets were identified as described under flow cytometry analysis and sorted individually into 96-well PCR plates and frozen immediately. Single cells were processed using the SMARTseq2 protocol (Picelli et al. (2014), Nature Protocols 9:171-181), with the following modifications:

1. 1 mg/ml BSA Lysis buffer (Ambion® Thermo Fisher Scientific, Waltham, Mass., USA)
2. Use of 200 pg cDNA with 1/5 reaction of Illumina Nextera XT kit (Illumina, San Diego, Calif., USA)

The length distribution of the cDNA libraries was monitored using a DNA High Sensitivity Reagent Kit on the Perkin Elmer Labchip (Perkin Elmer, Waltham, Mass., USA). All samples were subjected to an indexed paired-end sequencing run of 2×151 cycles on an Illumina HiSeq 4000 system (Illumina, San Diego, Calif., USA) (309 samples/lane).

Pair-end raw reads were aligned to human reference genome using RSEM version 1.3.0 (36). Human reference genome GRCh38 version 25 release by Gencode was used (https://www.gencodegenes.org/human/release_25.html). Transcript Per Million read (TPM) values were calculated using RSEM version 1.3.0 (Li & Dewey (2011), BMC Bioinformatics 12:323) and were log-transformed—log 2(expression+1)—for downstream analysis. Quality control, selection of highly variable genes, Principal Component Analysis (PCA) and differential gene analysis was performed using Seurat R package version 2.0 (Butler et al. (2018), Nat Biotechnol 36:411-420). Low-quality cells from our data set were filtered out based on a threshold for the number of genes detected (a minimum of 200 unique genes per cell), and all genes that were not detected in at least 1.9% of all our single cells were discarded, leaving 159 cells and 15174 genes for all further analyses. Principal Components Analysis (PCA) was performed on the 810 highly variable genes after scaling the data. Differential gene expression was analyzed using the negative bimodal Wald test, selecting genes with an adjusted p-value (Benjamini-Hochberg correction) for the estimated fold changes <0.05.

Bulk RNAseq: 500 cell were sorted per subset and donor and RNA was isolated using PicoPure RNA isolation kits. cDNA Libraries were prepared according to Picelli et al. (supra) with following modifications:

1. 1 mg/ml BSA Lysis buffer (Ambion® Thermo Fisher Scientific, Waltham, Mass., USA)
2. Addition of 20 µM TSO;
3. Use of 200 pg cDNA with 1/5 reaction of Illumina Nextera XT kit (Illumina, San Diego, Calif., USA).

The length distribution of the cDNA libraries was monitored using a DNA High Sensitivity Reagent Kit on the Perkin Elmer Labchip (Perkin Elmer, Waltham, Mass., USA). All samples were subjected to an indexed paired-end sequencing run of 2×151 cycles on an Illumina HiSeq 4000 system (Illumina, San Diego, Calif., USA) (32 samples/lane).

Paired-end reads of length 150 bp (300 bp for a pair) were mapped to the human transcriptome sequences obtained from Gencode version 29 (Frankish et al. (2018), Nucleic Acids Research 47:D766-D773) using Salmon (version 0.11.3) (Patro et al. (2017), Nat Rev Immunol 14:417-419). Transcript-wise read counts obtained from Salmon were summarized to gene-wise counts using tx2gene R/Bioconductor package (Soneson et al. (2015), F1000Res 4:1521-18). Gene-wise summarized counts for samples relevant to the conditions being compared were loaded into DESeq2 (Love et al. (2014), Genome Biol 15:31-21). Genes with at least one count in at least one sample were retained in the dataset. Using DESeq2, the counts data was fitted to a negative binomial generalized linear model. Size factors for library size normalization and the mean and dispersion parameters for each gene were estimated using estimateSizeFactors and estimateDispersion functions. Differential gene expression was analyzed using the negative binomial Wald test. The p-values for the estimated fold changes were corrected for multiple testing using the Benjamini-Hochberg method and differentially expressed genes were selected based on an adjusted p-value <0.05. Lists of genes identified as differentially expressed upon G9 stimulation in each cell type were supplied to Ingenuity Pathway Analysis™ (IPA) software along with respective fold changes and p-values. Pathway enrichment analysis based on differential expression was performed in IPA for determining pathways that are significantly modulated by stimulation in each cell type.

Example 1: HEL2i Domain Samples the RNA PAMP for RIG-I Activation

To infer the structural basis of RNA sensing by RIG-I protein, the five available structures of human RIG-I HEL-CTD dsRNA complex structures were compared. By superpositioning the invariant HEL1-dsRNA-CTD domains, it was found that HEL2-HEL2i domains moved relatively along the dsRNA backbone. HEL2i plays the central role in releasing the CARDs domain upon binding to the RNA PAMP. This is mediated by the two opposing functional surfaces: one RNA sampling surface with conserved RNA recognizing residues (K508-Q511 in human RIG-I) and one surface to interact with and sequester CARD2 domain from releasing (Luo (2014) RNA Biol 11: 25-32; Zheng et al., supra). Across the five structures, HEL2i samples approximately 5 base pairs (base pair 5-10, counting from the 5' end triphosphoryated nucleotide of the top strand). It is hypothesized, without being bound thereto, that any structural perturbation at this region will affect the intramolecular movement of the HEL-CTD domains relative to each other and alter the kinetics of CARDs release, i.e. the threshold of activation. To test this hypothesis, RNA nucleotide insertions and point mutations were introduced into the starting immRNA—3p10L (5' triphosphorylated RNA with 10 base-paired stem region; SEQ ID NO:37) as described by Kohlway et al. (2013, supra) and evaluated using both biochemical and cell based-assays.

Example 2: Position Specific Guanosine Insertions Activate RIG-I Differently

To assess how an inserted nucleotide may affect 3p10L's (SEQ ID NO:37) ability to activate RIG-I, 6 RNA species with 1 guanosine insertion along the dsRNA stem of 3p10L, namely 3p10LG5 (SEQ ID NO:30), 3p10LG7 (SEQ ID NO:29), 3p10LG9 (SEQ ID NO:26), 3p10LG17 (SEQ ID NO:28), 3p10LG19 (SEQ ID NO:31) and 3p10LG21 (SEQ ID NO:27) were generated and the relative IFN-producing activity of these RNAs was compared with the one of 3p10L (FIG. 1A). These RNA molecules were tested using the HEK-Lucia™ RIG-I reporter cell line for IFN-β expression (with HEK-Lucia™ null cells as control) to determine which insertions in the stem region could result in a higher IFN-β activity. One of the RNAs with insertion of guanosine at position 9 of the stem in hairpin RNA (3p10LG9; SEQ ID NO:26) was a potent inducer of RIG-I activation with at least 3 fold higher IFN-β induction compared to the parental immune modulatory RNA (immRNA) 3p10L (FIG. 1B). RNAs with insertions of G at position 7 or 17 had activities comparable to 3p10L. The ATPase assay carried out using 20 nM of hsRIG-I protein with the saturating concentration of immRNAs (1 µM) revealed a Kcat for ATP of 9.01 $s^{-1}$ and 11.7 $s^{-1}$ for 3p10L and 3p10LG9 respectively (FIG. 1C). Thus, immRNAs with G-insertions which are at least 6 base pairs away from the 5'ppp end remain agonistic and an insertion at position G9 is the most potent activator of RIG-I.

In contrast to those activating immRNA described above, immRNA 3p10LG5 (SEQ ID NO:30) showed no activity in both enzymatic and cellular activity assays (FIGS. 1B and C) suggesting that 3p10LG5 could inactivate RIG-I. To further prove this, a cell-based competitive inhibition assay was used and it was determined that the half maximal inhibitory concentration ($IC_{50}$) for 3p10LG5 was 34 nM. This was measured by transfecting 10 nM 3p10L (SEQ ID NO:37) with increasing concentrations of 3p10LG5 (FIG. 1D). The results showed that 3p10LG5 acts as an antagonist to RIG-I. To ensure that all immRNAs with G-insertions bind to RIG-I, analytical gel filtration experiments were conducted using purified proteins of hsRC2 and immRNAs. It was found that all immRNAs were able to form stable RIG-I:RNA complexes in buffer with physiological concentration of electrolytes (data not shown). Taken together, by introducing G-insertions at different positions of 3p10L, 3p10LG9 was identified as the most potent RIG-I agonist among those tested and 3p10LG5 as a RIG-I antagonist.

Figure 2:
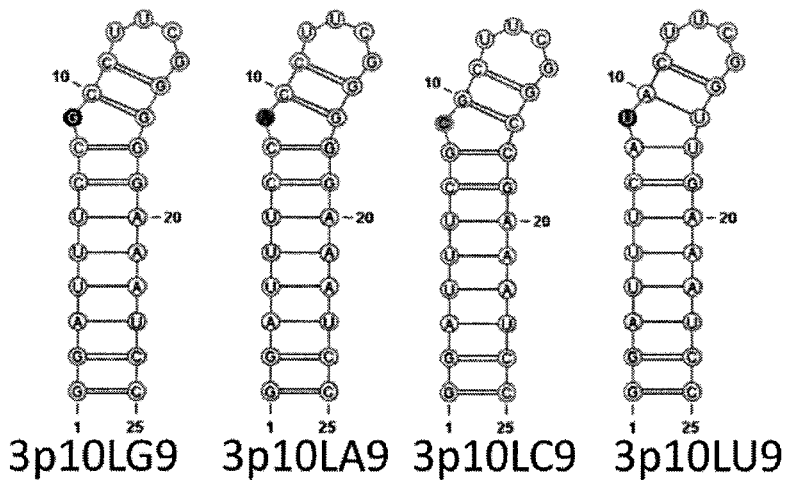
FIG. 2. Insertion of purine bases at position 9 along the hairpin RNA improves the potency of the immRNA 3p10L. (A) The design of hairpin RNA introducing different bases along the stem region at position 9 of RNA. (B) Cell based assay of different RNA in HEK-Lucia™ RIG-I and HEK-Lucia™ null. RNA was transfected at a fixed concentration of 100 nM and luminescence was measured 24 hours post-transfection. Results are measured in triplicate and presented as RLU. (C) The ATPase activity of RNAs with different base insertion at position 9. The data were fitted to the Michaelis-Menten equation and the $K_{m,ATP}$ and $K_{cat,ATP}$ was determine with saturating amount of RNA to hsRIG-I.
Figure 2:
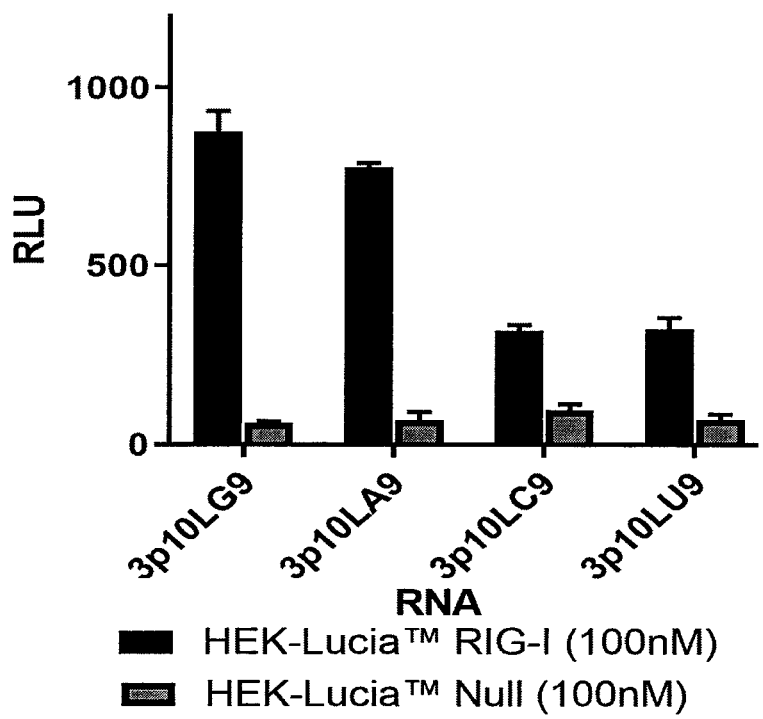
Figure 2:
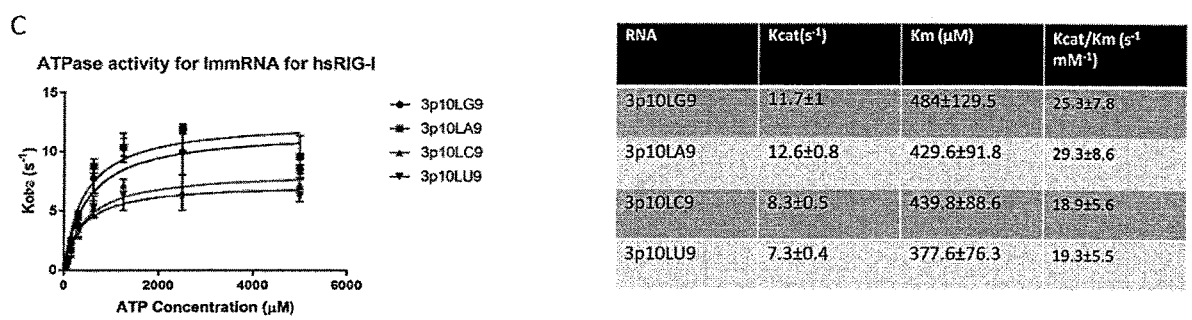

Example 3: Purine Base Insertions at the Position 9 of immRNAs Increase the Potency To evaluate whether inserting different bases at the position 9 of 3p10L activates RIG-I differently, G9 residue of 3p10LG9 was replaced by adenosine, uridine or cytosine (FIG. 2A). At 24 hrs post stimulation of the HEK-Lucia™ RIG-I cells, 3p10LG9 (SEQ ID NO:26) and A9 (SEQ ID NO:25) have similar IFN-β activation activity, which is about twice the activity observed for 3p10L. In comparison, immRNAs with pyrimidine insertions (3p10LC9 (SEQ ID NO:43) and U9 (SEQ ID NO:42)) showed similar levels of activity compared to 3p10L (FIG. 2B). ImmRNAs with purine insertions (3p10LG9 and A9) outperformed those with pyrimidine insertions in the ATPase assay: higher kcat values (11.7 and 12.6 versus 8.3 and 7.3 $s^{-1}$) and higher catalytic efficiency (25.3 and 29.3 versus 18.9 and 19.3 $mM^{-1}s^{-1}$) were observed (FIG. 2C). These results revealed that the insertion of purine bases at position 9 potentiate 3p10L by increasing the RIG-I enzymatic and IFN-inducing activities.

Example 4: HDX-MS Captured Stronger Allosteric Effect Upon 3p10LG9 Binding to RIG-I Compared to 3p10L HDX-MS is a sensitive and robust method to study protein dynamics upon ligand binding (Zheng et al. (2017), Nat Commun 8: 923; Zheng et al. (2015), supra). The intra-molecular interaction between HEL2i and CARDs and the allosteric release of CARDs during RNA recognition by RIG-I was captured. Briefly, the protein-RNA complexes were exposed to deuterated water, were denatured into peptides, and were subjected LC-MS as described by Zheng et al. (2015, supra). The HDX data were consolidated and mapped to the structure model using a residue averaging approach using HDX Workbench as described previously (Keppel & Weis 82015), Journal of the American Society for Mass Spectrometry 26: 547-554; Pascal et al. (2012), Journal of the American Society for Mass Spectrometry 23: 1512-1521; Zheng et al. (2015), supra).

To provide a mechanistic explanation for the increased enzymatic and cellular activities of 3p10LG9 over 3p10L, the method of hydrogen/deuterium exchange coupled to mass spectrometry (HDX-MS) was used to analyze the structural dynamics of RIG-I upon binding to 3p10LG9 and 3p10L. HDX profiles revealed CARDs domain and in particular the CARD2 latch peptide (Y103-114) exhibited higher deuterium incorporations for 3p10LG9 with hsRIG-I as compared to 3p10L. Key differences between 3p10L and 3p10LG9 include a tighter binding of 3p10LG9 with hsRIG-I in HEL1 domain particularly, the motif Ia (F296-310), and Ic (1343-366) which are known to interact with RNA. Another observation was that the binding of CTD capping loop (F842-856) and CTD binding region (V893-904) to 3p10LG9 is tighter compared to 3p10L (data not shown). HDX-MS revealed that 3p10LG9 bound to HEL-CTD tighter than 3p10L to further destabilize the CARD2-HEL2i intramolecular inhibitory interface, leading to a more exposed CARDs and greater RIG-I stimulation (data not shown). When the RIG-I 3p10LG9 complex was modelled, the inserted G9 base seemed to be positioned in close proximity to the back of HEL2i, leading to the conclusion that G9 insertion restricted HEL2i movement and provided additional repelling force to release CARDs from HEL-CTD: 3p10LG9 complex.

Example 5: 3p10LA9 Exhibited Time and Cell-Type Dependent Enhanced Activity Compared to 3p10LG9

Figure 3:
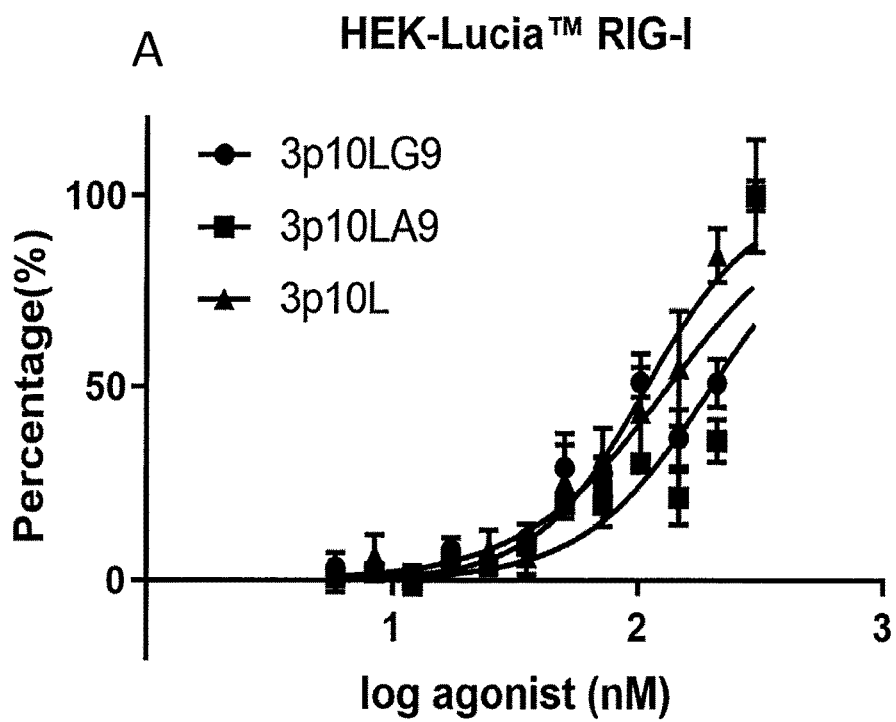
FIG. 3. 3p10LA9 (SEQ ID NO:25) demonstrated stronger activity than 3p10LG9 (SEQ ID NO:26) and 3p10L (SEQ ID NO:37) in two different reporter cells. (A) RNA was transfected into HEK-Lucia™ RIG-I at a different concentration range of RNA and luminescence was measured 24 hours post-transfection. Results were measured in triplicate and presented as normalized percentage of the maximum activity vs log concentration. The $EC_{50}$ for 3p10L G9 was 133 nM, 3p10LA9 was 199 nM, 3p10L was 108 nM, B) RNA was transfected at a fixed concentration of 100 nM in HEK-Lucia™ RIG-I and luminescence was measured 4, 6, 8, 10, 12, 24, 48 and 72 hours post-transfection. C) RNA was transfected in THP1-Dual™ at a different concentration range of RNA and luminescence was measured 48 hours post-transfection. Results were measured in triplicate and presented as percentage of the maximum activity vs log concentration. The $EC_{50}$ for 3p10L G9 was 91 nM, 3p10LA9 was 51 nM, 3p10L was 226 nM D) RNA was transfected at a fixed concentration of 100 nM in THP1-Dual™ and luminescence was measured 4, 6, 8, 10, 12, 24, 48 and 72 hours post-transfection.
Figure 3:
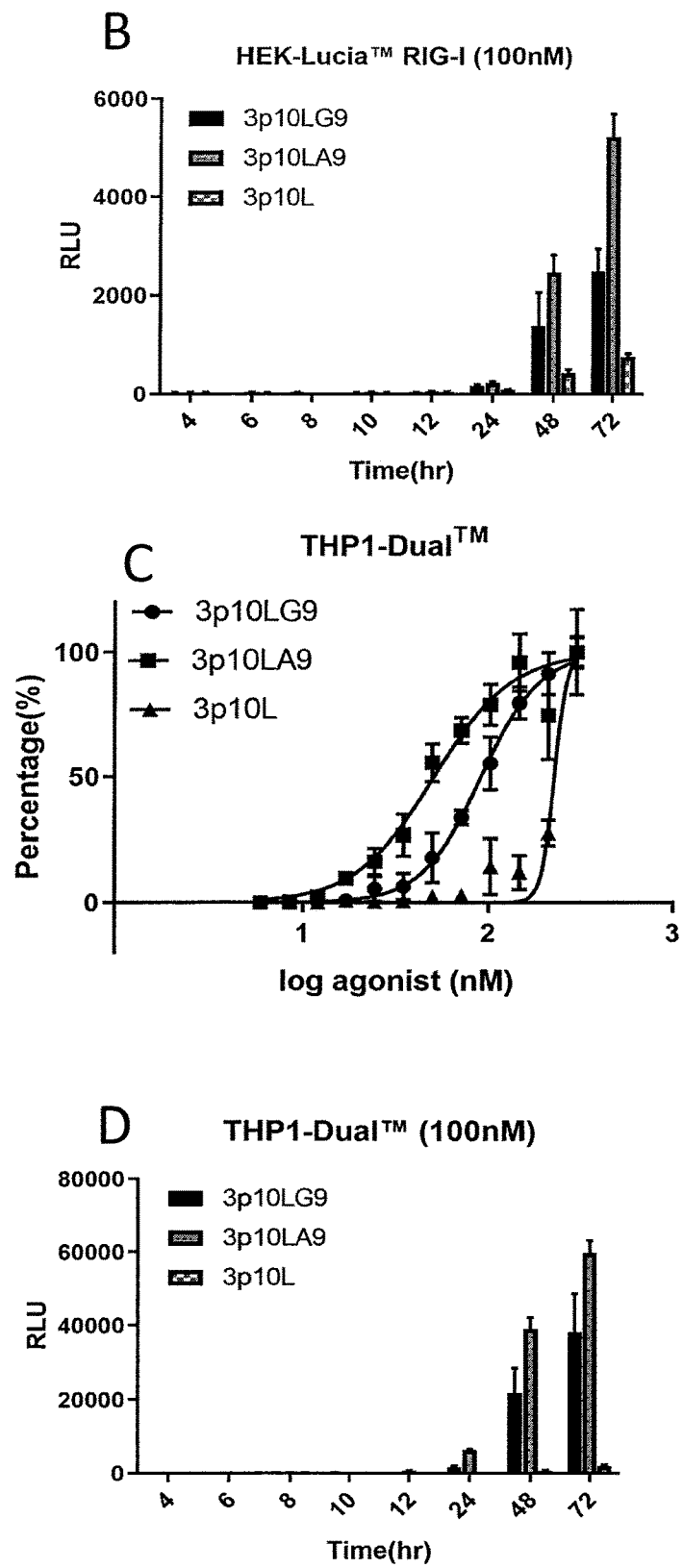

To further explore the cellular activities of the lead immRNAs, cell based kinetic experiments were carried out by looking at the concentration dependent response and time post-stimuli time response of the two best immRNAs 3p10LG9 (SEQ ID NO:26) and A9 (SEQ ID NO:25) against 3p10L (SEQ ID NO:37). In HEK-Lucia™ RIG-I cells, 3p10LG9 and A9 showed similar and higher activities than the 3p10L at 24 hrs post transfection (FIG. 3A). In the time dependent experiment, the stimulatory activities of the 3 immRNAs were evidently detected at 24 hours and continuously increased at 48 hours and 72 hours post-transfection.

Notably, 3p10A9 became more potent and stimulate more luciferase signals than 3p10LG9 after 24 hours (FIG. 3B). Then a second type of cells—THP1-Dual™ which are monocytic cells with IRF-Luc reporter was used. While EC$_{50}$ values could not be accurately determined, 3p10LA9 seemed to be the most potent immRNA, with 3p10LG9 the second and 3p10L the least (FIG. 3C). In THP-1 reporter cells, the difference between 3p10LA9 and 3p10LG9 became more evident in both concentration dependent and time dependent manners (FIGS. 3C and 3D).

Example 6: Biochemical Characterization of Different immRNA Molecules

Figure 4:
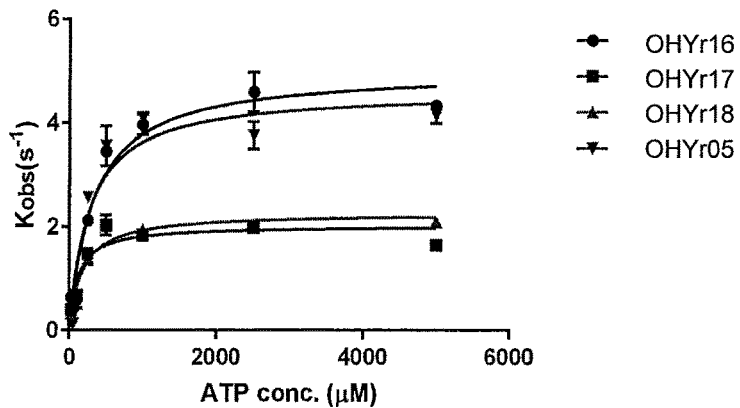
FIG. 4. Michaelis-Menten plot showing ATPase activity of *Mus musculus* RIG-I (mmRIG-I) and mmRIG-I Δ CARDs binding to different RNA molecules (A) Rate of catalysis over ATP concentration ranging from 0 to 5 mM— for mmRIG-I stimulated by short RNA hairpins with different stem modification (B) Rate of catalysis over ATP concentration ranging from 0 to 5 mM for mmRIG-I stimulated by RNA hairpins of different base composition (C) Rate of catalysis over ATP concentration ranging from 0 to 5 mM for mmRIG-I stimulated by RNA hairpins of different length.
Figure 4:
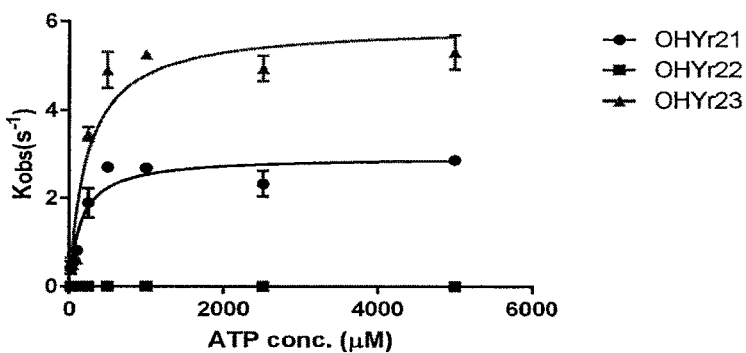
Figure 4:
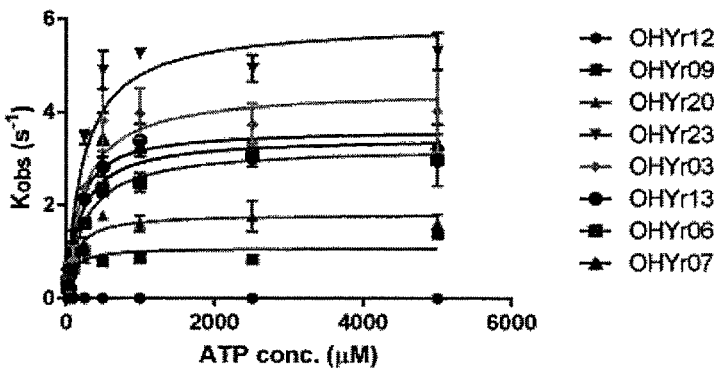

To test the ability of different immRNAs to activate RIG-I, purified recombinant full length RIG-I was subjected to NADH coupled ATPase assay with saturating amount of immRNA prior to initiation of reaction with varying concentration of ATP. Briefly, the assay was carried out in buffer containing 25 mM MOPS pH7.4, 150 mM KCl, 2 mM DTT and 0.01% Triton X-100 in the presence of 5× assay mix containing 1 mM NADH, 100 U/ml lactic dehydrogenase, 500 U/ml pyruvate kinase, 2.5 mM phosphoenol pyruvic acid. These experiments demonstrated that some immRNAs activate RIG-I, for example OHYr05 (SEQ ID NO:26) and OHYr23 (3p10L; SEQ ID NO:37), while other RNA molecules, such as OHYr 22 (SEQ ID NO:45) and OHYr12 (SEQ ID NO:33) were unable to activate RIG-I (FIG. 4). The sequence information of all RNAs used is indicated in Table 1 above.

Table 2 shows the Kcat, Km and Kcat/Km values for ATPase activity of mmRIG-I binding to different immRNAs.

TABLE 2

Kcat, Km and Kcat/Km values for different immRNAs

| RNA | RNA alternative name | Kcat (s$^{-1}$) | Km (μM) | Kcat/Km (s$^{-1}$ μM$^{-1}$) |
|---|---|---|---|---|
| OHYr21 | 3p10La | 2.931 ± 0.1607 | 157.5 ± 36.42 | 0.01861 ± 0.004412 |
| OHYr22 | 3p10Lb | 0 | — | — |
| OHYr05 | 3p10LG9 | 4.611 ± 0.3214 | 268.4 ± 71.11 | 0.01718 ± 0.00452 |
| OHYr16 | 3p10LA9 | 5.011 ± 0.2365 | 322.5 ± 55.64 | 0.015538 ± 0.004251 |
| OHYr17 | 3p10LU9 | 2.024 ± 0.1081 | 114.1 ± 27.22 | 0.017739 ± 0.003971 |
| OHYr18 | 3p10LC9 | 2.265 ± 0.09866 | 172.4 ± 31.14 | 0.013138 ± 0.003168 |
| OHYr12 | 3p6L | 0 | — | — |
| OHYr09 | 3p8L | 1.079 ± 0.09041 | 83.93 ± 33.13 | 0.012856 ± 0.002729 |
| OHYr20 | 3p9L | 1.804 ± 0.09874 | 114.6 ± 27.98 | 0.015742 ± 0.003529 |
| OHYr23 | 3p10L | 5.913 ± 0.3979 | 237.3 ± 62.23 | 0.024918 ± 0.006394 |
| OHYr03 | 3p11L | 4.472 ± 0.3416 | 233.8 ± 69.83 | 0.019127 ± 0.004892 |
| OHYr13 | 3p14L | 3.466 ± 0.208 | 196.1 ± 47.62 | 0.017675 ± 0.004368 |
| OHYr06 | 3p20L | 3.243 ± 0.1281 | 251.5 ± 38.28 | 0.012895 ± 0.003346 |
| OHYr07 | 3p12L | 3.634 ± 0.1946 | 151.9 ± 34.53 | 0.023924 ± 0.005636 |

Example 7: Interferon-Inducing Ability of Different immRNAs in Human Cells

Figure 5:
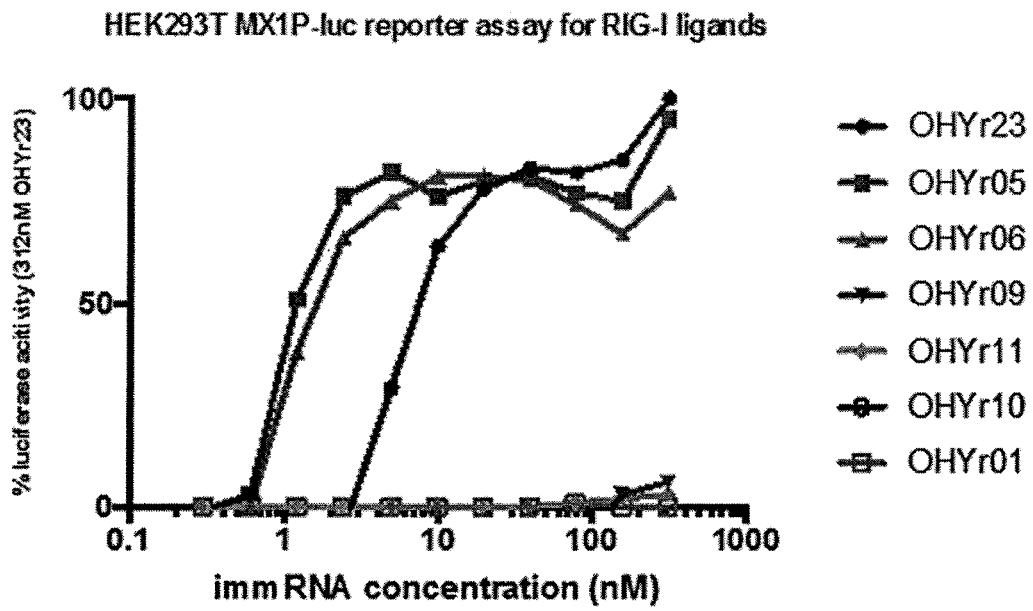
FIG. 5. Screening of immRNA constructs for their capacity to induce Type I IFN. A) RIG-I ligand immunomodulating RNA (immRNA) was transfected into HEK-293T cells that contain a stably integrated luciferase reporter driven by a MX1 promoter (MX1P-luc). RNA was transfected at various concentrations achieved by serial dilution (2×) and luminescence was measured 24 h after transfection. Results are represented as a percentage of the RLU measured for 312 nM treatment of OHYr23 (parental construct; SEQ ID NO:37). B) HEK293T cells expressing the MX1 promoter driving luciferase was transfected with OHYr23 at 10 nM. These cells were co-transfected with either OHYr10 (SEQ ID NO:30) or OHYr09 (SEQ ID NO:34) in a range of concentrations (0 nM-312 nM). Cells were lysed with Brightglo and luminescence was read. Error bars are for triplicate transfections per condition FIG. 6. Screening of immRNA constructs for their capacity to induce Type I IFN. ImmRNA was transfected into THP1-Dual™ cells which were derived from the human THP-1 monocyte cell line by stable integration of the lucia luciferase reporter driven by ISG 54. The luciferase reporter response was normalized to 100% and plotted against the log concentration of RNA. The EC50 value for OHYr05 (SEQ ID NO:26) was determined to be 3.47 nM as compared to OHYr23 (SEQ ID NO:37) with EC50 of 14 nM.
Figure 5:
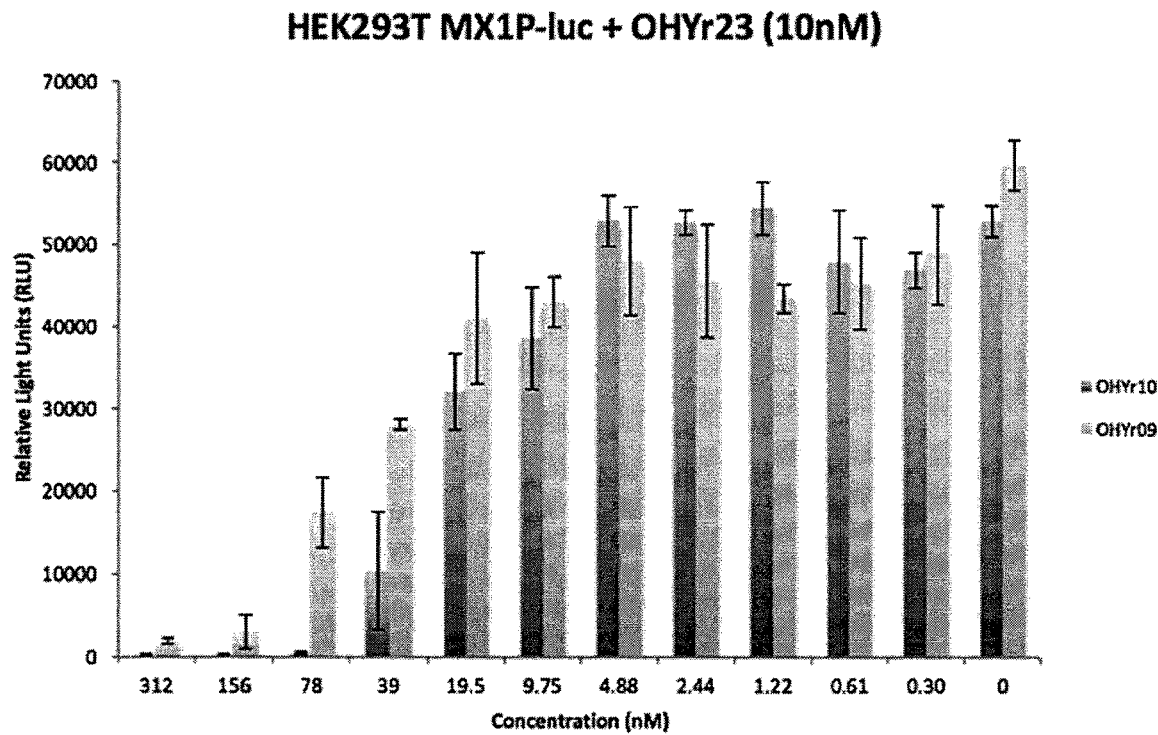
Figure 6:
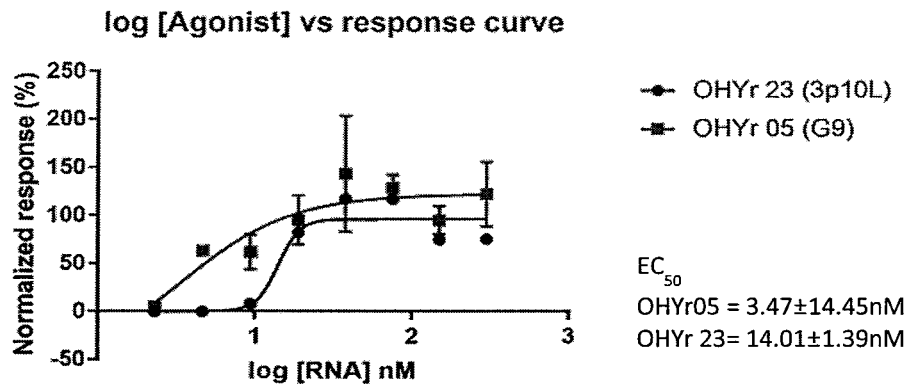
Figure 6:
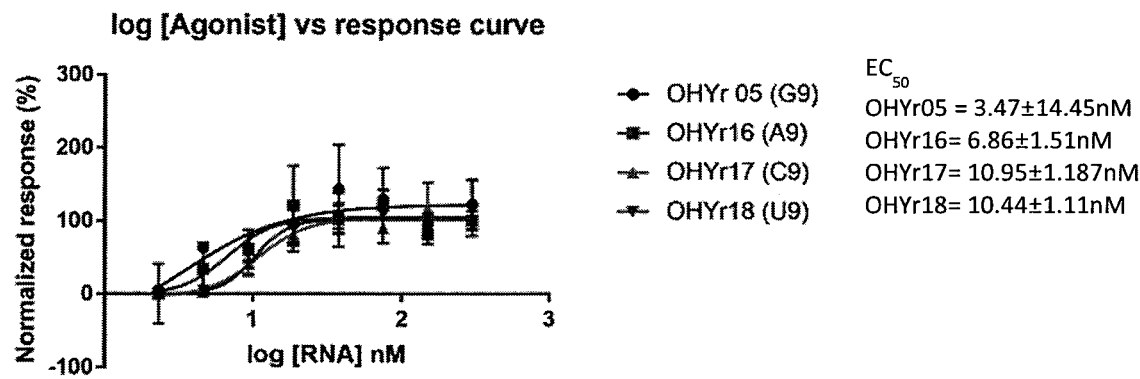
Figure 6:
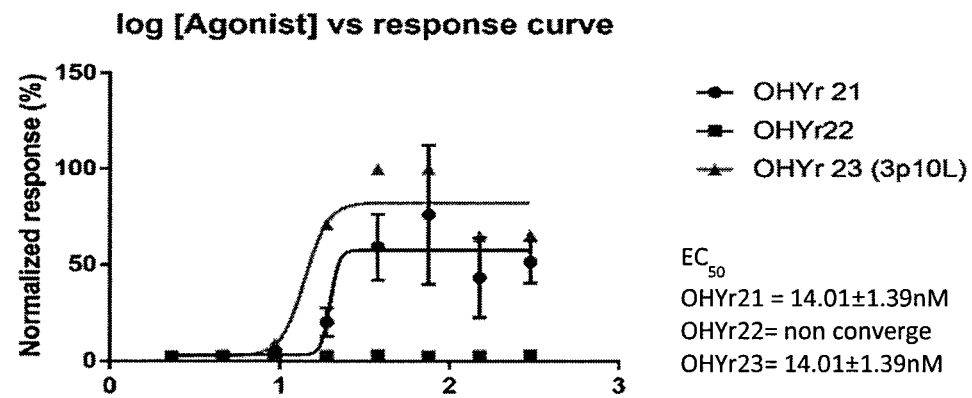
Figure 7:
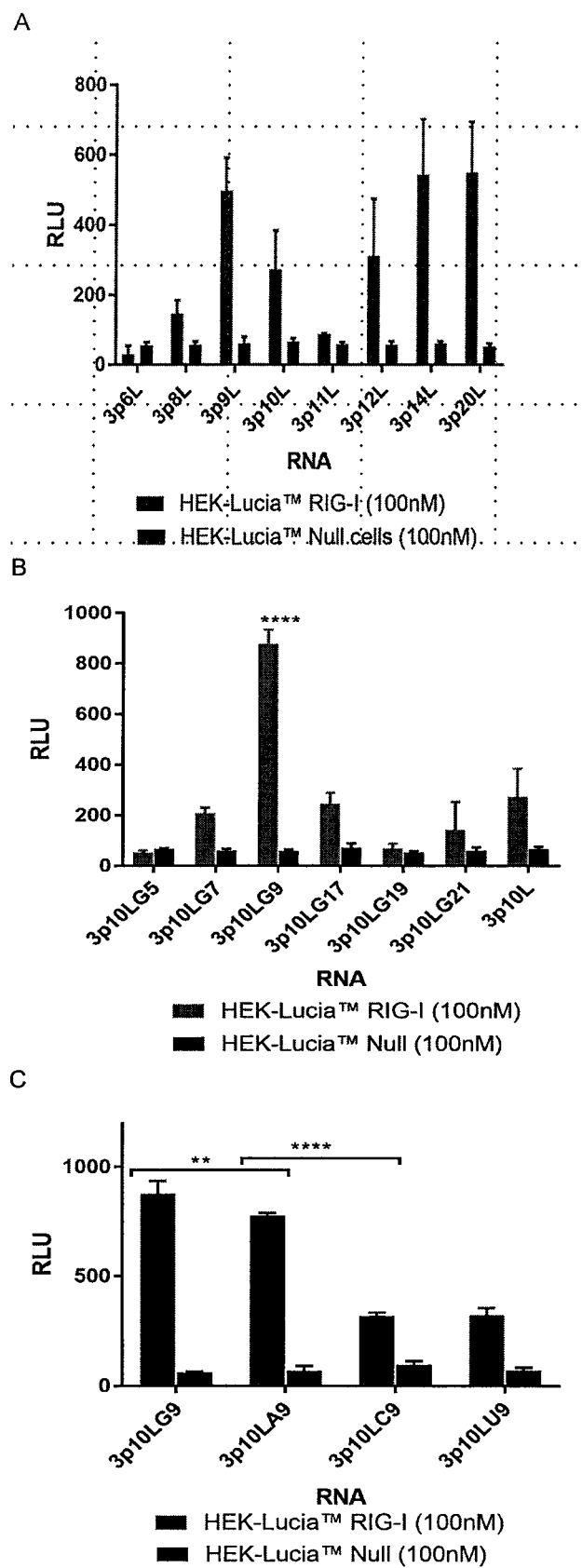
FIG. 7. Cell based assay with different ImmRNA in HEK-Lucia™ RIG-I and HEK-Lucia™ null. A) ImmRNA of different length, B) ImmRNA with different guanosine insertion. C) ImmRNA with different nucleotide at position 9. RNA of different length was transfected at a fixed concentration of 100 nM and luminescence was measured 24 hours post-transfection. Results are measured in triplicate and presented as RLU.
Figure 8:
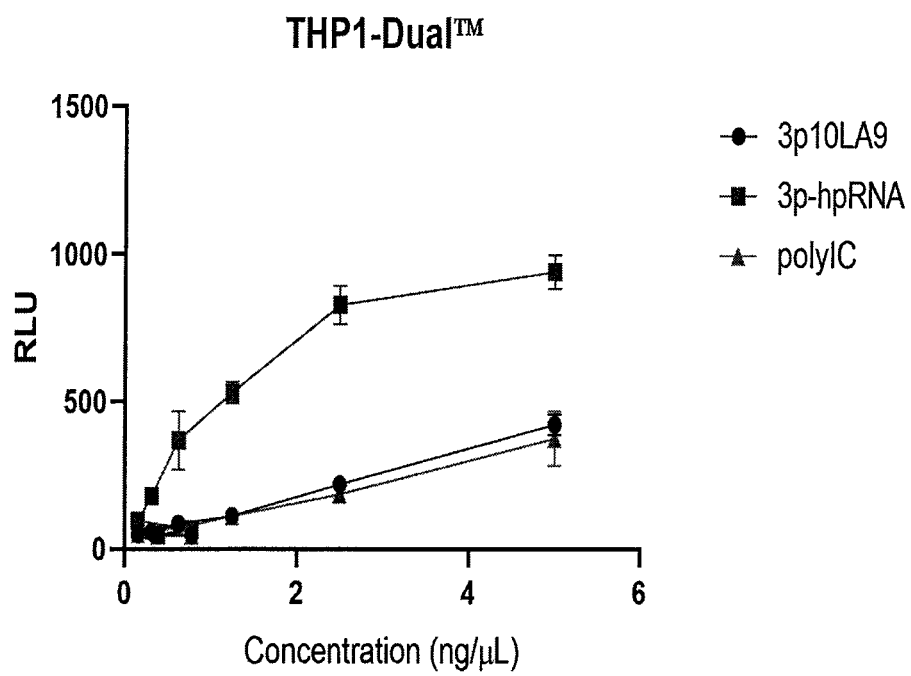
FIG. 8. Comparison between the activity of commercial RNA and ImmRNA OHYr16 (3p10LA9; SEQ ID NO:25) in A) THP1-Dual™ cells and B) HEK-Lucia™ RIG-I. RNAs of different concentration were transfected into both cells and were serially diluted 2×. The luminescence values were recorded 24 hours post transfection.
Figure 8:
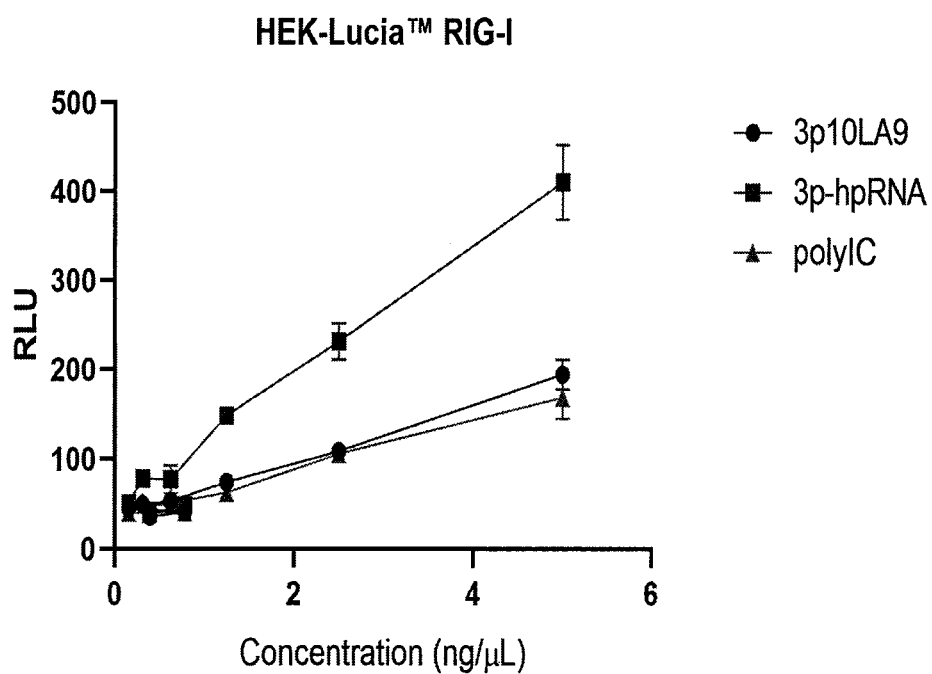

The biological function of immRNAs was tested in different assays. First, human embryonic kidney (HEK-293T) reporter cells were directly transfected using 293fectin as a transfection reagent. The luciferase reporter is driven by MX1, an IFN-stimulated gene downstream of interferon (IFN) β binding to the IFN-receptor. The previously published construct OHYr23/3p10L (SEQ ID NO:37) was used for comparison. Two constructs, OHYr05 and OHYr06 (SEQ ID Nos. 26 and 25; See Table 1) were found to have an almost 10-fold higher efficacy in inducing IFN production than OHYr23 (FIG. 5). The interferon inducing ability was also tested with THP1-Dual™ cells. THP1-Dual™ cells are derived from the human THP-1 monocyte cell line by stable integration of a luciferase reporter driven by ISG 54. The EC50 value for OHYr05 was lower as compared to OHYr23 which indicates that OHYr05 is able to elicit half maximal interferon response with a lower concentration of 3.47 nM (FIG. 6). Cell based assays to test ImmRNAs were also carried out using HEK-Lucia™ RIG-I cells (these are HEK-Lucia™ null cells expressing high levels of human Rig-I) and HEK-Lucia™ null cells (FIG. 7). Cells were transfected with 100 nM immRNA and for comparison two commercial RNAs poly I:C and 3p-hpRNA (InvivoGen) were included in the assay. 3p-hpRNA is an in vitro transcribed RNA sequence from Influenza A (H1N1) with a length of 87 nucleotide length. 3p-hpRNA is a RIG-I specific agonist (FIGS. 8a and b).

Figure 9:
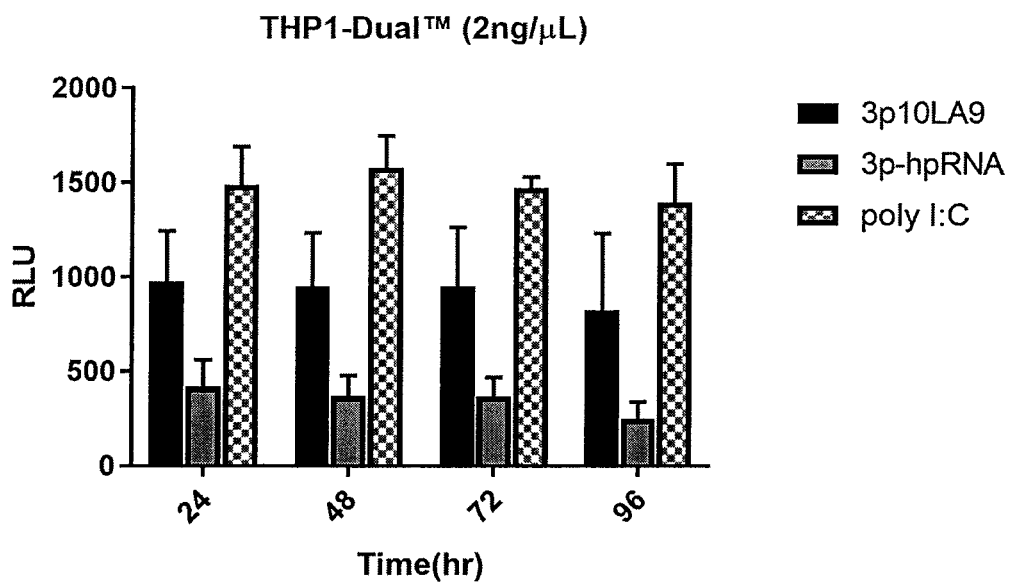
FIG. 9. Stability test for ImmRNA OHYr16 (3p10LA9; SEQ ID NO:25) and commercial RNAs in) THP1-Dual™ cells and B) HEK-Lucia™ RIG-I. RNAs were incubated in serum free medium for 24, 48, 72 and 96 hours prior to transfection into cells. The luminescence values were measured 24 hours post transfection.
Figure 9:
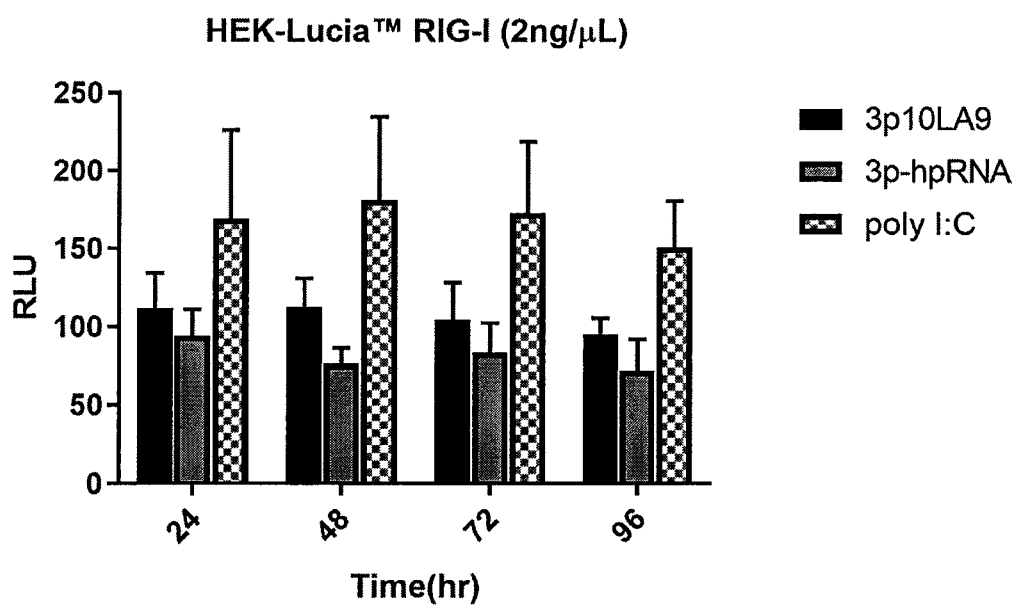

To test the stability of OHYr16, poly I;C and 3p-hpRNA, these RNA molecules were incubated in serum free medium for 24, 48, 72 and 96 hours at room temperature prior to transfection in the HEK-Lucia™ RIG-I cells and THP1-Dual™ cells. The RNAs tested were stable up to 96 hours in serum free medium (FIGS. 9a and 9b).

Example 8: Sequence Modifications Improving the Biological Activity of OHYr23

A number of sequence modifications to OHYr23 (SEQ ID NO:37) were made and their impact on biological activity were tested, using the MX1P luciferase reporter assay as a readout.

Change in Position and Nucleotide of the immRNA Kink (Nucleotide Insertion)

Figure 10:
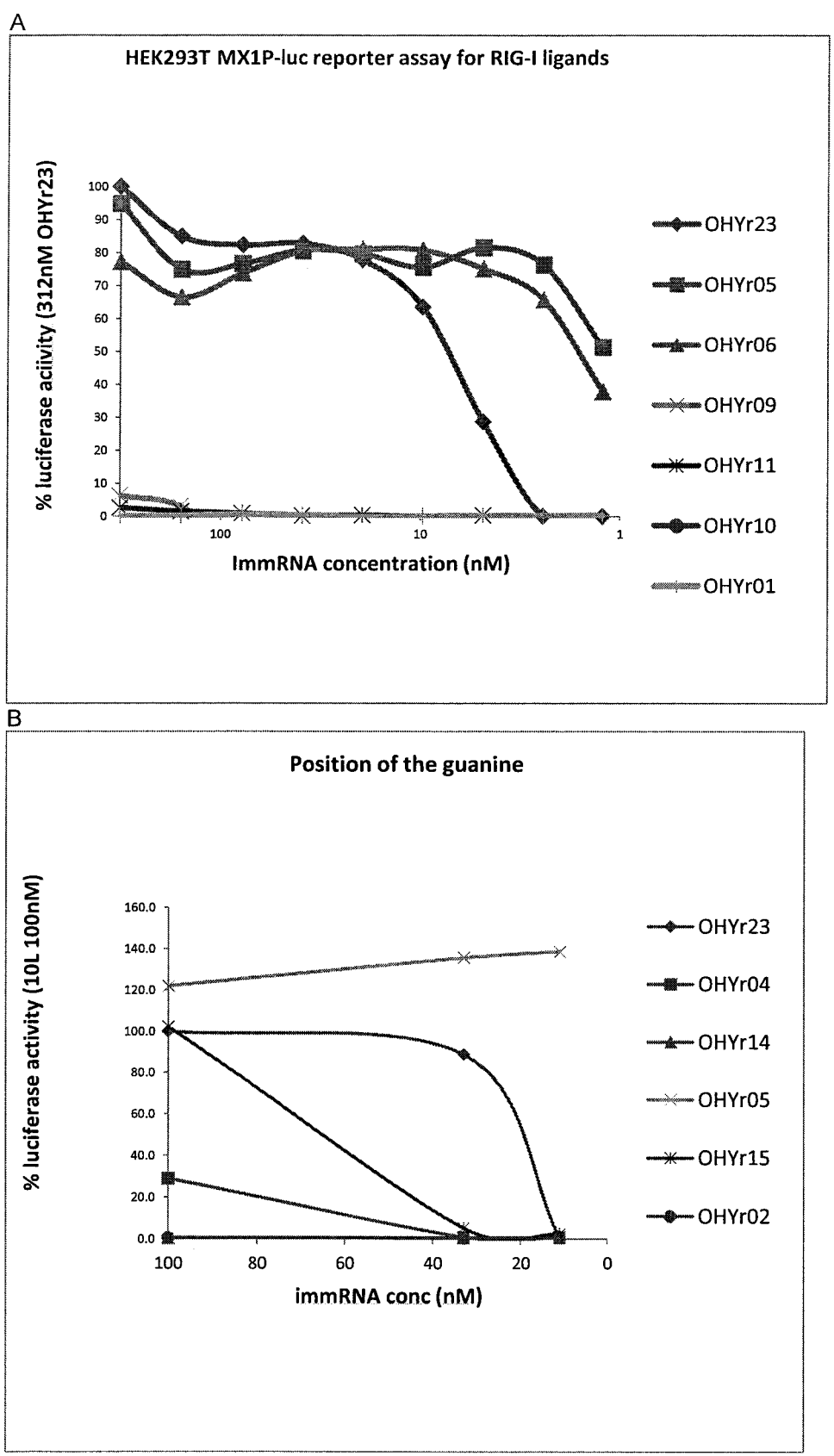
FIG. 10. Kink position of immRNA influences biological activity. A) A kink at nucleotide position 5 (OHYr10), position 19 (OHYr11) and position 21 (OHYr01) abrogates IFN production. % luciferase activity was normalized to the value detected from OHYr23 used at 312 nM. B) A kink on the 5' side of immRNA at position 9 from the stem (OHYr05) improved biological activity compare to no kink (OHYr23), whereas a kink at the 3' side of immRNA at position 9 counted from the stem (OHYr02) abrogated biological activity. % luciferase activity was normalized to the value detected from OHYr23 used at 100 nM. C) A purine at kink position 9 (Guanine in OHYr05 and Adenine in OHYr16) has a higher biological activity than a pyrimidine at kink position 9 (Uracil in OHYr17 and a Cytosine OHYr18). Directly transfected HEK293T MX1P-luc reporter cells were used as a readout in A-C.
Figure 10:
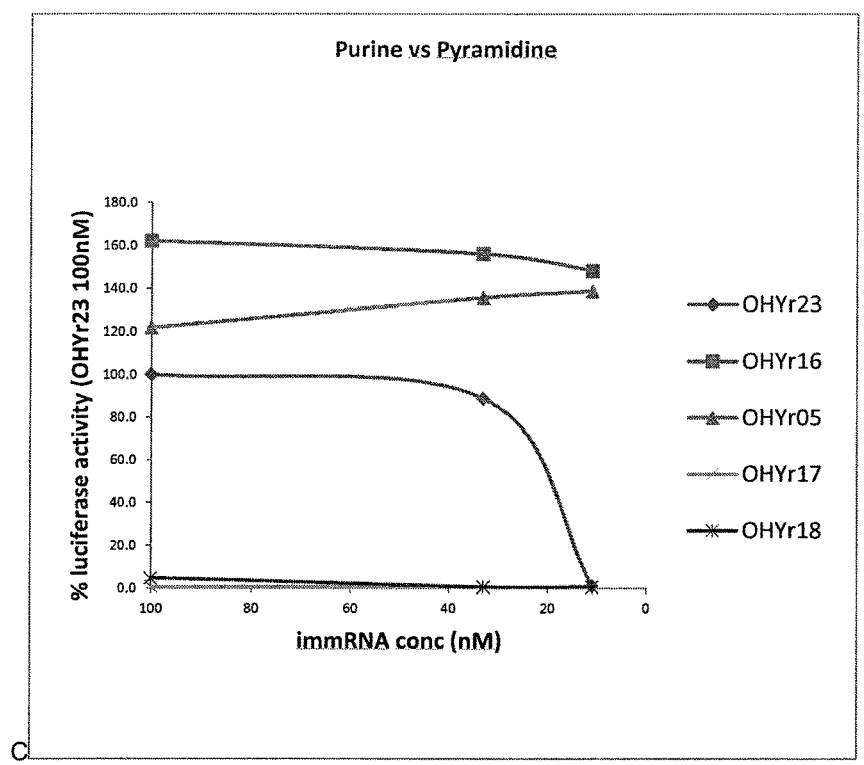

OHYr23 (SEQ ID NO:37) does not have a kink. However, OHYr05 (SEQ ID NO:26), which is more potent in IFN induction than OHYr23 has a kink created by the addition of a guanine on one side of the stem. It was tested whether the position of the kink has an impact on immRNA function. It was found that a kink closer to the stem end, including at nucleotide position 5 (OHYr10; SEQ ID NO:30), at position 19 (OHYr11; SEQ ID NO:31) and position 21 (OHYr01; SEQ ID NO:27) decreased IFN production (FIG. 10A). Hence, a kink at nucleotide position 9 or higher from the stem is preferred to increase biological function. Furthermore, a kink at the 5' side of the hairpin performs better than a kink on the 3' side of the hairpin at the same distance from the stem (compare OHYr02 with OHYr05) (FIG. 10B).

Next it was assessed whether the biological activity of the immRNA was affected by the nature of the nucleotide at the kink position. It was found that purine at kink position 9 (Guanine in OHYr05 and Adenine in OHYr16) works better than a pyrimidine at kink position 9 (Uracil in OHYr17 and a Cytosine OHYr18) (FIG. 10C).

Impact of the Length of the immRNA Stem on Innate Immune Activation

Figure 11:
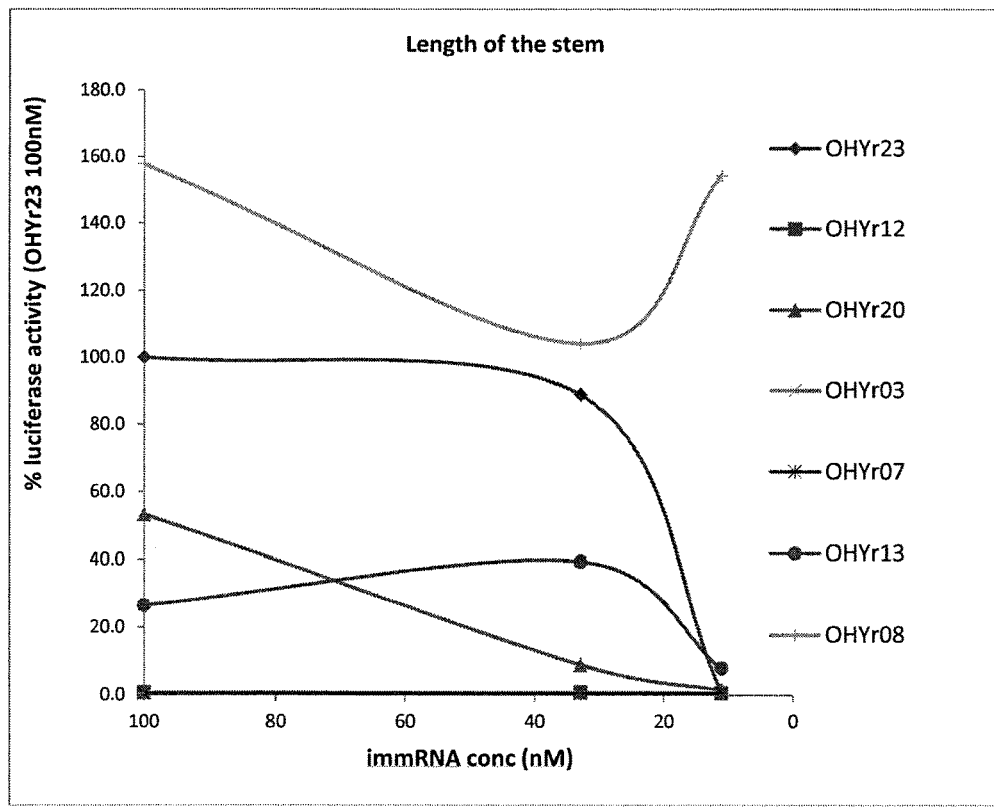
FIG. 11. Length of stem influences biological activity of immRNA. OHYr23 (length 10 nucleotides) and OHYr08 (length 30 nucleotides) have high activity in a HEK293T MX1P-luc reporter assay. In contrast, OHYr12 (length 6 nucleotides), OHYr20 (length 9 nucleotides), OHYr03 (length 11 nucleotides), OHYr07 (length 12 nucleotides) and OHYr13 (length 14 nucleotides) showed low or no biological activity. % luciferase activity was normalized to the value detected from OHYr23 used at 100 nM. Directly transfected HEK293T MX1P-luc reporter cells were used as a readout in A-C.

In order to find out how immRNA stem length affects binding to RNA-binding molecules and subsequent downstream signals we compared immRNA of various length. As shown in FIG. 11A, OHYr05 with a length of 10 nucleotides has the highest activity. High activity was also found for OHYr23 (length 10 nucleotides, FIG. 11), OHYr06 (length 20 nucleotides, FIG. 10A) and OHYr08 (length 30 nucleotides, FIG. 11). In contrast, shorter constructs OHYr12 (length 6 nucleotides) and OHYr20 (length 9 nucleotides), and longer constructs OHYr03 (length 11 nucleotides), OHYr07 (length 12 nucleotides) and OHYr13 (length 14 nucleotides) showed low or no biological activity (FIG. 11).

These data show that stem length in units of 10 nucleotides are the biologically most active species and that shorter stems or longer stems outside of the 10 nucleotide unit rule are less active.

Example 9: Anti-Viral Effect of immRNA in Human Cells

Figure 12:
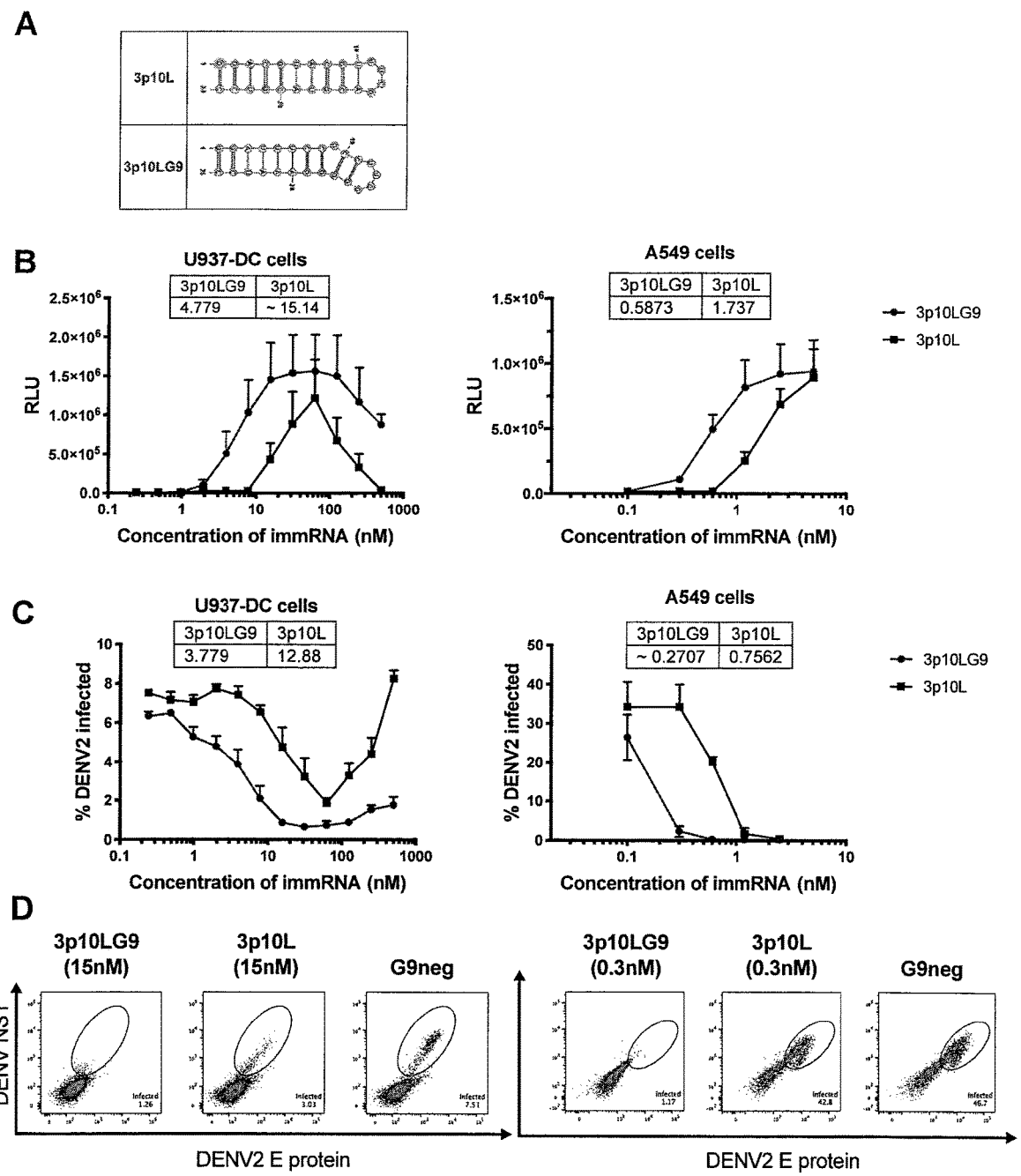
FIG. 12. 3p10LG9 (SEQ ID NO:26) induces an interferon response and is effective as prophylaxis against DENV-2 infection in both U937-DC-SIGN cells and A549 cells. (A) Structure and sequence of 3p10L (SEQ ID NO:37) and 3p10LG9 (SEQ ID NO:26) are as shown in the table. (B) 3p10L, 3p10LG9 (SEQ ID NO:26) or G9neg (SEQ ID NO:26 without 5' phosphorylation) was transfected into U937-DC-SIGN or A549 cells. Supernatants were harvested and incubated on ISRE-luc HEK-293T reporter cells. Luminescence was measured 6 h after incubation with the supernatant. Tables show EC50 values (nM) for 3p10L (SEQ ID NO:37) and 3p10LG9 (SEQ ID NO:26). (C) Transfected cells were infected with DENV-2 (TSV01) at MOI-1 and stained with antibodies binding NS1 and the E-protein (4G2) 24 h after infection. Tables show EC50 values (nM) for 3p10L (SEQ ID NO:37) and 3p10LG9 (SEQ ID NO:26). (D) Representative flow cytometry graphs for infected U937-DC-SIGN cells (left) or A549 cells (right) are shown. For U937-DC experiments: symbols are means±SEM, n=6 from two independent experiments. For A549 experiments: symbols are means±SEM, n=4 from two independent experiments. Statistical significance for luciferase assay and infection assay in (B) and (C) were calculated for U937-DC (p=0.013, p<0.0001) and A549 (p=0.0058, p<0.0001), respectively, using ordinary two-way ANOVA.

Induction of IFN is one of several antiviral defense strategies of cells. To test whether immRNA-induced anti-viral effector mechanisms could block subsequent infection, U937-DC-SIGN cells (monocytic cells stably expressing DC-SIGN) and human lung fibroblast cell line A594 were transfected with 3p10LG9/OHYr05 (SEQ ID NO:26) or 3p10L/OHYr23 (SEQ ID NO:37) (FIG. 12A) and subsequently infected with DENV (FIG. 12B). As a negative control the 3p10LG9 construct without 5' phosphorylation was used (G9neg). The percentage of infected cells was quantified by flow cytometry using E-protein- and NS1 protein-specific fluorescently labeled antibodies to detect infection intra-cellularly. In both human cell lines, 3p10LG9 activated the IFN response more efficiently than 3p10L in a dose-dependent manner.

To determine if immRNA was able to inhibit DENV infection we transfected U937-DC-SIGN cells and A549 cells with 3p10L and 3p10LG9 and infected the cells with DENV-2 24 h post-transfection. The percentage of infected cells was quantified by flow cytometry using E-protein- and NS1 protein-specific fluorescently labelled antibodies to detect intracellular viral proteins. In both U937-DC-SIGN and A549 cells, 3p10LG9 and 3p10L reduced DENV infection in a dose-dependent manner, with 3p10LG9 was more potent that 3p10L (FIGS. 12C and 12D). Interestingly, transfection of U937-DC SIGN cells with more than 62 nM of either immRNA resulted in a reduced efficacy of type I interferon production and diminished anti-viral effects. Overall these results show that 3p10LG9 has a greater potency compared to 3p10L in inducing IFN signalling and anti-viral response against DENV2 infection in U937-DC and A549 human cell lines.

Example 10: Innate Immune Activation (Adjuvant Effect) in Ex Vivo Human Antigen-Presenting Cells Antigen presenting cells (APCs) comprising dendritic cells and macrophages are essential mediators for the generation of adaptive immune responses and immune memory. After an infection or vaccination, APCs are activated by pathogen-associated molecular patterns (PAMPs) that bind to pathogen recognition receptors (PRRs) on the surface or inside APCs. RNA binding molecules RIG-I and MDA5 are examples of PRRs that can be specifically targeted to activate APCs. To test the potential of immRNA to activate primary human cells via RIG-I human skin was used as a model organ. Skin (from mastectomy surgery) is one of the few organs that are accessible for human studies and is very valuable because it contains large numbers of dendritic cell subsets and macrophages, representative of the APC populations in human tissue in general.

Healthy skin samples were processed to prepare single cell suspensions that could be used for transfection with immRNA and for downstream analysis. The method of skin cell preparation and infection with DENV has been described previously (Cerny et al. (2014), PLoS Pathog. 2014; 10(12):e1004548). CD14$^+$ dermal dendritic cells (DDCs), CD11c$^+$ DDCs, CD141$^+$ DDCs and Langerhans cells (LCs) were distinguished by a stain and gating strategy.

Figure 20:
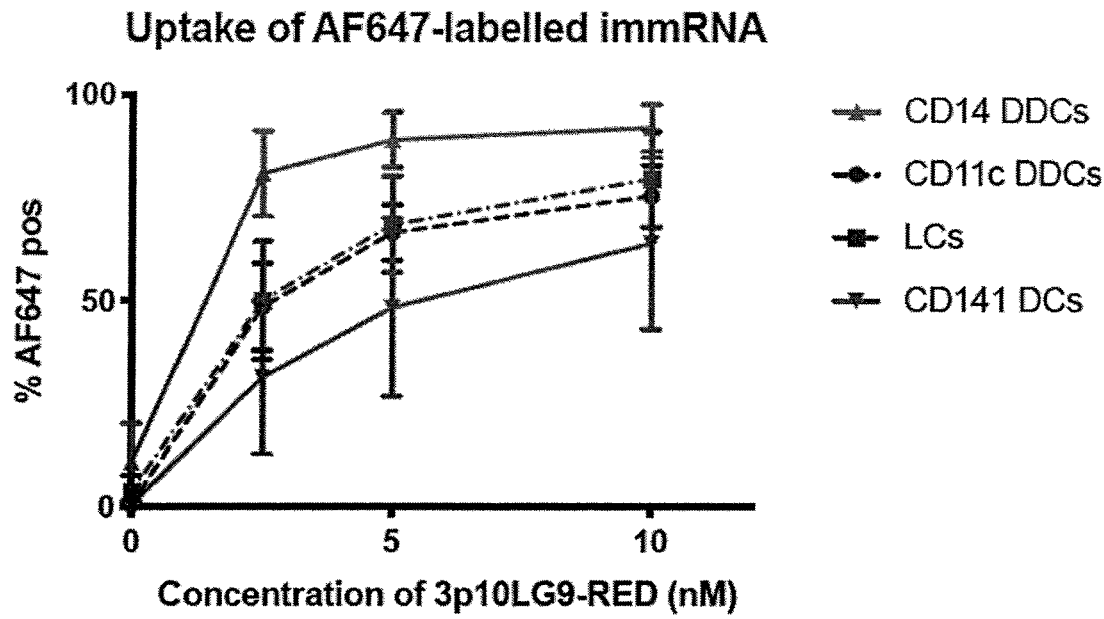
FIG. 20. 3p10LG9 uptake by primary human skin cells. Skin cells were transfected with various concentrations of 3p10LG9 labelled with Alexa-Fluor 647. Cells were analysed using flow cytometry 24 h post-transfection. Statistical significance between the different cell types with varying concentrations of 3p10LG9-red was calculated using repeated measures two-way ANOVA (p=0.0026), symbols show means±SD, n=3.

Efficient DENV infection of DCs in the skin suggests their important role in the systemic spread of DENV. Infected DCs could carry the virus from the site of infection to secondary lymphoid organs such as lymph nodes. To test whether immRNA could block infection of primary human skin cells, healthy skin samples were processed to prepare single cell suspensions for transfection with immRNA and subsequent flow cytometry analysis (Cerny et al., supra). It was first tested which cells were most efficiently transfected with immRNA using a fluorescently labelled version of 3p10LG9 (3p10LG9-RED) that can be traced by flow cytometry. All cell types were transfectable and uptake was most efficient in CD14$^+$ DDCs, followed by CD11c$^+$ DDCs and Langerhans cells, with CD141$^+$ DDCs having the least efficient uptake. When immRNA-RED was added to the cells without transfection reagent the uptake was minimal, demonstrating that immRNA uptake by phagocytosis was minimal (FIG. 20).

First, it was tested which cells are most efficiently transfected using a fluorescently labeled version of OHYr05 (OHYr5-RED) that can be traced by flow cytometry. All cell types were transfected but uptake was most efficient in MPs, CD14$^+$ DDCs, and CD11c$^+$ DDCs (data not shown). If immRNA-RED is added to the cells without transfection reagent the uptake was minimal, demonstrating that immRNA uptake by phagocytosis is minimal.

Figure 13:
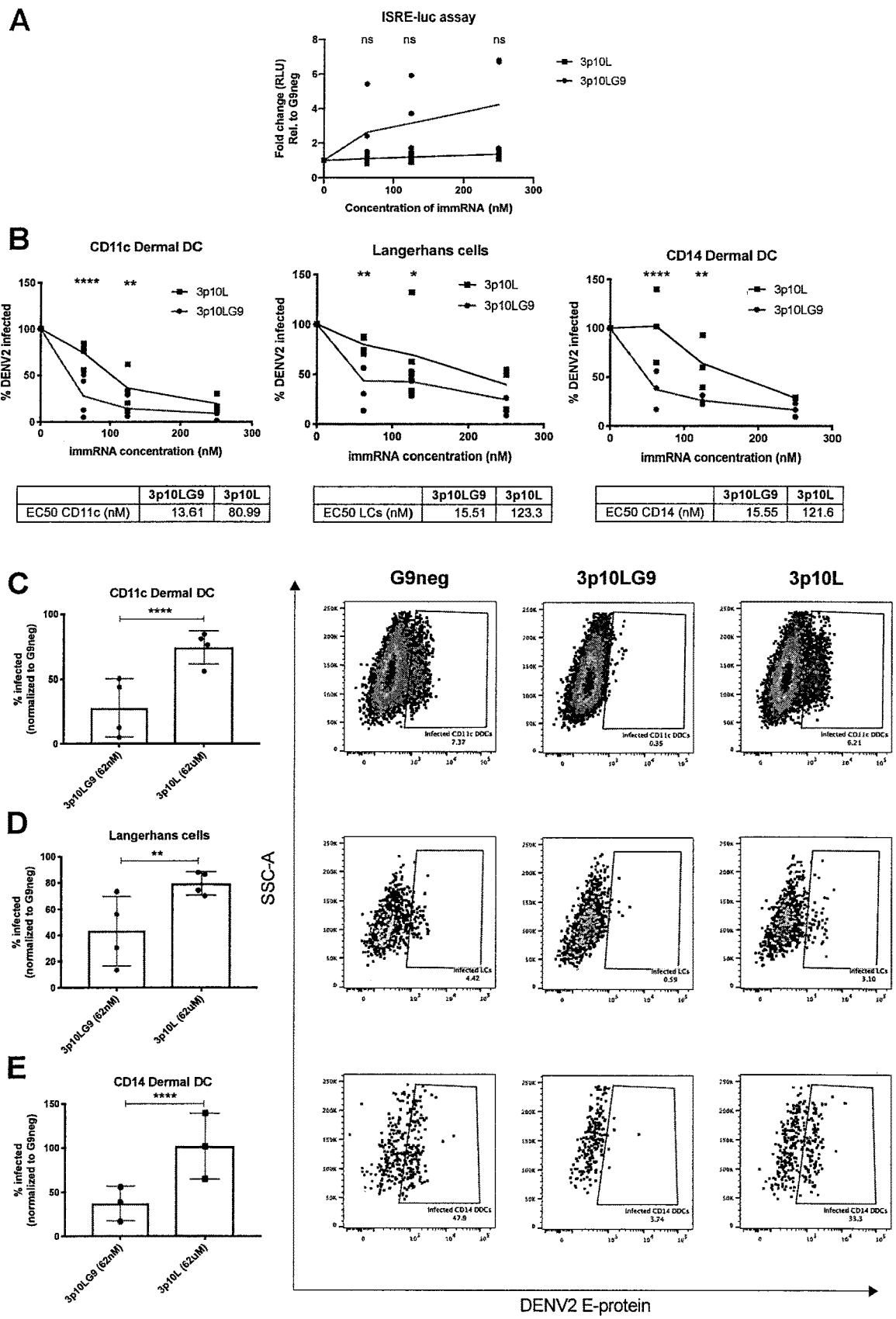
FIG. 13. 3p10LG9/OHYr05 (SEQ ID NO:26) has a higher efficacy as a prophylaxis against DENV-2 infection compared to 3p10L/OHYr23 (SEQ ID NO:37) in primary human skin DCs. (A) Human skin DCs were transfected with 250 nM, 125 nM and 62 nM of 3p10LG9 (SEQ ID NO:26) or 3p10L (SEQ ID NO:37) and incubated for 24 h. Supernatant was incubated on HEK-293T cells containing a luciferase reporter driven by Interferon-stimulated Response Element (ISRE-luc) and luminescence was measured after 6 h (right panel). Results are presented as fold change compared to G9neg (SEQ ID NO:26 without 5' phosphorylation). Each symbol represents a sample from one donor. Statistical significance (p<0.05) was determined using a two-way ANOVA with Dunnett's multiple comparisons test (ns: not significant). (B) Human skin DCs transfected with 250 nM, 125 nM and 62 nM of 3p10LG9 (SEQ ID NO:26) or 3p10L (SEQ ID NO:37) for 24 h were infected with DENV-2 at MOI 5 for 48 h. Flow cytometry was used to quantify the percentage of DENV-2 infected cells in each subpopulation of skin DCs by intracellular staining with 4G2 antibody. Percentage of cells infected for each condition was normalized to G9neg (SEQ ID NO:26 without 5' phosphorylation). (C-E) Percentage of infected cells for each subpopulation of skin DCs taken from the data plotted in (B) after transfection with 62 nM of 3p10LG9 (SEQ ID NO:26) or 3p10L (SEQ ID NO:37) (left), and representative flow cytometry (right). (C) CD11c DDCs, (D) Langerhans cells, (E) CD14 DDCs. Each symbol represents one donor. Bars show means±SD. Statistical significance (p<0.05) was determined using a two-way ANOVA with Dunnett's multiple comparisons test (* P≤0.05,  P≤0.01, * P≤0.005).

Example 11: Prophylactic and Therapeutic Anti-Viral Effect of immRNA in Ex Vivo Human APCs It was tested whether human skin APCs treated with immRNA were protected from DENV infection. For this skin single cell suspensions were treated with 250 nM, 125 nM and 62 nM of OHYr05 (SEQ ID NO:26), OHYr23 (SEQ ID NO:37) and OHYrNEG (SEQ ID NO:26 without 5' phosphorylation) and subsequently, after 24 h the supernatants were collected for ISRE-luciferase assay and the cells infected with DENV at MOI 5. 48 h after infection the cells were stained for flow-cytometry based quantification of infection (Cerny et al., supra). Prophylactic treatment of human skin APCs with 3p10LG9 induced type I IFN more efficiently compared to those treated 3p10L, based on the ISRE-luciferase assay (FIG. 13A). Prophylactic treatment of human skin APCs with immRNA also protected the cells from DENV infection in a dose-dependent manner. EC50 values showed 3p10LG9 was more potent in inducing anti-viral response compared to 3p10L in CD11c$^+$ DDCs (3p10LG9: 13.6 nM, 3p10L: 81.0 nM), LCs (3p10LG9: 15.5 nM, 3p10L: 123.3 nM) and CD14$^+$ DDCs (3p10LG9: 15.5 nM, 3p10L: 121.6 nM) (FIG. 13B). At the lowest concentration tested (62 nM) 3p10LG9 was significantly more effective than 3p10L in reducing the number of infected CD11c$^+$ DDCs (p≤0.01) and CD14$^+$ DDCs (p≤0.05) (FIG. 13C-E).

Figure 14:
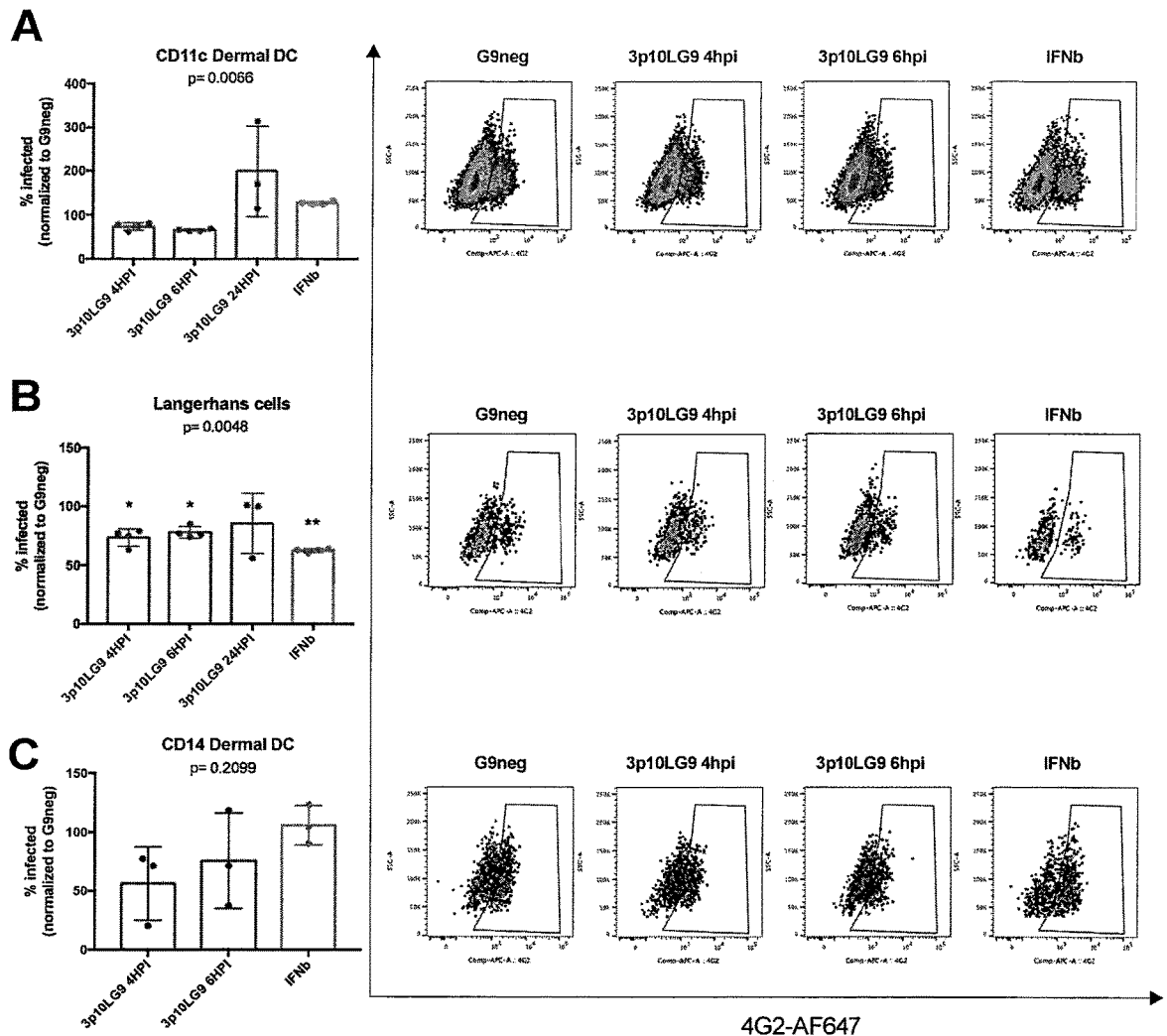
FIG. 14. ImmRNA 3p10LG9 has therapeutic effect against DENV-2 infection in Primary Human Skin DCs. (A-C) Human skin DCs were transfected with infected with DENV2 at MOI 5 and 62 nM of 3p10L (SEQ ID NO:37), 3p10LG9 (SEQ ID NO:26) or G9neg (SEQ ID NO:26 without 5' phosphorylation) was introduced at the respective time-points post-infection. The graph showing the percentage of infected cells within each subpopulation of skin DCs (left) is reflected by intracellular staining with 4G2 antibody, as represented by the FACS plots (right). Percentage of cells infected in each condition was normalized to G9neg control for that particular donor. (A) CD11c Dermal DCs, (B) Langerhans cells, (C) CD14 Dermal DCs. Each dot represents a sample from one donor. Statistical significance was determined using a one-way ANOVA with multiple comparisons (* P≤0.05,  P≤0.01, * P≤0.005).

To determine if immRNA can act as a therapeutic for DENV infected skin APCs, skin single cell suspensions were infected with DENV at MOI 5 and treated with 62 nM of 3p10LG9 4, 6 and 24 h after infection. Cells were stained 48 h after infection for flow-cytometry-based quantification of infection. Since the infection efficacy varied up to 40% between individual skin samples, the infection was normalized to the G9neg control from the 4 h post-infection time point. The inhibitory effect of 3p10LG9 overall was modest. A significant reduction of infected cells after treatment with 3p10LG9 was only seen in Langerhans cells, and only at early time points of 4 h and 6 h post-infection (FIG. 14B).

Small therapeutic effects were seen in the CD11c+ DDCs (FIG. 14A) and CD14+ DDCs (FIG. 14C) at the early timepoints. When treated 24 h after infection, the percentage of infected 3p10LG9-treated CD11c+ DDCs cells 48 h later tended to be higher compared to the G9neg-treated cells. Without wishing to be bound to any theory, it is possible that the virus inhibited the antiviral response more efficiently in this cell subset, subverting the activity of RIG-I ligand. Overall, these data suggest that 3p10LG9 had a modest therapeutic anti-viral effect on DENV-2 infection in primary human skin APCs.

Example 12: Adjuvant Activity of immRNA

Figure 15:
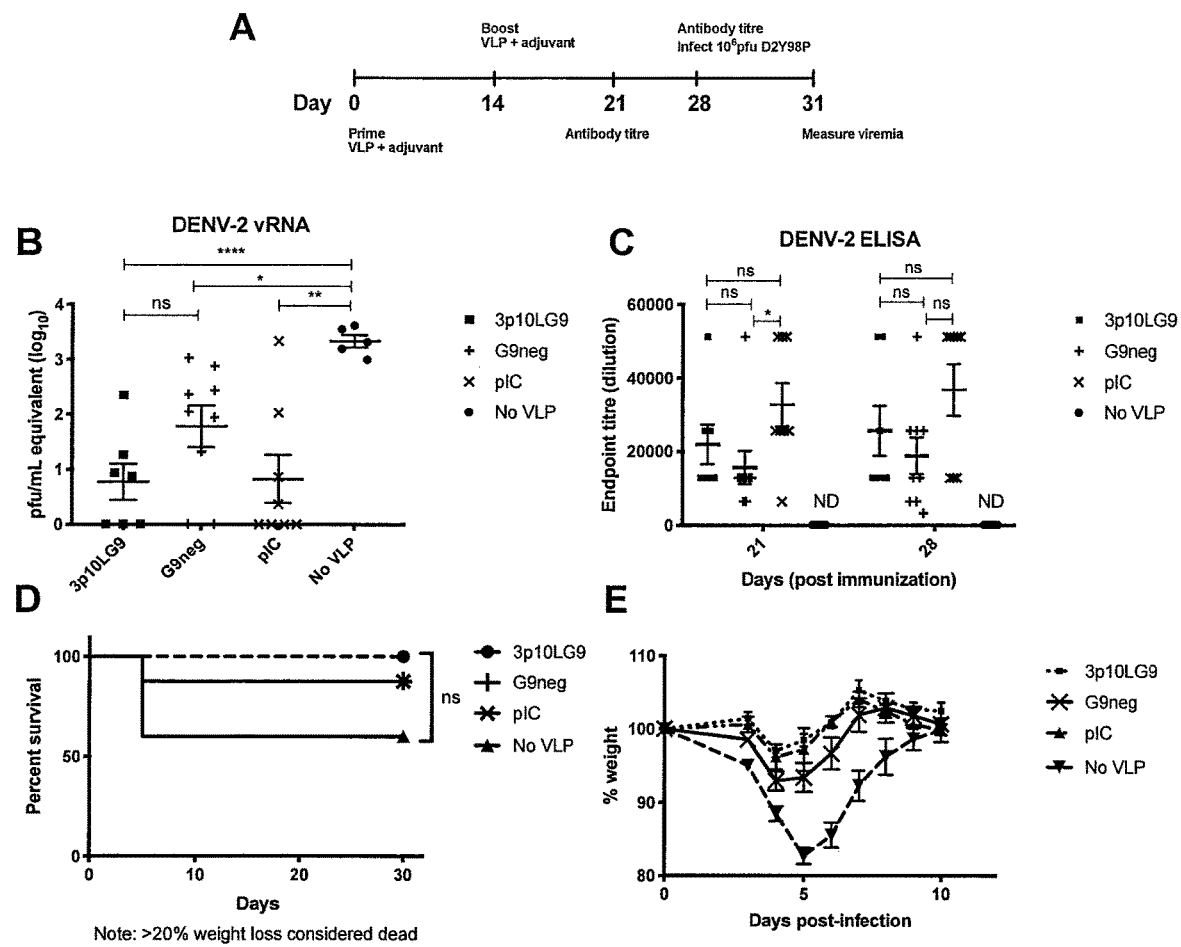
FIG. 15. ImmRNA enhanced antibody production and increase protection when used as an adjuvant with a DENV-2 VLP vaccine. 10 ug of DENV-2 VLP was injected with 25 ug immRNA mixed with in vivoJET-PEI or Poly I:C and injected intramuscularly into CD11c-cre-IFNAR$^{fl/fl}$ mice (Zust et al. (2014), J Virol. 88(13):7276-85). (A) Immunization and challenge schedule for vaccination experiments. (B) Viral RNA (vRNA) was extracted from plasma of DENV-2 VLP-vaccinated mice (n=5-9) infected with $10^6$ pfu of DENV-2. Taqman assay was done to determine the concentration of vRNA in the plasma. Bars show means±SEM. Statistical significance was determined using a student's t-test (* P≤0.05,  P≤0.01, ** P≤0.0001, ns: not significant). (C) Endpoint titre DENV-2 ELISA with plasma from DENV-2 VLP-vaccinated mice bled on day 21 and 28 post-vaccination. Bars show means±SEM. Statistical significance was determined using a student T-test (* P≤0.05, ns: not significant). (D) Survival curves were generated using the Kaplan-Meier method and significance of differences was calculated by using the log rank test (ns: not significant). (E) Weights were measured over a period of 6 days post-infection and plotted as % of initial weight. Mice with more than 20% weight loss considered moribund and were euthanized. Bars show means±SEM. Statistical significance was determined using a two-way ANOVA with multiple comparisons (P=0.0007).

RIG-I agonists as innate immune cell stimulators can be used as adjuvants for vaccines. To test the capacity of immRNA as vaccine adjuvant in vivo, mice were immunized with commercially available DENV-2 virus-like particles (VLP) mixed with 3p10LG9 (SEQ ID NO:26) by injection of the mixture with the transfection reagent JetPEI. As negative controls, VLP mixed with 3p10Lneg (3p10LG9 without tri-phosphate group at the 5'end) and VLP without adjuvant were used. As a positive control VLP was mixed with polyIC. 3p10LG9, when used as an adjuvant in combination with VLP, increased the antibody response to VLP compared to the formulation with G9neg (FIG. 15). Mice immunized with 3p10LG9-adjuvanted VLP had a reduced viral load compared to G9neg- and non-adjuvanted VLP-treated groups after challenge with dengue virus strain D2Y98P. Mice immunized with 3p10LG9-adjuvanted VLP also had a survival advantage compared to the non-adjuvanted VLP-treated group after challenge (FIG. 15).

Figure 16:
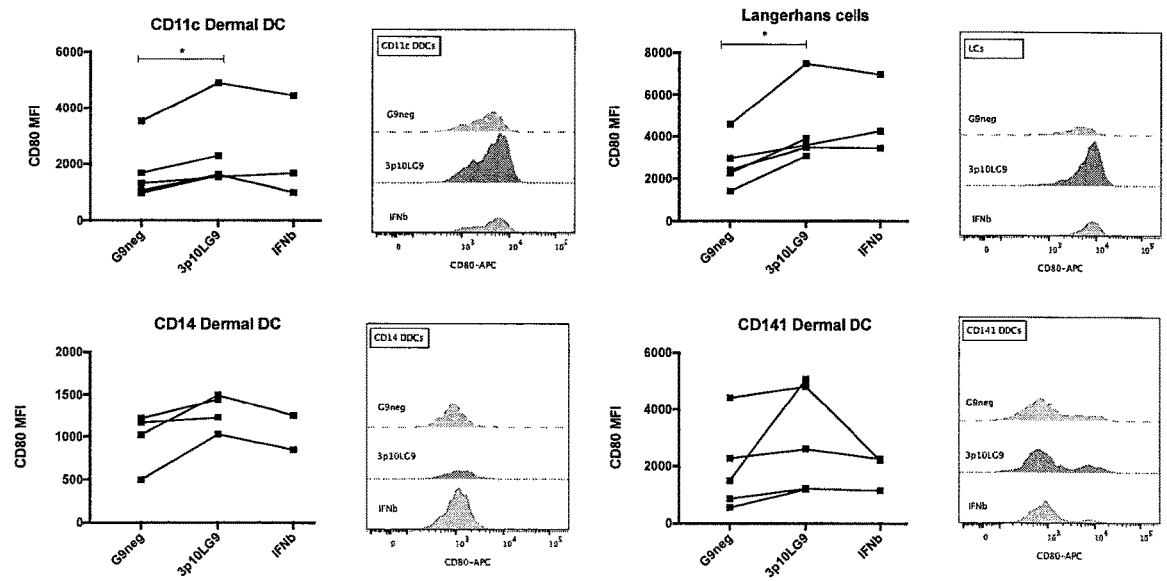
FIG. 16. 3p10LG9 (SEQ ID NO:26) increased expression of CD80 in primary human skin DC subsets. Primary human skin cells were transfected with 250 nM 3p10LG9 or G9neg, or treated with 1000 U recombinant human IFNβ as a positive control. After 72 h, the mean fluorescent intensity (MFI) of CD80 expression in each subpopulation of skin antigen-presenting cells was measured. Lines connect data points from individual donors (n=4). Statistical significance was determined using a paired student T-test (* P≤0.05).

In addition to the adjuvant activity in vivo, the adjuvant capacity of immRNA in human cells was also studied: For this experiment, human primary skin antigen-presenting cells were treated with immRNA to upregulate the immune-co-stimulatory molecule CD80 (FIG. 16).

Figure 17:
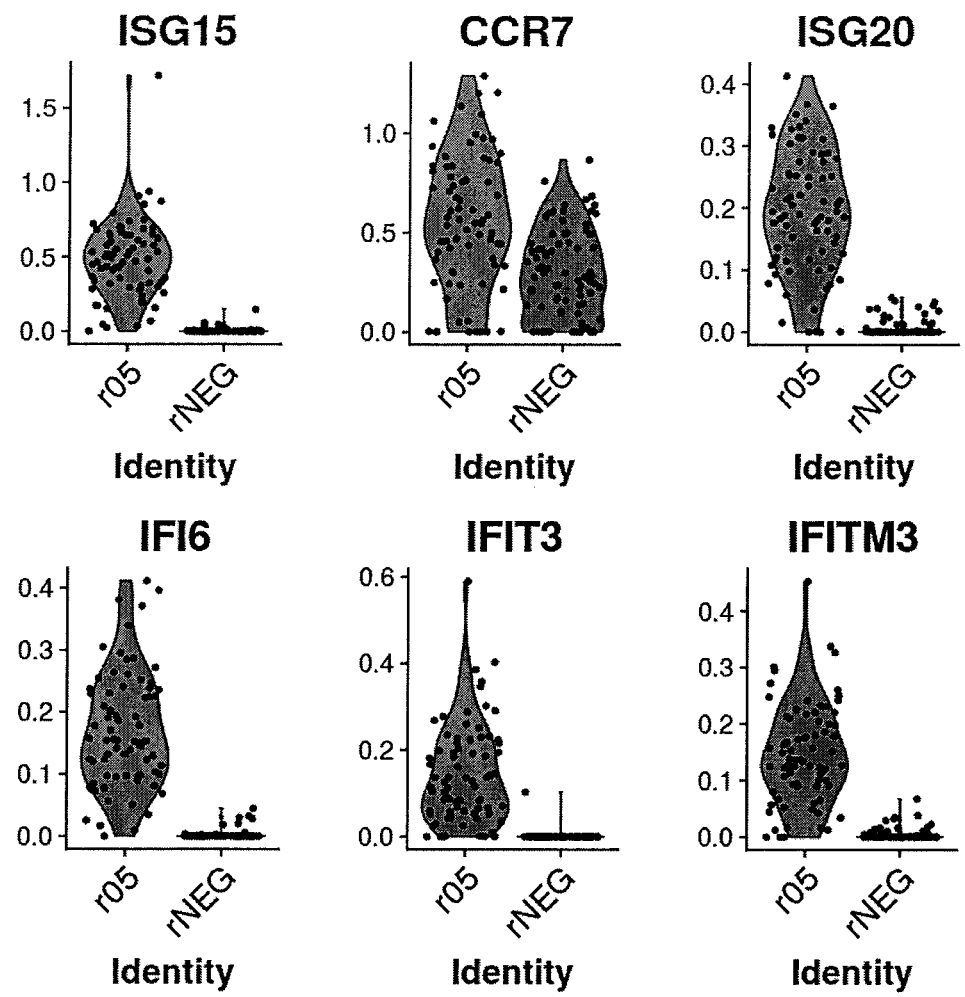
FIG. 17. immRNA induced innate immune gene upregulation in human antigen-presenting cells. Differentially expressed genes in antigen-presenting cells from human skin treated with r05 (SEQ ID NO:26) versus the same batch of cells treated with rNEG (SEQ ID NO:26 without 5' phosphorylation) were analyzed. Data points are from human CD11c+ DDCs, CD14+ cells, CD141+ DDCs and Langerhans cells. Each symbol represents one single cell. The cell's transcriptome was sequenced using single cell RNAseq SMART-seq v2 technology. Data show the top six DEGs when comparing r05 versus rNEG-treated cells. The y axis indicates fold change in gene expression in log 2 scale.

The activation profile of immRNA-treated was assessed by mRNA sequencing (RNAseq) of single and bulk-sorted skin APC subsets 35 h after transfection. Principal component analysis of differentially expressed genes (DEGs) in a total of 159 single APCs from one donor (combined CD11c+ DDCs, CD141+ DDCs, CD14+ cells and LCs) clearly separated 3G10LG9 and G9neg-treated cells. The six top down-regulated genes in 3G10LG9-treated cells included chemokine CXCL5 and cytokine IL-1B, and ribosomal proteins (data not shown). The six top up-regulated genes comprised five interferon-induced genes (ISG15, ISG20, IF16, IFIT3 and IFITM3) and immune cell-homing chemokine receptor CCR7 (FIG. 17). To further assess transcriptome changes after immRNA activation in more than one donor, bulk sorted skin APC subsets from five donors were sequenced. Similar to the single cell analysis, CD14+ cells were transcriptionally distinct from the other APC subsets (data not shown). Despite this, there was a high overlap of DEGs between cell types, showing that at least part of the immRNA-mediated activation was common to all skin APC subsets. At the same time, several of the twelve top DEGs identified in the single cell analysis were confirmed in the bulk cell analysis (data not shown). Heatmaps of DEGs selected based on a defined set of genes associated with anti-viral responses in host cells showed that various genes were upregulated for both 3p10LG9—and pIC-treated cells. However, 3p10LG9 appeared to be a generally stronger activator of anti-viral host response genes compared to pIC. This might be related to cell-type specific expression levels of RIG-I and TLR3, the ligands of immRNA and pIC. Ingenuity pathway analysis of DEGs per cell type revealed that the top three pathways were common for the individual APC subsets. However, other pathways were more cell type specific, such as the "role of RIG-I like receptors in antiviral innate immunity", which was more significant in CD141+ cells. In turn, this cell type was not associated with the antigen presentation pathway.

These data emphasized that immRNA efficiently activate anti-viral transcriptional programs in primary human APCs. This is important because APCs are known for their key roles in anti-viral responses during natural infection.

Example 13: ImmRNA-Mediated Viral Inhibition is RIG-I- and Type I IFN-Dependent

Figure 18:
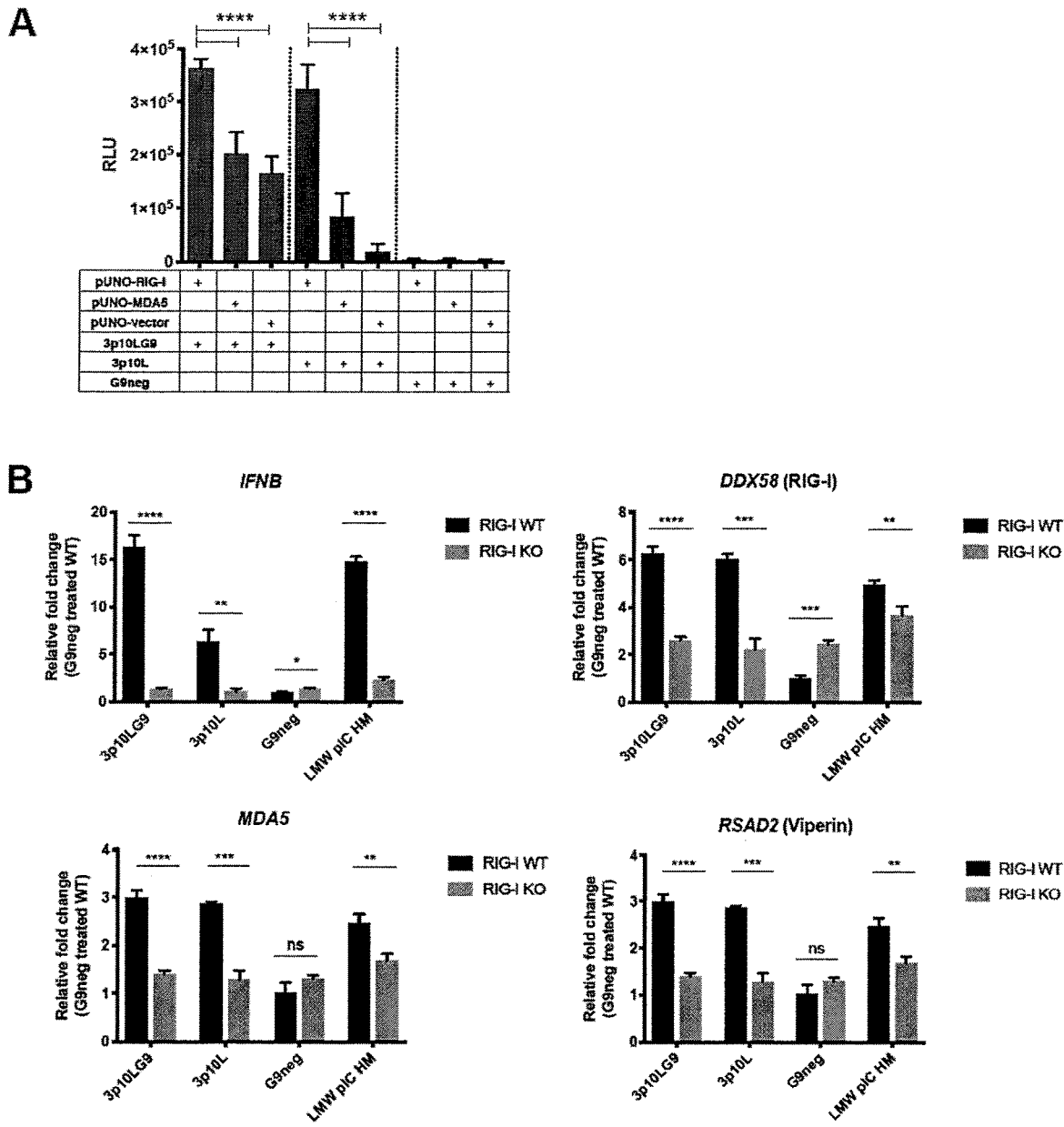
FIG. 18. The interferon signal induced by 3p10LG9 is RIG-I dependent. (A) HEK-293T cells were transfected with 50 ng of pUNO-hRIG-I or pUNO-hMDA5. These cells were then transfected with 10 nM of either 3p10LG9, 3p10L or G9neg. Supernatant from these transfected HEK-293T cells was incubated on the HEK-293T cells that contain a luciferase reporter driven by Interferon-Stimulated Response Element (ISRE-luc). Luminescence was measured 6 h after incubation with the supernatant. Bars shown means±SD. Statistical significance was determined using a one-way ANOVA test with multiple comparison (* $P \leq 0.05$,  $P \leq 0.01$, * $P \leq 0.005$). (B) 3p10LG9, 3p10L, G9neg or LMW poly I:C was transfected into either RIG-I knock-out U937-DC cells (KO) or the parental U937-DC cells (WT). Gene expression analysis on mRNA extracted from transfected U937-DC cells for IFNB, DDX58 (RIG-I), MDA5 and RSAD2 (Viperin): Data are represented as fold-change compared to the mean of G9neg-treated RIG-I WT sample. Bars show means±SD of triplicate transfections and data is representative of two independent experiments. Statistical significance was determined using a two-tailed student t-test (* $P \leq 0.001$, ** $P \leq 0.0001$).
Figure 19:
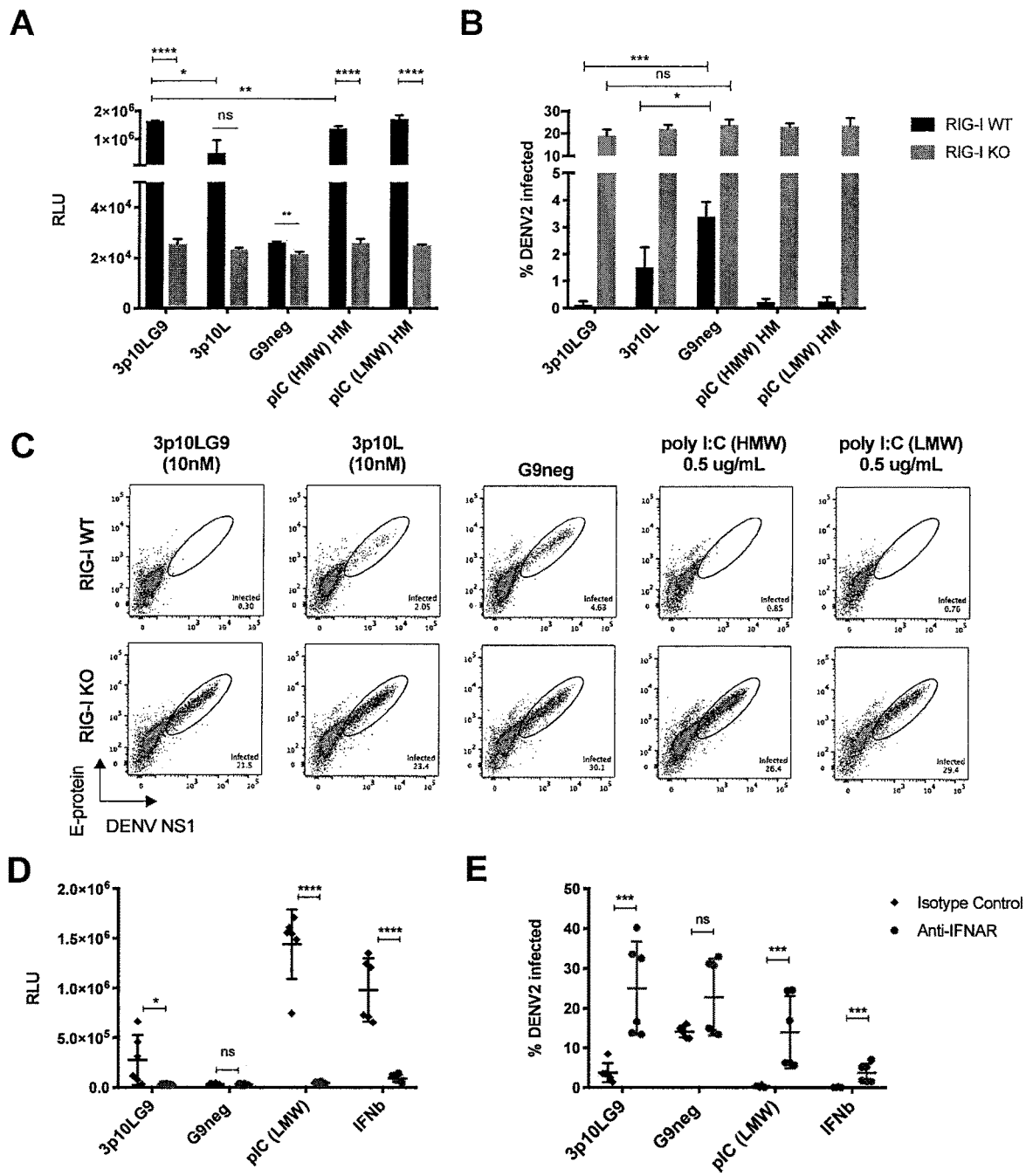
FIG. 19. Antiviral effects of 3p10LG9 are RIG-I and IFNAR signal-dependent. (A) Supernatants from U937-DC cells transfected with either immRNA or poly I:C were incubated on the HEK-293T cells that contain a luciferase reporter driven by Interferon-Stimulated Response Element (ISRE-luc). Luminescence was measured 6 h after incubation with the supernatant. Bars show means±SD of triplicate transfections and data are representative of two independent experiments. Statistical significance was determined using a two-tailed student t-test (* $P \leq 0.05$,  $P \leq 0.01$, * $P \leq 0.001$, **** $P \leq 0.0001$). (B) U937-DC cells pre-treated with either immRNA or poly I:C for 24 h were infected with DENV-2 TSV01 (MOI-1). Infected viable cells were quantified using flow cytometry with antibodies targeting NS1 and the E-protein fusion loop (4G2) 24 h after infection. Bars shown means±SD of triplicate transfections and data is representative of two independent experiments. Statistical significance between the treatment methods within each cell type was determined using a two-tailed student t-test (* $P \leq 0.05$, *** $P \leq 0.001$). (C) Representative FACS plots of viable U937-DC cells stained with antibodies targeting NS1 and the E-protein (4G2). HMW: high molecular weight, LMW: low molecular weight. (D) Anti-viral effects of 3p10LG9 are Type I interferon dependent. U937-DC SIGN cells were transfected with immRNA, poly I:C or treated with IFNß for 6 hours before the addition of 10 ug/mL of either anti-IFNAR blocking antibody or isotype control. Supernatant was collected after overnight incubation and was incubated on the HEK-293T cells that contain a luciferase reporter driven by Interferon-Stimulated Response Element (ISRE-luc). Luminescence was measured 6 h after incubation with the supernatant. Error bars shown are means±SD of triplicate transfections from two independent experiments. Statistical significance was determined using two-tailed student's t-test (* $P \leq 0.05$,  $P \leq 0.01$,  $P \leq 0.0001$). (E) U937-DC cells were infected with DENV-2 TSV01 (MOI-1). Infected viable cells were quantified using flow cytometry with antibodies targeting NS1 and the E-protein (antibody 4G2) 24 h after infection. Error bars show means±SD of triplicate transfections from two independent experiments. Statistical significance was determined using two-tailed student t-test (* $P \leq 0.001$, **** $P \leq 0.0001$).

It was experimentally tested whether short hairpin immRNA molecules bind to RIG-I and do not bind to MDA5. For this, the immRNA constructs were co-transfected with either RIG-I overexpressing plasmids or MDA5 overexpressing plasmids in HEK293T cells and it was found that 3p10LG9 activation of IFN signalling was significantly enhanced with RIG-I overexpression and this enhancement was greater when compared to MDA5 overexpression (FIG. 18A). Next, RIG-I knockout (RIG-I KO) U937-DC-SIGN cells using CRISPR-cas9 mediated gene knockdown with a gRNA designed to target exon 1 of human RIG-I were generated and these cells transfected with immRNAs and G9neg. Interferon stimulated gene (ISG) expression in RIG-I KO U937-DC SIGN cells was inhibited significantly after transfection with 3p10LG9 or 3p10L (FIG. 18B). This inhibition was observed despite a slightly increased IFNB transcript level in G9neg(control)-treated RIG-I KO cells compared to WT cells (1.3-fold increase). DDX58 transcript levels were still detectable despite the absence of the protein as the primers used in the RT-qPCR were designed to a region away from exon 1, which was the target region for disruption by the gRNA. DDX58 transcript levels were significantly higher in RIG-I KO G9neg control-treated cells compared to WT cells (2.4-fold). However, this increase in the baseline levels of ISGs in the RIG-I KO cells had no significant effects on type I interferon activation as there was no increase in the luciferase signal detected in the ISRE-luciferase assay (FIG. 19A). These results showed that 3p10LG9 was a more potent inducer of IFN-stimulated genes compared to the parental construct 3p10L, and that upregulation of IFN and ISGs was RIG-I-dependent. To determine if the antiviral effects were RIG-I dependent, WT and RIG-I KO U937-DC were prophylactically treated with either immRNA or poly I:C (Low Molecular Weight or High Molecular Weight) and the cells 24 h later infected with DENV-2. Type I interferon activity was only observed with WT and not with RIG-I knockout U937-DC cells (FIG. 19A). RIG-I KO U937-DC cells showed a significantly higher percentage of DENV-2 infection compared to WT U937-DC cells. When pre-treated with immRNA or poly I:C, DENV replication was significantly inhibited in the WT but not in the RIG-I KO U937-DC SIGN cells (FIGS. 19B and C), suggesting that the anti-viral effects observed were RIG-I dependent.

To determine if the anti-viral effects observed with 3p10LG9 were type I interferon dependent, U937-DC SIGN cells were transfected with 3p10LG9 and an interferon alpha receptor (IFNAR) blocking antibody was used to prevent IFN activation through type I interferon produced in response to RIG-I signalling. In the presence of anti-IFNAR antibody ISRE-induced luciferase signal was efficiently inhibited, demonstrating the functionality of the assay (FIG.

19D). Importantly, anti-IFNAR blocking antibody abolished the anti-viral effects of 3p10LG9 and DENV-2 replicated as efficiently as in G9neg-treated U937-DC SIGN cells (FIG. 19E). In summary, the experiments showed that the anti-viral effects observed in U937-DC SIGN cells treated with 3p10LG9 were RIG-I- and type I interferon signal dependent.

Example 14: Cytotoxic Effect of immRNA on Cancer Cell Line A549

Figure 21:
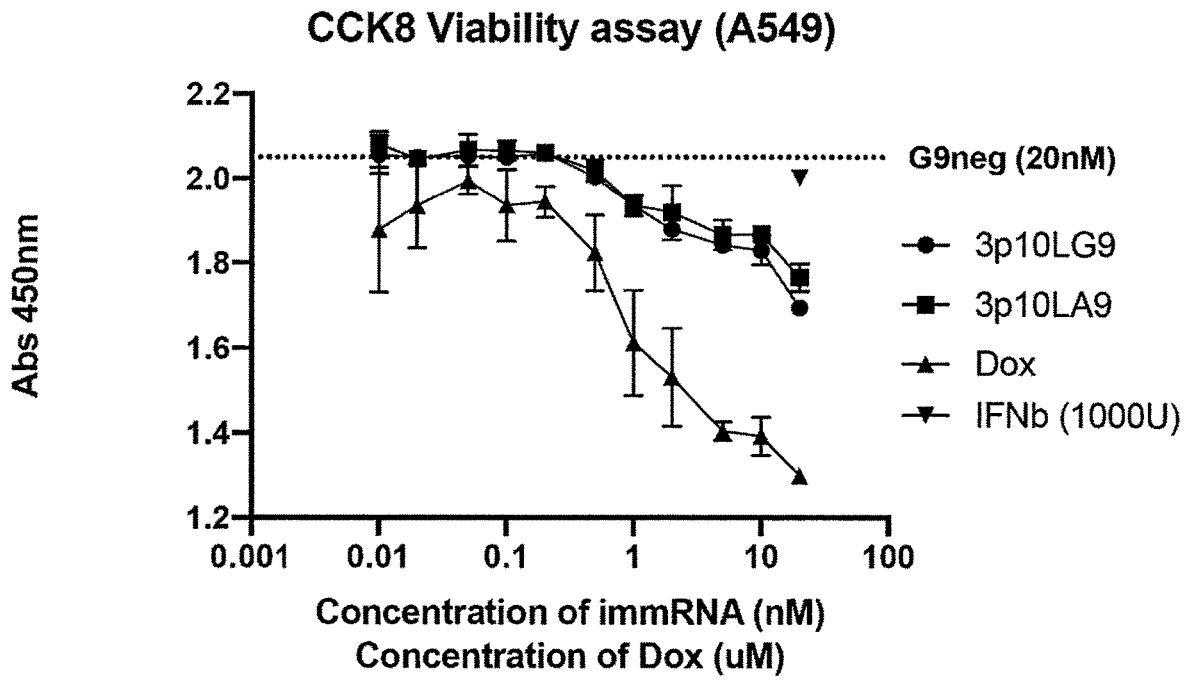
FIG. 21. A549 cell viability assay after treatment with immRNA. Quantification of live cells 24 h after transfection with 3p10LG9 (SEQ ID NO:26), 3p10LA9 (SEQ ID NO:25) or 3p10LG9 without 5' triphosphate at different concentrations. Dox (doxorubicine) was used as a positive control for cell death.

ImmRNA 3p10LG9 (SEQ ID NO:26) and 3p10LA9 (SEQ ID NO:25) showed increasing cytotoxic effects with increasing concentration. 3p10LG9 without 5' triphosphate was included as a control and did not show any cytotoxic effects. This control excluded potential cytotoxic effects of the transfection procedure on cells. For this experiment, A549 cells were seeded in a 96-well plate. One day later, cells were transfected with immRNA using 239fectin and were incubated at 37° C. incubator for 24 h. CCK-8 reagent (dojindo) was then added to cells and incubated in the dark for 30 min before adding stop solution. The colorimetric test depends on dehydrogenase activity in living cells and the OD value per well is proportional to the number of living cells. OD450 values were measured on a plate reader (FIG. 21).

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," "containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

What is claimed is:

1. Small hairpin RNA (shRNA) molecule having the structure, in 5' to 3' orientation, $X_1$-L-$X_2$, wherein $X_1$ and $X_2$ are each nucleotide sequences that are, not counting the nucleotide insertion creating the kink, of the same length and are 10, 20 or 30 nucleotides in length, and have sufficient complementarity to one another to form a double-stranded stem structure;

L is a nucleotide sequence forming a loop region;

the first nucleotide positioned at the 5' terminal end of $X_1$ is designated as n1 and is di- or triphosphorylated, and the last nucleotide positioned at the 3' terminal end of $X_2$ is designated nx, wherein x indicates the total number of nucleotides in the shRNA molecule, and is an integer of 25 to 65;

the shRNA molecule comprises a nucleotide insertion in $X_1$ in position n7 or higher or in $X_2$ at position nx–6 or lower that remains unpaired in the double-stranded stem structure and creates a kink, wherein n indicates the position of the nucleotide in the shRNA molecule.

2. The shRNA molecule of claim 1, wherein L is a nucleotide sequence of 1 to 10 nucleotides in length.

3. The shRNA molecule of claim 1, wherein $X_1$ and $X_2$ are with the exception of the nucleotide insertion creating the kink, fully complementary to one another.

4. The shRNA molecule of claim 1, wherein the nucleotide insertion is a nucleotide insertion of 1-2 nucleotides.

5. The shRNA molecule of claim 1, wherein the nucleotide insertion is a nucleotide insertion in $X_1$.

6. The shRNA molecule of claim 1, wherein the nucleotide insertion is in a position selected from the positions ranging from n7 to the penultimate position of $X_1$ or from the positions ranging from the second position of $X_2$ to nx–6.

7. The shRNA molecule of claim 6, wherein the nucleotide insertion is in a position selected from the positions ranging from n9 to the position 2 or 3 nucleotides upstream of the first nucleotide of the loop region or from the position 2 or 3 nucleotides downstream of the last nucleotide of the loop region to nx–8.

8. The shRNA molecule of claim 1, wherein the nucleotide insertion is G or A.

9. The shRNA molecule of claim 1, wherein the loop region L comprises or consists of the sequence UUCG.

10. The shRNA molecule of claim 1, wherein $X_1$ comprises or consists of a nucleotide sequence selected from the group consisting of:

|  |  |
|---|---|
| rrrnnyyyryy; | (SEQ ID NO: 1) |
| sswwwwssrss; | (SEQ ID NO: 2) |
| ggannnnnnnn; | (SEQ ID NO: 3) |
| ggannnnnncc; | (SEQ ID NO: 4) |
| ggannnuncncc; | (SEQ ID NO: 5) |
| ggawwuscncc; | (SEQ ID NO: 6) |
| ggauuuccrcc; | (SEQ ID NO: 7) |
| ggauuuccacc; or | (SEQ ID NO: 8) |
| ggauuuccgcc, | (SEQ ID NO: 9) | wherein r is g or a, y is u or c, w is a or u, s is g or c and n is a, g, u or c, and wherein the $X_1$ sequence preferably comprises the inserted unpaired nucleotide, this unpaired nucleotide preferably being the nucleotide at position 9.

11. The shRNA molecule of claim 1, wherein $X_2$ comprises or consists of a nucleotide sequence selected from the group consisting of:

|  |  |
|---|---|
| rrrrrnnyyy; | (SEQ ID NO: 10) |

```
                                     (SEQ ID NO: 11)
ssssWWWWss;

(SEQ ID NO: 12)
nnnnnnnucc;

(SEQ ID NO: 13)
ggnnnnnucc;

(SEQ ID NO: 14)
gggnannucc;

(SEQ ID NO: 15)
gggwawwucc;

(SEQ ID NO: 16)
ggggaaaucc,
``` wherein r is g or a, y is u or c, w is a or u, s is g or c and n is a, g, u or c.

12. The shRNA molecule of claim 1, wherein the shRNA molecule comprises or consists of a nucleotide sequence selected from the group consisting of:

```
                                     (SEQ ID NO: 17)
rrrnnyyyryyuucgrrrrrnnyyy;

(SEQ ID NO: 18)
sswwwwssrssuucgssssWWWwss;

(SEQ ID NO: 19)
ggannnnnnnnuucgnnnnnnnucc;

(SEQ ID NO: 20)
ggannnnnnccuucgggnnnnnucc;

(SEQ ID NO: 21)
ggannuncnccuucggggnannucc;

(SEQ ID NO: 22)
ggawwuscnccuucggggwawwucc;

(SEQ ID NO: 23)
ggauuuccnccuucggggaaaucc;

(SEQ ID NO: 24)
ggauuuccrccuucggggaaaucc;

(SEQ ID NO: 25)
ggauuuccaccuucggggaaaucc;
or (SEQ ID NO: 26)
ggauuuccgccuucggggaaaucc,
``` wherein r is g or a, y is u or c, w is a or u, s is g or c and n is a, g, u or c.

13. Composition comprising at least one small hairpin RNA (shRNA) molecule having the structure, in 5' to 3' orientation, $X_1$-L-$X_2$, wherein $X_1$ and $X_2$ are each nucleotide sequences that are, not counting the nucleotide insertion creating the kink, of the same length and are 10, 20 or 30 nucleotides in length, and have sufficient complementarity to one another to form a double-stranded stem structure;

L is a nucleotide sequence forming a loop region;

the first nucleotide positioned at the 5' terminal end of $X_1$ is designated as n1 and is di- or triphosphorylated, and the last nucleotide positioned at the 3' terminal end of $X_2$ is designated nx, wherein x indicates the total number of nucleotides in the shRNA molecule, and is an integer of 25 to 65;

the shRNA molecule comprises a nucleotide insertion in $X_1$ in position n7 or higher or in $X_2$ at position nx−6 or lower that remains unpaired in the double-stranded stem structure and creates a kink, wherein n indicates the position of the nucleotide in the shRNA molecule; and one or more excipients.

14. The composition of claim 13, wherein the composition comprises a plurality of shRNA molecules.

15. The composition of claim 13, wherein the composition is a pharmaceutical composition, an immunostimulatory composition, an antiviral composition or an anticancer composition.

16. The composition of claim 15, wherein the composition is a vaccine composition further comprising a vaccine and wherein the shRNA molecule(s) function as the adjuvant.

17. The composition of claim 15, wherein the composition is an antiviral composition further comprising an active antiviral agent or an anticancer composition further comprising an active anticancer agent.

18. Method for stimulating the immune system in a subject in need thereof, the method comprising administering an effective amount of at least one small hairpin RNA (shRNA) molecule having the structure, in 5' to 3' orientation, $X_1$-L-$X_2$, wherein the shRNA molecule binds to human retinoic acid-inducible gene 1 (RIG-I) receptor, and wherein $X_1$ and $X_2$ are each nucleotide sequences that are, not counting the nucleotide insertion creating the kink, of the same length and are 10, 20 or 30 nucleotides in length, and have sufficient complementarity to one another to form a double-stranded stem structure;

L is a nucleotide sequence forming a loop region;

the first nucleotide positioned at the 5' terminal end of $X_1$ is designated as n1 and is di- or triphosphorylated, and the last nucleotide positioned at the 3' terminal end of $X_2$ is designated nx, wherein x indicates the total number of nucleotides in the shRNA molecule, and is an integer of 25 to 65;

the shRNA molecule comprises a nucleotide insertion in $X_1$ in position n7 or higher or in $X_2$ at position nx−6 or lower that remains unpaired in the double-stranded stem structure and creates a kink, wherein n indicates the position of the nucleotide in the shRNA molecule, or a composition containing said shRNA molecule to said subject.

* * * * *